US008163895B2

(12) United States Patent
Sampath et al.

(10) Patent No.: US 8,163,895 B2
(45) Date of Patent: Apr. 24, 2012

(54) COMPOSITIONS FOR USE IN IDENTIFICATION OF ORTHOPOXVIRUSES

(75) Inventors: Rangarajan Sampath, San Diego, CA (US); Thomas A. Hall, Oceanside, CA (US); David J. Ecker, Encinitas, CA (US); Steven A. Hofstadler, Vista, CA (US)

(73) Assignee: Ibis Biosciences, Inc., Carlsbad, CA (US)

( * ) Notice: Subject to any disclaimer, the term of this patent is extended or adjusted under 35 U.S.C. 154(b) by 133 days.

(21) Appl. No.: 11/210,516

(22) Filed: Aug. 24, 2005

(65) Prior Publication Data

US 2006/0275749 A1 Dec. 7, 2006

Related U.S. Application Data

(63) Continuation-in-part of application No. 10/728,486, filed on Dec. 5, 2003, now Pat. No. 7,718,354.

(60) Provisional application No. 60/604,329, filed on Aug. 24, 2004.

(51) Int. Cl.
*C07H 21/04* (2006.01)
*C12Q 1/68* (2006.01)
*C12P 19/34* (2006.01)

(52) U.S. Cl. .................. 536/24.33; 536/23.1; 435/6.12; 435/91.2

(58) Field of Classification Search ........................ None
See application file for complete search history.

(56) References Cited

U.S. PATENT DOCUMENTS

| | | | |
|---|---|---|---|
| 4,075,475 | A | 2/1978 | Risby et al. |
| 4,683,195 | A | 7/1987 | Mullis et al. |
| 4,683,202 | A | 7/1987 | Mullis |
| 4,965,188 | A | 10/1990 | Mullis et al. |
| 5,015,845 | A | 5/1991 | Allen et al. |
| 5,072,115 | A | 12/1991 | Zhou |
| 5,143,905 | A | 9/1992 | Sivasubramanian et al. |
| 5,213,961 | A | 5/1993 | Bunn et al. |
| 5,219,727 | A | 6/1993 | Wang et al. |
| 5,288,611 | A | 2/1994 | Kohne |
| 5,436,129 | A | 7/1995 | Stapleton |
| 5,451,500 | A | 9/1995 | Stapleton |
| 5,472,843 | A | 12/1995 | Milliman |
| 5,476,774 | A | 12/1995 | Wang et al. |
| 5,484,808 | A | 1/1996 | Grinnell |
| 5,484,908 | A | 1/1996 | Froehler et al. |
| 5,502,177 | A | 3/1996 | Matteucci et al. |
| 5,503,980 | A | 4/1996 | Cantor |
| 5,504,327 | A | 4/1996 | Sproch et al. |
| 5,504,329 | A | 4/1996 | Mann et al. |
| 5,523,217 | A | 6/1996 | Lupski et al. |
| 5,527,669 | A | 6/1996 | Resnick et al. |
| 5,527,675 | A | 6/1996 | Coull et al. |
| 5,527,875 | A | 6/1996 | Yokoyama et al. |
| 5,547,835 | A | 8/1996 | Koster |
| 5,567,587 | A | 10/1996 | Kohne |
| 5,576,204 | A | 11/1996 | Blanco et al. |
| 5,580,733 | A | 12/1996 | Levis et al. |
| 5,605,798 | A | 2/1997 | Koster |
| 5,608,217 | A | 3/1997 | Franzen et al. |
| 5,612,179 | A | 3/1997 | Simons |
| 5,622,824 | A | 4/1997 | Koster |
| 5,625,184 | A | 4/1997 | Vestal et al. |
| 5,639,606 | A | 6/1997 | Willey |
| 5,641,632 | A | 6/1997 | Kohne |
| 5,645,985 | A | 7/1997 | Froehler et al. |
| 5,683,869 | A | 11/1997 | Ramsay Shaw et al. |
| 5,686,242 | A | 11/1997 | Bruice et al. |
| 5,691,141 | A | 11/1997 | Koster |
| 5,700,642 | A | 12/1997 | Monforte et al. |
| 5,702,895 | A | 12/1997 | Matsunaga et al. |
| 5,707,802 | A | 1/1998 | Sandhu et al. |
| 5,712,125 | A | 1/1998 | Uhlen |
| 5,716,825 | A | 2/1998 | Hancock et al. |
| 5,727,202 | A | 3/1998 | Kucala |
| 5,745,751 | A | 4/1998 | Nelson et al. |
| 5,747,246 | A | 5/1998 | Pannetier et al. |
| 5,747,251 | A | 5/1998 | Carson et al. |
| 5,753,467 | A | 5/1998 | Jensen et al. |
| 5,753,489 | A | 5/1998 | Kistner et al. |
| 5,759,771 | A | 6/1998 | Tilanus |
| 5,763,169 | A | 6/1998 | Sandhu et al. |
| 5,763,588 | A | 6/1998 | Matteucci et al. |
| 5,770,367 | A | 6/1998 | Southern et al. |
| 5,777,324 | A | 7/1998 | Hillenkamp |
| 5,814,442 | A | 9/1998 | Natarajan et al. |
| 5,822,824 | A | 10/1998 | Dion |
| 5,828,062 | A | 10/1998 | Jarrell et al. |
| 5,830,653 | A | 11/1998 | Froehler et al. |
| 5,830,655 | A | 11/1998 | Monforte et al. |

(Continued)

FOREIGN PATENT DOCUMENTS

CN 1202204 A 12/1998

(Continued)

OTHER PUBLICATIONS

Earl. et al. (1986) Proc. Natl. Acad. Sci 83: pp. 3659-36663.*
Buck et al. (1999) Biotechniques 27: 528-536.*
Stratagene Catalog 1988.*
Hurst et al. (1998) Anal. Chem vol. 70 pp. 2693-2698.*
Von Wintzingerode et al. (2002) Proc. Natl. Acad. Sci. vol. 99 bo 10 pp. 7039-7044.*
11-210-516-SEQ ID 16 BLAST.pdf Mar. 12, 2009.*
11-210-516 SEQ ID 39 BLAST.pdf Mar. 12, 2009.*
Aaserud D.J., et al., "Accurate Base Composition of Double-Strand DNA by Mass Spectrometry," American Society for Mass Spectrometry, 1996, vol. 7 (12), pp. 1266-1269.
Aaserud D.J., et al., "DNA Sequencing with Blackbody Infrared Radioactive Dissociation of Electrosprayed Ions," International Journal of Mass Spectrometry and Icon Processes, 1997, vol. 167-168, pp. 705-712.

(Continued)

*Primary Examiner* — Young J Kim
*Assistant Examiner* — Angela M Bertagna
(74) *Attorney, Agent, or Firm* — Casimir Jones, S.C.

(57) ABSTRACT

Oligonucleotide primers and compositions and kits containing the same for rapid identification of orthopoxviruses by amplification of a segment of viral nucleic acid followed by molecular mass analysis are provided.

15 Claims, 4 Drawing Sheets

U.S. PATENT DOCUMENTS

| | | | |
|---|---|---|---|
| 5,830,853 A | 11/1998 | Backstrom et al. |
| 5,832,489 A | 11/1998 | Kucala |
| 5,834,255 A | 11/1998 | van Gemen et al. |
| 5,845,174 A | 12/1998 | Yasui et al. |
| 5,849,492 A | 12/1998 | Rogan |
| 5,849,497 A | 12/1998 | Steinman |
| 5,849,901 A | 12/1998 | Mabilat et al. |
| 5,851,765 A | 12/1998 | Koster |
| 5,856,174 A | 1/1999 | Lipshutz et al. |
| 5,864,137 A | 1/1999 | Becker et al. |
| 5,866,429 A | 2/1999 | Bloch |
| 5,869,242 A | 2/1999 | Kamb |
| 5,871,697 A | 2/1999 | Rothberg et al. |
| 5,872,003 A | 2/1999 | Koster |
| 5,876,936 A | 3/1999 | Ju |
| 5,876,938 A | 3/1999 | Stolowitz et al. |
| 5,885,775 A | 3/1999 | Haff et al. |
| 5,900,481 A | 5/1999 | Lough et al. |
| 5,928,905 A | 7/1999 | Stemmer et al. |
| 5,928,906 A | 7/1999 | Koster et al. |
| 5,965,363 A | 10/1999 | Monforte et al. |
| 5,965,383 A | 10/1999 | Vogel et al. |
| 5,972,693 A | 10/1999 | Rothberg et al. |
| 5,976,798 A | 11/1999 | Parker et al. |
| 5,981,176 A | 11/1999 | Wallace |
| 5,981,178 A | 11/1999 | Tsui et al. |
| 5,981,190 A | 11/1999 | Israel |
| 5,994,066 A | 11/1999 | Bergeron et al. |
| 6,001,564 A | 12/1999 | Bergeron et al. |
| 6,001,584 A | 12/1999 | Karin et al. |
| 6,005,096 A | 12/1999 | Matteucci et al. |
| 6,007,690 A | 12/1999 | Nelson et al. |
| 6,007,992 A | 12/1999 | Lin et al. |
| 6,015,666 A | 1/2000 | Springer et al. |
| 6,018,713 A | 1/2000 | Coli et al. |
| 6,024,925 A | 2/2000 | Little et al. |
| 6,028,183 A | 2/2000 | Lin et al. |
| 6,043,031 A | 3/2000 | Koster et al. |
| 6,046,005 A | 4/2000 | Ju et al. |
| 6,051,378 A | 4/2000 | Monforte et al. |
| 6,054,278 A | 4/2000 | Dodge et al. |
| 6,055,487 A | 4/2000 | Margery et al. |
| 6,060,246 A | 5/2000 | Summerton et al. |
| 6,061,686 A | 5/2000 | Gauvin et al. |
| 6,063,031 A | 5/2000 | Cundari et al. |
| 6,074,823 A | 6/2000 | Koster |
| 6,074,831 A | 6/2000 | Yakhini et al. |
| 6,090,558 A | 7/2000 | Butler et al. |
| 6,104,028 A | 8/2000 | Hunter et al. |
| 6,110,710 A | 8/2000 | Smith et al. |
| 6,111,251 A | 8/2000 | Hillenkamp |
| 6,133,436 A | 10/2000 | Koster et al. |
| 6,140,053 A | 10/2000 | Koster |
| 6,146,144 A | 11/2000 | Fowler et al. |
| 6,146,854 A | 11/2000 | Koster et al. |
| 6,153,389 A | 11/2000 | Haarer et al. |
| 6,159,681 A | 12/2000 | Zebala |
| 6,180,339 B1 | 1/2001 | Sandhu et al. |
| 6,180,372 B1 | 1/2001 | Franzen |
| 6,187,842 B1 | 2/2001 | Kobayashi et al. |
| 6,194,144 B1 | 2/2001 | Koster |
| 6,197,498 B1 | 3/2001 | Koster |
| 6,214,555 B1 | 4/2001 | Leushner et al. |
| 6,218,118 B1 | 4/2001 | Sampson et al. |
| 6,221,587 B1 | 4/2001 | Ecker et al. |
| 6,221,598 B1 | 4/2001 | Schumm et al. |
| 6,221,601 B1 | 4/2001 | Koster et al. |
| 6,221,605 B1 | 4/2001 | Koster |
| 6,225,450 B1 | 5/2001 | Koster |
| 6,235,476 B1 | 5/2001 | Bergmann et al. |
| 6,235,478 B1 | 5/2001 | Koster |
| 6,235,480 B1 | 5/2001 | Shultz et al. |
| 6,238,871 B1 | 5/2001 | Koster |
| 6,238,927 B1 | 5/2001 | Abrams et al. |
| 6,239,159 B1 | 5/2001 | Brown et al. |
| 6,258,538 B1 | 7/2001 | Koster et al. |
| 6,261,769 B1 | 7/2001 | Everett et al. |
| 6,265,716 B1 | 7/2001 | Hunter et al. |
| 6,265,718 B1 | 7/2001 | Park et al. |
| 6,266,131 B1 | 7/2001 | Hamada et al. |
| 6,266,144 B1 | 7/2001 | Li |
| 6,268,129 B1 | 7/2001 | Gut et al. |
| 6,268,131 B1 | 7/2001 | Kang et al. |
| 6,268,144 B1 | 7/2001 | Koster |
| 6,268,146 B1 | 7/2001 | Shultz et al. |
| 6,270,973 B1 | 8/2001 | Lewis et al. |
| 6,270,974 B1 | 8/2001 | Shultz et al. |
| 6,274,726 B1 | 8/2001 | Laugharn, Jr. et al. |
| 6,277,573 B1 | 8/2001 | Koster |
| 6,277,578 B1 | 8/2001 | Shultz et al. |
| 6,277,634 B1 | 8/2001 | McCall et al. |
| 6,300,076 B1 | 10/2001 | Koster |
| 6,303,297 B1 | 10/2001 | Lincoln et al. |
| 6,312,893 B1 | 11/2001 | Van Ness et al. |
| 6,312,902 B1 | 11/2001 | Shultz et al. |
| 6,322,970 B1 | 11/2001 | Little et al. |
| 6,361,940 B1 | 3/2002 | Van Ness et al. |
| 6,372,424 B1 | 4/2002 | Brow et al. |
| 6,389,428 B1 | 5/2002 | Rigault et al. |
| 6,391,551 B1 | 5/2002 | Shultz et al. |
| 6,393,367 B1 | 5/2002 | Tang et al. |
| 6,419,932 B1 | 7/2002 | Dale |
| 6,423,966 B2 | 7/2002 | Hillenkamp et al. |
| 6,428,955 B1 | 8/2002 | Koster et al. |
| 6,428,956 B1 | 8/2002 | Crooke et al. |
| 6,432,651 B1 | 8/2002 | Hughes et al. |
| 6,436,635 B1 | 8/2002 | Fu et al. |
| 6,436,640 B1 | 8/2002 | Simmons et al. |
| 6,453,244 B1 | 9/2002 | Oefner |
| 6,458,533 B1 | 10/2002 | Felder et al. |
| 6,468,743 B1 | 10/2002 | Romick et al. |
| 6,468,748 B1 | 10/2002 | Monforte et al. |
| 6,475,143 B2 | 11/2002 | Iliff |
| 6,475,736 B1 | 11/2002 | Stanton, Jr. |
| 6,475,738 B2 | 11/2002 | Shuber et al. |
| 6,479,239 B1 | 11/2002 | Anderson et al. |
| 6,500,621 B2 | 12/2002 | Koster |
| 6,553,317 B1 | 4/2003 | Lincoln et al. |
| 6,558,902 B1 | 5/2003 | Hillenkamp |
| 6,563,025 B1 | 5/2003 | Song et al. |
| 6,566,055 B1 | 5/2003 | Monforte et al. |
| 6,568,055 B1 | 5/2003 | Tang et al. |
| 6,582,916 B1 | 6/2003 | Schmidt et al. |
| 6,586,584 B2 | 7/2003 | McMillian et al. |
| 6,589,485 B2 | 7/2003 | Koster |
| 6,602,662 B1 | 8/2003 | Koster et al. |
| 6,605,433 B1 | 8/2003 | Fliss et al. |
| 6,610,492 B1 | 8/2003 | Stanton, Jr. et al. |
| 6,613,509 B1 | 9/2003 | Chen |
| 6,613,520 B2 | 9/2003 | Ashby |
| 6,623,928 B2 | 9/2003 | Van Ness et al. |
| 6,638,714 B1 | 10/2003 | Linnen et al. |
| 6,680,476 B1 | 1/2004 | Hidalgo et al. |
| 6,682,889 B1 | 1/2004 | Wang et al. |
| 6,705,530 B2 | 3/2004 | Kiekhaefer |
| 6,706,530 B2 | 3/2004 | Hillenkamp |
| 6,723,510 B2 * | 4/2004 | Lubenow et al. ............... 435/6 |
| 6,783,939 B2 | 8/2004 | Olmsted et al. |
| 6,800,289 B2 | 10/2004 | Nagata et al. |
| 6,813,615 B1 | 11/2004 | Colasanti et al. |
| 6,836,742 B2 | 12/2004 | Brekenfeld |
| 6,852,487 B1 | 2/2005 | Barany et al. |
| 6,856,914 B1 | 2/2005 | Pelech |
| 6,875,593 B2 | 4/2005 | Froehler et al. |
| 6,906,316 B2 | 6/2005 | Sugiyama et al. |
| 6,906,319 B2 | 6/2005 | Hoyes |
| 6,914,137 B2 | 7/2005 | Baker |
| 6,977,148 B2 | 12/2005 | Dean et al. |
| 6,994,962 B1 | 2/2006 | Thilly |
| 7,022,835 B1 | 4/2006 | Rauth et al. |
| 7,024,370 B2 | 4/2006 | Epler et al. |
| 7,108,974 B2 | 9/2006 | Ecker et al. |
| 7,198,893 B1 | 4/2007 | Köster et al. |
| 7,217,510 B2 | 5/2007 | Ecker et al. |
| 7,226,739 B2 | 6/2007 | Ecker et al. |
| 7,255,992 B2 | 8/2007 | Ecker et al. |
| 7,285,422 B1 | 10/2007 | Little et al. |

| | | |
|---|---|---|
| 7,312,036 B2 | 12/2007 | Sampath et al. |
| 7,321,828 B2 | 1/2008 | Cowsert et al. |
| 7,349,808 B1 | 3/2008 | Kreiswirth et al. |
| 7,390,458 B2 | 6/2008 | Burow et al. |
| 7,419,787 B2 | 9/2008 | Köster |
| 7,501,251 B2 | 3/2009 | Köster et al. |
| 7,666,588 B2 | 2/2010 | Ecker et al. |
| 7,718,354 B2 | 5/2010 | Ecker et al. |
| 7,741,036 B2 | 6/2010 | Ecker et al. |
| 7,781,162 B2 | 8/2010 | Ecker et al. |
| 2001/0039263 A1 | 11/2001 | Matthes et al. |
| 2002/0006611 A1 | 1/2002 | Portugal et al. |
| 2002/0028923 A1 | 3/2002 | Cowsert et al. |
| 2002/0042112 A1 | 4/2002 | Koster et al. |
| 2002/0042506 A1 | 4/2002 | Kristyanne et al. |
| 2002/0045178 A1 | 4/2002 | Cantor et al. |
| 2002/0055101 A1 | 5/2002 | Bergeron et al. |
| 2002/0090320 A1 | 7/2002 | Burow et al. |
| 2002/0120408 A1 | 8/2002 | Kreiswirth et al. |
| 2002/0137057 A1 | 9/2002 | Wold et al. |
| 2002/0138210 A1 | 9/2002 | Wilkes et al. |
| 2002/0150903 A1 | 10/2002 | Koster |
| 2002/0150927 A1 | 10/2002 | Matray et al. |
| 2002/0168630 A1 | 11/2002 | Fleming et al. |
| 2002/0187490 A1 | 12/2002 | Tiedje et al. |
| 2003/0017487 A1 | 1/2003 | Xue et al. |
| 2003/0027135 A1 | 2/2003 | Ecker et al. |
| 2003/0039976 A1* | 2/2003 | Haff ................................ 435/6 |
| 2003/0050470 A1 | 3/2003 | An et al. |
| 2003/0064483 A1 | 4/2003 | Shaw et al. |
| 2003/0073112 A1 | 4/2003 | Zhang et al. |
| 2003/0082539 A1 | 5/2003 | Ecker et al. |
| 2003/0084483 A1 | 5/2003 | Simpson et al. |
| 2003/0101172 A1 | 5/2003 | De La Huerga |
| 2003/0104410 A1 | 6/2003 | Mittmann |
| 2003/0104699 A1 | 6/2003 | Minamihaba et al. |
| 2003/0113738 A1 | 6/2003 | Liu et al. |
| 2003/0113745 A1 | 6/2003 | Monforte et al. |
| 2003/0119018 A1 | 6/2003 | Omura et al. |
| 2003/0124556 A1 | 7/2003 | Ecker et al. |
| 2003/0125192 A1 | 7/2003 | Moon |
| 2003/0129589 A1 | 7/2003 | Koster et al. |
| 2003/0134312 A1 | 7/2003 | Burgoyne |
| 2003/0148281 A1 | 8/2003 | Glucksmann |
| 2003/0148284 A1 | 8/2003 | Vision et al. |
| 2003/0167133 A1 | 9/2003 | Ecker et al. |
| 2003/0167134 A1 | 9/2003 | Ecker et al. |
| 2003/0175695 A1 | 9/2003 | Ecker et al. |
| 2003/0175696 A1 | 9/2003 | Ecker et al. |
| 2003/0175697 A1 | 9/2003 | Ecker et al. |
| 2003/0175729 A1 | 9/2003 | Van Eijk et al. |
| 2003/0186247 A1 | 10/2003 | Smarason et al. |
| 2003/0187588 A1 | 10/2003 | Ecker et al. |
| 2003/0187593 A1 | 10/2003 | Ecker et al. |
| 2003/0187615 A1 | 10/2003 | Epler et al. |
| 2003/0190605 A1 | 10/2003 | Ecker et al. |
| 2003/0190635 A1 | 10/2003 | McSwiggen |
| 2003/0194699 A1 | 10/2003 | Lewis et al. |
| 2003/0203398 A1 | 10/2003 | Bramucci et al. |
| 2003/0220844 A1 | 11/2003 | Marnellos et al. |
| 2003/0224377 A1* | 12/2003 | Wengel et al. ................ 435/6 |
| 2003/0225529 A1 | 12/2003 | Ecker et al. |
| 2003/0228571 A1 | 12/2003 | Ecker et al. |
| 2003/0228597 A1 | 12/2003 | Cowsert et al. |
| 2003/0228613 A1 | 12/2003 | Bornarth et al. |
| 2004/0005555 A1 | 1/2004 | Rothman et al. |
| 2004/0006611 A1 | 1/2004 | Yi |
| 2004/0013703 A1 | 1/2004 | Ralph et al. |
| 2004/0014957 A1 | 1/2004 | Eldrup et al. |
| 2004/0023207 A1 | 2/2004 | Polansky |
| 2004/0023209 A1 | 2/2004 | Jonasson |
| 2004/0029129 A1 | 2/2004 | Wang et al. |
| 2004/0038206 A1 | 2/2004 | Zhang et al. |
| 2004/0038208 A1 | 2/2004 | Fisher et al. |
| 2004/0038234 A1 | 2/2004 | Gut et al. |
| 2004/0038385 A1 | 2/2004 | Langlois et al. |
| 2004/0081993 A1 | 4/2004 | Cantor et al. |
| 2004/0101809 A1 | 5/2004 | Weiss et al. |
| 2004/0110169 A1 | 6/2004 | Ecker et al. |
| 2004/0111221 A1 | 6/2004 | Beattie et al. |
| 2004/0117129 A1 | 6/2004 | Ecker et al. |
| 2004/0121309 A1 | 6/2004 | Ecker et al. |
| 2004/0121310 A1 | 6/2004 | Ecker et al. |
| 2004/0121311 A1 | 6/2004 | Ecker et al. |
| 2004/0121312 A1 | 6/2004 | Ecker et al. |
| 2004/0121313 A1 | 6/2004 | Ecker et al. |
| 2004/0121314 A1 | 6/2004 | Ecker et al. |
| 2004/0121315 A1 | 6/2004 | Ecker et al. |
| 2004/0121329 A1 | 6/2004 | Ecker et al. |
| 2004/0121335 A1 | 6/2004 | Ecker et al. |
| 2004/0121340 A1 | 6/2004 | Ecker et al. |
| 2004/0122598 A1 | 6/2004 | Ecker et al. |
| 2004/0122857 A1 | 6/2004 | Ecker et al. |
| 2004/0126764 A1 | 7/2004 | Lasken et al. |
| 2004/0137013 A1 | 7/2004 | Katinger et al. |
| 2004/0161770 A1 | 8/2004 | Ecker et al. |
| 2004/0180328 A1 | 9/2004 | Ecker et al. |
| 2004/0185438 A1 | 9/2004 | Ecker |
| 2004/0191769 A1 | 9/2004 | Marino et al. |
| 2004/0202997 A1 | 10/2004 | Ecker et al. |
| 2004/0209260 A1 | 10/2004 | Ecker et al. |
| 2004/0219517 A1 | 11/2004 | Ecker et al. |
| 2004/0253583 A1 | 12/2004 | Ecker et al. |
| 2004/0253619 A1 | 12/2004 | Ecker et al. |
| 2005/0026147 A1 | 2/2005 | Walker et al. |
| 2005/0026164 A1 | 2/2005 | Zhou |
| 2005/0026641 A1 | 2/2005 | Hokao |
| 2005/0027459 A1 | 2/2005 | Ecker et al. |
| 2005/0065813 A1 | 3/2005 | Mishelevich et al. |
| 2005/0130196 A1 | 6/2005 | Hofstadler et al. |
| 2005/0130216 A1 | 6/2005 | Becker et al. |
| 2005/0142584 A1 | 6/2005 | Willson et al. |
| 2005/0250125 A1 | 11/2005 | Novakoff |
| 2005/0266397 A1 | 12/2005 | Ecker et al. |
| 2005/0266411 A1 | 12/2005 | Hofstadler et al. |
| 2006/0020391 A1 | 1/2006 | Kreiswirth et al. |
| 2006/0057605 A1 | 3/2006 | Sampath et al. |
| 2006/0121520 A1 | 6/2006 | Ecker et al. |
| 2006/0172330 A1 | 8/2006 | Osborn et al. |
| 2006/0205040 A1 | 9/2006 | Sampath |
| 2006/0240412 A1 | 10/2006 | Hall et al. |
| 2006/0259249 A1 | 11/2006 | Sampath et al. |
| 2006/0275788 A1 | 12/2006 | Ecker et al. |
| 2007/0048735 A1 | 3/2007 | Ecker et al. |
| 2007/0218467 A1 | 9/2007 | Ecker et al. |
| 2008/0160512 A1 | 7/2008 | Ecker et al. |
| 2008/0311558 A1 | 12/2008 | Ecker et al. |
| 2009/0004643 A1 | 1/2009 | Ecker et al. |
| 2009/0023150 A1 | 1/2009 | Koster et al. |
| 2009/0042203 A1 | 2/2009 | Koster |
| 2009/0092977 A1 | 4/2009 | Koster |
| 2009/0125245 A1 | 5/2009 | Hofstadler et al. |
| 2009/0148829 A1 | 6/2009 | Ecker et al. |
| 2009/0148836 A1 | 6/2009 | Ecker et al. |
| 2009/0148837 A1 | 6/2009 | Ecker et al. |
| 2009/0182511 A1 | 7/2009 | Ecker et al. |
| 2009/0239224 A1 | 9/2009 | Ecker et al. |
| 2009/0280471 A1 | 11/2009 | Ecker et al. |
| 2010/0070194 A1 | 3/2010 | Ecker et al. |
| 2010/0145626 A1 | 6/2010 | Ecker et al. |
| 2010/0184035 A1 | 7/2010 | Hall et al. |

FOREIGN PATENT DOCUMENTS

| | | |
|---|---|---|
| DE | 19732086 A1 | 1/1999 |
| DE | 19802905 A1 | 7/1999 |
| DE | 19824280 A1 | 12/1999 |
| DE | 19852167 A1 | 5/2000 |
| DE | 19943374 A1 | 3/2001 |
| DE | 10132147 B4 | 2/2003 |
| EP | 281390 A2 | 9/1988 |
| EP | 633321 A1 | 1/1995 |
| EP | 620862 B1 | 4/1998 |
| EP | 1035219 A1 | 9/2000 |
| EP | 1138782 A2 | 10/2001 |
| EP | 1234888 A2 | 8/2002 |
| EP | 1308506 A1 | 5/2003 |
| EP | 1310571 A2 | 5/2003 |
| EP | 1333101 A1 | 8/2003 |

| | | | | | | |
|---|---|---|---|---|---|---|
| EP | 1365031 | A1 | 11/2003 | WO | WO0173199 A1 | 10/2001 |
| EP | 1234888 | A3 | 1/2004 | WO | WO0177392 A2 | 10/2001 |
| EP | 1748072 | A1 | 1/2007 | WO | WO0196388 A2 | 12/2001 |
| FR | 2811321 | A1 | 1/2002 | WO | WO0202811 A2 | 1/2002 |
| GB | 2325002 | A | 11/1998 | WO | WO0210186 A1 | 2/2002 |
| GB | 2339905 | A | 2/2000 | WO | WO0210444 A1 | 2/2002 |
| JP | 5276999 | | 10/1993 | WO | WO0218641 A2 | 3/2002 |
| JP | 11137259 | A | 5/1999 | WO | WO0221108 A2 | 3/2002 |
| JP | 24024206 | A2 | 1/2004 | WO | WO0222873 A1 | 3/2002 |
| JP | 2004000200 | A2 | 1/2004 | WO | WO0224876 A2 | 3/2002 |
| JP | 24201641 | A2 | 7/2004 | WO | WO0250307 A1 | 6/2002 |
| JP | 24201679 | A2 | 7/2004 | WO | WO02057491 A2 | 7/2002 |
| WO | WO8803957 | A1 | 6/1988 | WO | WO02070664 A2 | 9/2002 |
| WO | WO9015157 | A1 | 12/1990 | WO | WO02070728 A2 | 9/2002 |
| WO | WO9205182 | A1 | 4/1992 | WO | WO02070737 A2 | 9/2002 |
| WO | WO9208117 | A1 | 5/1992 | WO | WO02077278 A1 | 10/2002 |
| WO | WO9209703 | A1 | 6/1992 | WO | WO02099034 A2 | 12/2002 |
| WO | WO9219774 | A1 | 11/1992 | WO | WO02099095 A2 | 12/2002 |
| WO | WO9303186 | A1 | 2/1993 | WO | WO02099129 A2 | 12/2002 |
| WO | WO9305182 | A1 | 3/1993 | WO | WO02099130 A2 | 12/2002 |
| WO | WO9308297 | A1 | 4/1993 | WO | WO03001976 A2 | 1/2003 |
| WO | WO9416101 | A2 | 7/1994 | WO | WO03002750 A2 | 1/2003 |
| WO | WO9419490 | A1 | 9/1994 | WO | WO03008636 A2 | 1/2003 |
| WO | WO9421822 | A1 | 9/1994 | WO | WO03012058 A2 | 2/2003 |
| WO | WO9504161 | A1 | 2/1995 | WO | WO03012074 A2 | 2/2003 |
| WO | WO9511996 | A1 | 5/1995 | WO | WO03014382 A2 | 2/2003 |
| WO | WO9513395 | A1 | 5/1995 | WO | WO03016546 A1 | 2/2003 |
| WO | WO9513396 | A2 | 5/1995 | WO | WO03018636 A2 | 3/2003 |
| WO | WO9531997 | A1 | 11/1995 | WO | WO03020890 A2 | 3/2003 |
| WO | WO9606187 | A1 | 2/1996 | WO | WO03033732 A2 | 4/2003 |
| WO | WO9616186 | A1 | 5/1996 | WO | WO03054162 A2 | 7/2003 |
| WO | WO9629431 | A2 | 9/1996 | WO | WO03054755 A2 | 7/2003 |
| WO | WO9632504 | A2 | 10/1996 | WO | WO03060163 A2 | 7/2003 |
| WO | WO9635450 | A1 | 11/1996 | WO | WO03075955 A1 | 9/2003 |
| WO | WO9637630 | A1 | 11/1996 | WO | WO03088979 A2 | 10/2003 |
| WO | WO9733000 | A1 | 9/1997 | WO | WO03093506 A2 | 11/2003 |
| WO | WO9734909 | A1 | 9/1997 | WO | WO03097869 A2 | 11/2003 |
| WO | WO9737041 | A2 | 10/1997 | WO | WO03100035 A2 | 12/2003 |
| WO | WO9747766 | A1 | 12/1997 | WO | WO03100068 A1 | 12/2003 |
| WO | WO9803684 | A1 | 1/1998 | WO | WO03102191 A1 | 12/2003 |
| WO | WO9812355 | A1 | 3/1998 | WO | WO03104410 A2 | 12/2003 |
| WO | WO9814616 | A1 | 4/1998 | WO | WO03106635 A2 | 12/2003 |
| WO | WO9815652 | A1 | 4/1998 | WO | WO2004003511 A2 | 1/2004 |
| WO | WO9820020 | A2 | 5/1998 | WO | WO2004009849 A1 | 1/2004 |
| WO | WO9820157 | A2 | 5/1998 | WO | WO2004011651 A1 | 2/2004 |
| WO | WO9820166 | A2 | 5/1998 | WO | WO2004013357 A2 | 2/2004 |
| WO | WO9826095 | A1 | 6/1998 | WO | WO2004040013 A1 | 5/2004 |
| WO | WO9831830 | A1 | 7/1998 | WO | WO2004044123 A2 | 5/2004 |
| WO | WO9835057 | A1 | 8/1998 | WO | WO2004044247 A2 | 5/2004 |
| WO | WO9840520 | A1 | 9/1998 | WO | WO 2004/048511 A2 | 6/2004 |
| WO | WO9854571 | A1 | 12/1998 | WO | WO2004052175 A2 | 6/2004 |
| WO | WO9854751 | A1 | 12/1998 | WO | WO2004053076 A2 | 6/2004 |
| WO | WO9905319 | A2 | 2/1999 | WO | WO2004053141 A2 | 6/2004 |
| WO | WO9912040 | A2 | 3/1999 | WO | WO2004053164 A1 | 6/2004 |
| WO | WO9913104 | A1 | 3/1999 | WO | WO 2004/060278 A2 | 7/2004 |
| WO | WO9914375 | A2 | 3/1999 | WO | WO2004070001 A2 | 8/2004 |
| WO | WO9929898 | A2 | 6/1999 | WO | WO2004072230 A2 | 8/2004 |
| WO | WO9931278 | A1 | 6/1999 | WO | WO2004072231 A2 | 8/2004 |
| WO | WO9957318 | A2 | 11/1999 | WO | WO 2004/052175 A3 | 11/2004 |
| WO | WO9958713 | A2 | 11/1999 | WO | WO2004101809 A2 | 11/2004 |
| WO | WO9960183 | A1 | 11/1999 | WO | WO2005003384 A1 | 1/2005 |
| WO | WO0032750 | A1 | 6/2000 | WO | WO2005009202 A2 | 2/2005 |
| WO | WO0038636 | A1 | 7/2000 | WO | WO2005012572 A1 | 2/2005 |
| WO | WO0063362 | A1 | 10/2000 | WO | WO2005024046 A2 | 3/2005 |
| WO | WO0066789 | A2 | 11/2000 | WO | WO2005036369 A2 | 4/2005 |
| WO | WO0077260 | A1 | 12/2000 | WO | WO2005054454 A1 | 6/2005 |
| WO | WO0100828 | A2 | 1/2001 | WO | WO2005075686 A1 | 8/2005 |
| WO | WO0107648 | A1 | 2/2001 | WO | WO2005086634 A2 | 9/2005 |
| WO | WO0112853 | A1 | 2/2001 | WO | WO2005091971 A2 | 10/2005 |
| WO | WO0123604 | A2 | 4/2001 | WO | WO2005098047 A2 | 10/2005 |
| WO | WO0123608 | A2 | 4/2001 | WO | WO2005116263 A2 | 12/2005 |
| WO | WO0132930 | A1 | 5/2001 | WO | WO2006089762 A1 | 8/2006 |
| WO | WO0140497 | A2 | 6/2001 | WO | WO2006094238 A2 | 9/2006 |
| WO | WO0146404 | A1 | 6/2001 | WO | WO2006135400 A2 | 12/2006 |
| WO | WO0151661 | A2 | 7/2001 | WO | WO2007014045 A2 | 2/2007 |
| WO | WO0151662 | A1 | 7/2001 | WO | WO2007086904 A2 | 8/2007 |
| WO | WO0157263 | A1 | 8/2001 | WO | WO2008104002 A2 | 8/2008 |
| WO | WO0157518 | A2 | 8/2001 | WO | WO2008118809 A1 | 10/2008 |
| WO | WO0173119 | A2 | 10/2001 | | | |

OTHER PUBLICATIONS

Adam E., et al., "Characterization of Intertype Specific Epitopes on Adenovirus Hexons," Archives of Virology, 1998, vol. 143 (9), pp. 1669-1682.

Adam E., et al., "Intertype Specific Epitope Structure of Adenovirus Hexon," Acta Microbiologica et Immunologica Hungarica, 1998, vol. 45 (3-4), pp. 311-316.

Adam E., et al., "Molecular Structure of the Two-Dimensional Hexon Crystalline Array and of Adenovirus Capsid," Acta Microbiologica et Immunologica Hungarica, 1998, vol. 45 (3-4), pp. 305-310.

Adrian T., et al., "DNA Restriction Analysis of Adenovirus Prototypes 1 to 41," Archives of Virology, 1986, vol. 91 (3-4), pp. 277-290.

Adzhar A., et al., "Universal Oligonucleotides for the Detection of Infectious Bronchitis Virus by Thepolymerase Chain Reaction," Avian Pathology : Journal of the W.V.P.A, 1996, vol. 25 (4), pp. 817-836.

Agostin I H.T., et al., "Complete Genome of a JC Virus Genotype Type 6 from the Brain of an African American with Progressive Multifocal Leukoencephalopathy," Journal of Human Virology, 1998, vol. 1 (4), pp. 267-272.

Aires De Sousa M., et al., "Bridges from Hospitals to the Laboratory: Genetic Portraits of Methicillin-Resistant Staphylococcus Aureus Clones," FEMS Immunology and Medical Microbiology, 2004, vol. 40 (2), pp. 101-111.

Akalu A., et al., "Rapid Identification of Subgenera of Human Adenovirus by Serological and PCR Assays," Journal of Virological Methods, 1998, vol. 71 (2), pp. 187-196.

Alba M.M., et al., "Vida: A Virus Database System for the Organization of Animal Virus Genome Open ReadingFrames," Nucleic Acids Research, vol. 29 (1), pp. 133- 136, published 2001.

Allaouchiche B., et al., "Clinical Impact of Rapid Oxacillin Susceptibility Testing Using a PCR Assay in Staphylococcus Aureus Bactaeremia," The Journal of Infection, 1999, vol. 39 (3), pp. 198-204.

Allawi H.T., et al., "Thermodynamics and NMR of Internal G.T. Mismatches in DNA," Biochemistry, 1997, Vol. 36 (34), pp. 10581-10594.

Altschuel S.F., et al., "Basic Local Alignment Search Tool," Journal of Molecular Biology, 1990, vol. 215 (3), pp. 403-410.

Altschuel S.F., et al., "Gapped BLAST and PSI-BLAST: A New Generation of Protein Database Search Programs," Nucleic Acids Research, 1997, vol. 25 (17), pp. 3389-3402.

Alves-Silva J., et al., "The Ancestry of Brazilian mtDNA Linages," The American Journal of Human Genetics, 2000, vol. 67 (2), pp. 444-461.

Amano Y., et al., "Detection of Influenza Virus: Traditional Approaches and Development of Biosensors," Analytical and Bioanalytical Chemistry, 2005, vol. 381 (1), pp. 156-164.

Amexis G., et al., "Quantitative Mutant Analysis of Viral Quasispecies by Chip-Based Matrix Assisted LaserDesorption Ionization Time-of-Flight Mass Spectrometry," Proceedings of the National Academy of Sciences, 2001, vol. 98 (21), pp. 12097-12102.

Anderson M.L.M., "Quantitative Filter Hybridization" in: Nucleic Acid Hybridization, Names B.D. ed., IRL Press, 1985, pp. 73-111.

Anderson S., et al., "Sequence and Organization of the Human Mitochondrial Genome," Nature, 1981, vol. 290 (5806), pp. 457-465.

Andreasson H., et al., "Mitochondrial Sequence Analysis for Forensic Identification Using Pyrosequencing Technology," BioTechniques, 2002, vol. 32 (1), pp. 124-133.

Anthony R.M., et al., "Use of the Polymerase Chain Reaction for Rapid Detection of High—Level Mupirocin Resistance in Staphylococci," European Journal of Clinical Microbiology & Infectious Diseases, 1999, vol. 18 (1), pp. 30-34.

Arbique J., et al., "Comparison of the Velogene Rapid Mrsa Identification Assay, Denka MRSAScreen Assay, and BBL Crystal MRSA ID System for Rapid Identification of Methicillin-Resistant Staphylococcus Aureus," Diagnositic Microbiology and Infectious Diseases, 2001, vol. 40 (1-2), pp. 5-10.

Archer G.L., et al., "Detection of Methicillin Resistance in Staphylococci by Using a DNA Probe," Antimicrobial Agents and Chemotherapy, 1990, vol. 34 (9), pp. 1720- 1724.

Armstrong P., et al., "Sensitive and Specific Colorimetric Dot Assay to Detect Eastern Equine Encephalomyelitis Viral RNA in Mosquitoes After PCR Amplification," Journal of Medicinal Entomology, 1995, vol. 32 (1), pp. 42-52.

Arnal C., et al., "Quantification of Hepatitis A virus in shellfish by competitive reverse transcription PCRwith coextraction of standard RNA," Applied and Environmental Microbiology, 1999, vol. 65 (1), pp. 322-326.

Aronsson F., et al., "Persistence of the influenza A/WSN/33 virus RNA at midbrain levels of immunodefective mice," Journal of Neurovirology, 2001, vol. 7 (2), pp. 117-124.

Ausubel F.M., et al., eds., Current Protocols in Molecular Biology, vol. 1, John Wiley & Sons Inc., 2004, Table of Contents.

Ausubel F.M., et al., eds., Short Protocols in Molecular Biology: A Compendium of Methods from Current Protocols in Molecular Biology, 2nd Edition, John Wiley & Sons, 1992, Units 2.9, 3.4-3.17, 4.6-4.10, and 10.8.

Ausubel F.M., et al., "Unit 2.11 "Synthesis and Purification of Oligonucleotides," in: Current Protocols in Molecular Biology," 1998, John Wiley & Sons, Inc., pp. 2.11-2.11.21.

Avellon A., et al., "Rapid and Sensitive Diagnosis of Human Adenovirus Infections by a Generic Polymerase Chain Reaction," Journal of Virological Methods, 2001, vol. 92 (2), pp. 113-120.

Azevedo A.M., et al., "Detection of Influenza, Parainfluenza, Adenovirus and Respiratory Syncytial Virus during Asthma Attacks in Children Older than 2 Years Old," Allergologia Immunopathologia, 2003, vol. 31 (6), pp. 311-317.

Baba T., et al., "Genome and Virulence Determinants of High Virulence Community-Acquired MRSA," Lancet, 2002, vol. 359 (9320), pp. 1819-1827.

Bahrmhad A.R., et al., "Polymerise Chain Reaction of Bacterial Genomes with Single Universal Primer: Application to Distinguishing Mycobacteria Species," Molecular and Cellular Probes, 1996, vol. 10 (2), pp. 117-122.

Bahrmhad A.R., et al., "Use of Restriction Enzyme Analysis of Amplified Dna Coding for the hsp65 Gene and Polymerase Chain Reaction with Universal Primer for Rapid Differtiation of Mycobacterium Species in the Clinical Laboratory," Scandinavian Journal of Infectious Diseases, 1998, vol. 30 (5), pp. 477-480.

Bai J., et al., "Matrix-Assisted Laser Desorption/Ionization Mass Spectrometry of Restriction Enzyme-Digested Plasmid DNA Using an Active Nafion Substrate," Rapid Communications in Mass Spectrometry, 1994, vol. 8 (9), pp. 687-691.

Baker G.C., et al., "Review and Re-Analysis of Domain-Specific 16S Primers," Journal of Microbiological Methods, 2003, vol. 55 (3), pp. 541-555.

Banik U., et al., "Multiplex PCR Assay for Rapid Identification of Oculopathogenic Adenoviruses by Amplification of the Fiber and Hexon Genes," Journal of Clincal Microbiology, 2005, vol. 43 (3), pp. 1064-1068.

Barbour A.G., et al., "Identification of an Uncultivatable Borrelia Species in the hard tick Amblyomma Americanum: Possible Agent of a Lyme disease-like illness," The Journal of Infectious Diseases, 1996, vol. 173 (2), pp. 403-409.

Barns S.M., et al., "Detection of Diverse New Francisella-like Bacteria in Environmental Samples," Applied and Environmental Microbiology, 2005, vol. 71 (9), pp. 5494-5500.

Baron E.J., "Genetic Aspects of Methicillin Resistance in Staphylococcus aureus and MethodsUsed for its Detection in Clinical Laboratories in the United States," Journal of Chemotherapy, 1995, vol. 7 (Supl.3), pp. 87-92.

Barr I.G., et al., "An Influenza A(H3) Reassortant Was Epidemic in Australia and New Zealand in 2003," Journal of Medical Virology, 2005, vol. 76 (3), pp. 391-397.

Barski P., et al., "Rapid Assay for Detection of Methicillin-Resistant Staphylococcus Aureus Using Multiplex PCR," Molecular and Cellular Probes, 1996, vol. 10 (6), pp. 471-475.

Bastia T., et al., "Organelle DNA Analysis of Solanum and Brassica Somatic Hybrids by PCR with Universal Primers," Theoretical and Applied Genetics, 2001, vol. 102 (8), pp. 1265-1272.

Batey R.T., et al., "Preparation of Isotopically Labeled Ribonucleotides for Multidimensional NMR Spectroscopy of RNA," Nucleic Acids Research, 1992, vol. 20 (17), pp. 4515-4523.

Baumer A., et al., "Age-Related Human mtDNA Deletions: A Heterogeneous Set of Deletions Arising at aSingle Pair of Directly Repeated Sequences," American Journal of Human Jenetics, 1994, vol. 54 (4), pp. 618-630.

Beall B., et al., "Sequencing emm-Specific PCR Products for Routine andAccurate Typing of Group A Streptococci," Journal of Clincal Microbiology, 1996, vol. 34 (4), pp. 953-958.

Beall B., et al., "Survey of emm Gene Sequences and T-Antigen Types fromSystemic Streptococcus pyogenes Infection Isolates Collected in San Francisco, California; Atlanta, Georgia; and Connecticut in 1994 and 1995," Journal of Clincal Microbiology, 1997, vol. 35 (5), pp. 1231-1235.

Benko, M. et al., "Family Adenoviridae, Virus taxonomy. VIIIth report of the International Committee on Taxonomy of Viruses," 2004, Academic Press, New York, pp. 213-228.

Benson D.A., et al., "GenBank," Nucleic Acids Research, 1999, vol. 27 (1), pp. 12-17.

Benson L.M., et al, "Advantages of Thermococcus kodakaraenis (KOD) DNA polymerase for PCR-mass spectrometry based analyses," American Society for Mass Spectrometry, 2003, vol. 14 (6), pp. 601-604.

Berencsi G., et al., "Molecular Biological Characterization of Adenovirus DNA," Acta Microbiologica et Immunologica Hungarica, 1998, vol. 45 (3-4), pp. 297-304.

Bishop M.J., et al., "Molecular Sequence Databases" in: Nucleic Acid and Protein Sequence Analysis, 4th Chapter, Bishop M.J., et al., eds, IRL Press, 1987, pp. 83-113.

Bisno A.L., Streptococcus Pyogenes in Infectious Diseases and Their Etiologic Agents "Principles and Practice of Infectious Diseases," 1995, vol. 2, pp. 1786-1799.

Black R.M., et al., "Detection of Trace Levels of Tricothecene Mycotoxins in Human Urineby Gas Chromatography-Mass Spectrometry," Journal of Chromatography, 1986, vol. 367 (1), pp. 103-115.

Blaiotta G., et al., "PCR Detection of Staphylococcal Enterotoxin Genes in *Staphyiococcus* Spp. Strains Isolated from Meat and Dairy Products. Evidence for New Variants of seG and Sel in *S. aureus* AB-8802," Journal of Applied Microbiology, 2004, vol. 97 (4), pp. 719-730.

BLAST Search results, Mar. 7, 2006.

Boivin-Jahns V., et al., "Bacterial Diversity in a Deep-Subsurface Clay Environment," Applied and Environmental Microbiology, 1996, vol. 62 (9), pp. 3405-3412.

Bolton E.T., et al., "A general method for the isolation of RNA complementary to DNA," Proceedings of the National Academy of Sciences of the USA, 1962, vol. 48, pp. 1390-1397.

Bonk T., et al., "Matrix-Assisted Laser Desorption/Ionization Time-of-Flight Mass Spectrometry-Based Detection of Microsatellite Instabilities in Coding DNA Sequences: A Novel Approach to Identify DNA-Mismatch Repair-Deficient Cancer Cells," Clinical Chemistry, 2003, vol. 49 (4), pp. 552-561.

Borrow R., et al., "SiaD PCR Elisa for Confirmation and Identification of Serogroup Y and W135 Meningococcal Infections," FEMS Microbiology Letters, 1998, vol. 159 (2), pp. 209-214.

Boubaker K., et al., "Panton-Valentine Leukocidin and Staphylococcal Skin Infections in Schoolchildren," Emerging Infectious Diseases, 2004, Vol. 10 (1), pp. 121-124.

Bowen J.E., et al., "The Native Virulence Plasm id Combination Affects the Segregational Stability of a Thetareplicating Shuttle Vector in Bacillus Anthracis Var," Journal of Applied Microbiology, 1999, vol. 87 (2), pp. 270-278.

Bowers K.M., et al., "Screening for Methicillin Resistance in Staphylococars Aureus and Coagulasenegative Staphylococci: Evaluation of Three Selective and MastalexMRSA latex Agglutination," British Journal of Biomedical Science, 2003, vol. 60 (2), pp. 71-74.
Brakstad O.G., et al., "Direct Identification of Staphylococcus Aureus in Blood Cultures Bydetection of the Gene, Encoding the Thermostable Nuclease or the Gene Product," Acta Pathologica, Microbiologica et Immunologica Scandinavica, 1995, vol. 103 (3), pp. 209-218.
Brakstad O.G., et al., "Multiplex Polymerase Chain Reaction for Detection of Genes for *Staphylococcus aureus* Themonuclease and Methicillin Resistance and Correlation with Oxacillin Resistance," Acta Pathologica, Microbiologica et Immunologica Scadinavica, 1993, vol. 101 (9), pp. 681-688.
Brandt C.D., et al., "Infections in 18,000 Infants and Children in a Controlled Study of Respiratory Tract Disease. I. Adenovirus Pathogenicity in Relation to Serologic Type and Illness Syndrome," American Journal of Epidemiology, 1969, vol. 90 (6), pp. 484-500.
Brayshaw D.P., "Methicillin-Resistant Staphylococcus Aureus: Evaluation of Detection Techniques on Laboratory-Passaged Organisms," British Journal of Biomedical Science, 1999, vol. 56 (3), pp. 170-176.
Brightwell G., et al., "Development of Internal Controls for PCR Detection of Bacillus Anthracis," Molecular and Cellular Probes, 1998, vol. 12 (6), pp. 367-377.
Brightwell G., et al., "Genetic Targets for the Detection and Identifiaction of Venezuelan Equine Encephalitis Viruses," Archives of Virology, 1998, vol. 143 (4), pp. 731-742.
Bronzoni R.V.M., et al., "Duplex Reverse Transcription-PCR Followed by Nested Pcr Assays for Detection and Identification of Brazilian Alphaviruses and Flaviviruses," Journal of Clincal Microbiology, 2005, vol. 43 (2), pp. 696-702.
Bronzoni R.V.M., et al., "Multiplex Nested PCR for Brazilian Alphavirus Diagnosis," Transactions of the Royal Society of Tropical Medicine and Hygiene, 2004, vol. 98 (8), pp. 456-461.
Brown I.H., "Advances in Molecular Diagnostics for Avian Influenza," Developments in Biologicals, 2006, vol. 124, pp. 93-97.
Brownstein M.J., et al., "Modulation of Non-Templated Nucleotide Addition by Taq DNA Polymerase: Primer Modifications that Facilitate Genotyping," BioTechniques, 1996, vol. 20 (6), pp. 1004-1010.
Brunaud V., et al., "T-DNA Integration into the Arabidopsis Genome Depends on Sequence of Pre-Insertion Sites," EMBO Reports, 2002, vol. 3 (12), pp. 1152-1157.
Buetow K.H., et al., "High-Throughput Development and Characterization of a Genomewide Collection of Gene-Based Single Nucleotide Polymorphism Markers by Chip-Based Matrix-Assisted Laser Desorption/lonization Time-of-Flight Mass Spectrometry," Proceedings of the National Academy of Sciences, 2001, vol. 98 (2), pp. 581-584.
Butel J.S., et al., "Cell and Molecular Biology of Simian Virus 40: Implications for Human Infections and Disease," Journal of the National Cancer Institute, 1999, vol. 91 (2), pp. 119-134.
Butler J., "DNA Profiling and Quantitation of Human DNA," CCQM Bio Analysis Working Group, 2005.
Campbell W.P., et al., "Detection of California serogroup Bunyavirus in tissue culture and mosquito pools by PCR," Journal of Virological Methods, 1996, vol. 57 (2), pp. 175-179.
Carracedo A., et al., "DNA Commission of the International Society for Forensic Genetics: Guidelines Formitochondrial DNA Typing," Forensic Science International, 2000, vol. 110 (2), pp. 79-85.
Carroll K.C., et al., "Rapid Detection of the Staphylococcal mecA Gene from Bactec BloodCulture Bottles by the Polymerase Chain Reaction," American Journal of Clincal Pathology, 1996, vol. 106 (5), pp. 600-605.
Case J.T., et al., "Maternal Inheritance of Mitochondria! DNA Polymorphisms in Cultured Human Fibroblasts," Somatic Cell Genetics, 1981, vol. 7 (1), pp. 103-108.
Cattoli G., et al., "Comparison of Three Rapid Detection Systems for Type A Influenza Virus on Tracheal Swabs of Experimentally and Naturally Infected Birds," Avian Pathology, 2004, vol. 33 (4), pp. 432-437.
Cavassini M., et al., "Evaluation of MRSA-Screen, a Simple Anti-PBP 2a Slide Latex AgglutinationKit, for Rapid Detection of Methicillin Resistance in *Staphylococcus aureus,*" Journal of Clincal Microbiology, 1999, vol. 37 (5), pp. 1591-1594.
Certificate of Correction mailed Jan. 6, 2009 for U.S. Appl. No. 10/660,996, filed Sep. 12, 2003.
Certificate of Correction mailed Aug. 7, 2007 for U.S. Appl. No. 10/660,997, filed Sep. 12, 2003.
Certificate of Correction mailed Dec. 12, 2006 for U.S. Appl. No. 10/156,608, filed May 24, 2002.
Certificate of Correction mailed Jul. 17, 2007 for U.S. Appl. No. 09/891,793, filed Jun. 26, 2001.

Certificate of Correction mailed Mar. 31, 2008 for U.S. Appl. No. 09/891,793, filed Jun. 26, 2001.
Certificate of Correction mailed Mar. 31, 2008 for U.S. Appl. No. 10/156,608, filed May 24, 2002.
Certificate of Correction mailed Mar. 31, 2008 for U.S. Appl. No. 10/660,997, filed Sep. 12, 2003.
Cespedes A., et al., "Polymerase Chain Reaction-Restriction Fragment Length Polymorphism Analysis of a Short Fragment of the Cytochrome b Gene for Identification of Flatfish Species," Journal of Food Protection, 1998, vol. 61 (12), pp. 1684-1685.
Chamberlin M., et al., "New RNA Polymerase from *Escerichia coli* Infected with Bacteriophage T7," Nature, 1970, vol. 228 (5268), pp. 227-231.
Chandra S., et al., "Virus Reduction in the Preparation and Intravenous Globulin: In Vitro Experiments," Transfusion, 1999, vol. 39 (3), pp. 249-257.
Chang P.K., et al., "afIT, a MFS Transporter-Encoding Gene Located in the Aflatoxin Gene Cluster, does not have a Significant Role in Aflatoxin Secretion," Fungal Genetics and Biology, 2004, vol. 41 (10), pp. 911-920.
Chaves F., et al., "Molecular Characterization of Resistance to Mupirocin in Methicillin—Susceptible and -Resistant Isolates of Staphylococcus aureus from Nasal Samples," Journal of Clincal Microbiology, 2004, vol. 42 (2), pp. 822-824.
Chelly J., et al., "Transcription of the Dystrophin Gene in Human Muscle and Non-Muscle Tissue," Nature, 1988, vol. 333 (6176), pp. 858-860.
Chen C.A., et al., "Universal Primers for Amplification of Mitochondria! small Subunit Ribosomal RNA-Encoding Gene in Scleractinian Corals," Marine Biotechnology, 2000, vol. 2 (2), pp. 146-153.
Chen C.H., et al., Laser Desorption Mass Spectrometry for FastDNA Sequencing [online], Nov. 1994, Retrieved from the Internet< URL:http://www.ornl.gove/sci/techresources/Human_Genome/publicat/94SANTA/sequencing/seqtoc.shtml>.
Chen J., et al., "A universal PCR Primer to Detect Members of the Potyviridae and its use to Examine the Taxonomic Status of Several Members of the Family," Archives of Virology, 2001, vol. 146 (4), pp. 757-766.
Chen N., et al., "The Genomic Sequence of Ectromelia Virus, the Causative Agent of Mousepox," Virology, vol. 317 (1), pp. 165-186.
Chen R., et al., "Trapping, Detection, and Charge and Mass Measurement of Large Individual Ions (up to 1.1 X 108 Daltons) by Electrospray Ionization FTICR MS," 42nd ASMS Conference on Mass Spectrometry, 1994.
Chen Y.Z., et al., "A BAC-Based STS-Content Map Spanning a 35-Mb Region of Human Chromosome 1p35-36," Genomics, 2001, vol. 74 (1), pp. 55-70.
Chen Z., et al., "Genetic Mapping of the Cold-Adapted Phenotype of B/Ann Arbor/1/66, the Master Donor Virus for Live Attenuated Influenza Vaccines (FluMist)," Virology, 2006, vol. 345 (2), pp. 416-423.
Chiu N. H., et al., "Mass Spectrometry of Single-Stranded Restriction Fragments Captured by an Undigested Complementary Sequence," Nucleic Acids Research, 2000, vol. 28 (8), pp. E31.
Chmielewicz B., et al., "Development of a PCR-Based Assay for Detection, Quantification, and Genotyping of Human Adenoviruses," Clinical Chemistry, 2005, vol. 51 (8), pp. 1365-1373.
Cho M., et al., "Application of the Ribonuclease P (RNaseP) RNA Gene Sequence for Phylogenetic Analysis of the Genus Saccharomonospora," International Journal of Systematic Bacteriology, 1998, vol. 48 (4), pp. 1223-1230.
Choi S., et al., "Real-Time PCR Quantification of Human Adenoviruses in Urban Rivers Indicates Genome Prevalence but Low Infectivity," Applied and Environmental Microbiology, 2005, vol. 71 (11), pp. 7426-7433.
Choi Y.K., et al., "Detection and Subtying of Swine Influenza H1N1, H1 N2 and H3N2 Viruses in Clinical Samples Using Two Multiplex RT-PCR Assays," Journal of Virological Methods, 2002, vol. 102 (1-2), pp. 53-59.
Christel L.A., et al., "Rapid, Automated Nucleic Acid Probe Assays Using Silicon Microstructures forNucleic Acid Concentration," Journal of Biomechanical Engineering, 1999, vol. 121 (1), pp. 22-27.

Claas E.C., et al., "Internally Controlled Real-Time PCT Monitoring of Adenovirus Dna Load inSerum or Plasma of Transplant Recipients," Journal of Clincal Microbiology, 2005, vol. 43 (4), pp. 1738-1744.
Cloney L., et al., "Rapid Detection of mecA in Methicillin Resistant *Staphylococcus aureus* Using Cycling Probe Technology," Molecular and Cellular Probes, 1999, vol. 13 (13), pp. 191-197.
Collins D.W., et al., "Numerical Classification of Coding Sequences," Nucleic Acids Research, 1992, vol. 20 (6), pp. 1405-1410.
Conrads G., et al., "16S-23S rDNA Internal Transcribed Spacer Sequences for Analysis of the Phylogenetic Relationships Among Species of the Genus Fusobacterium," International Journal of Systematic and Evolutionary Microbiology, 2002, vol. 52 (2), pp. 493-499.
Contreras-Salazar B., et al., "Up Regulation of the Epstein-Barr Virus (EBV)-Encoded Membrane Protein Lmp in the Burkitt's Lymphoma Line Daudi after Exposure to N-Butyrate and after EBV Superinfection," Journal of Virology, 1990, vol. 64 (11), pp. 5441-5447.
Co-pending U.S. Appl. No. 10/318,463.
Co-pending U.S. Appl. No. 10/318,681.
Co-pending U.S. Appl. No. 10/323,186.
Co-pending U.S. Appl. No. 10/323,187.
Co-pending U.S. Appl. No. 10/324,721.
Co-pending U.S. Appl. No. 10/521,662.
Co-pending U.S. Appl. No. 10/754,415.
Co-pending U.S. Appl. No. 10/807,019.
Co-pending U.S. Appl. No. 10/845,052.
Co-pending U.S. Appl. No. 10/964,571.
Co-pending U.S. Appl. No. 11/209,439.
Co-pending U.S. Appl. No. 11/674,538.
Co-pending U.S. Appl. No. 11/682,259.
Co-pending U.S. Appl. No. 11/929,910.
Co-pending U.S. Appl. No. 11/930,108.
Co-pending U.S. Appl. No. 11/930,741.
Co-pending U.S. Appl. No. 90/010,209.
Co-pending U.S. Appl. No. 90/010,210.
Co-pending U.S. Appl. No. 90/010,447.
Co-pending U.S. Appl. No. 90/010,448.
Co-pending U.S. Appl. No. 60/639,068, filed Dec. 22, 2004.
Co-pending U.S. Appl. No. 60/648,188, filed Jan. 28, 2005.
Cornel A.J., et al., "Polymerase Chain Reaction Species Diagnostic Assay for Anopheles Quadrimaculatus Cryptic Species (Diptera:Culicidae) Based on Ribosomal DNA ITS2 Sequences," Journal of Medical Entomology, 1996, vol. 33 (1), pp. 109-116.
Couto I., et al., "Development of Methicillin Resistance in Clinical Isolates of Staphylococcus Sciuri by Transcriptional Activation of the mecA Homologue Native to the Species," Journal of Bacteriology, 2003, vol. 185 (2), pp. 645-653.
Crain P.F., et al., "Applications of Mass Spectrometry to the Characterization of Oligonucleotides and Nucleic Acids," Annual Biochemistry, 1998, vol. 9 (1), pp. 25-34.
Crawford-Miksza L., et al., "Analysis of 15 Adenovirus Hexon Proteins Reveals the Location and Structure of Seven Hypervariable Regions Containing Serotype-Specific Residues," Journal of Virology, 1996, vol. 70 (3), pp. 1836-1844.
Crawford-Miksza L.K., et al., "Adenovirus Serotype Evolution is Driven by Illegitimate Recombination in the Hypervariable Regions of the Hexon Protein," Virology, 1996, vol. 224 (2), pp. 357-367.
Crawford-Miksza L.K., et al., "Strain Variation in Adenovirus Serotypes 4 and 7a Causing Acute Respiratory Disease," Journal of Clincal Microbiology, 1999, vol. 37 (4), pp. 1107-1112.
Crespillo M., et al., "Mitochondrial DNA Sequences for 118 Individuals from Northeastern Spain," International Journal of Legal Medicine, 2000, vol. 114 (1-2), pp. 130-132.
Cui L., et al., "Contribution of a Thickened Cell Wall and Its Glutamine Nonamidated Component to the Vancomycin Resistance Expressed by *Staphylococcus aureus* Mu50," Antimicrobial Agents and Chemotherapy, 2000, vol. 44 (9), pp. 2276-2285.
Dasen G., et al., "Classification and Identification of Propiolbacteria based on Ribosomal RNA Genes and Pcr," Systematic and Applied Microbiology, 1998, vol. 21 (2), pp. 251-259.

De Jong J.C., et al., "Adenoviruses from Human Immunodeficiency Virus-Infected Individuals,Including Two Strains That Represent New Candidate Serotypes Ad50 and Ad51 of Species B1 and D, Respectively," Journal of Clincal Microbiology, 1999, vol. 37 (12), pp. 3940-3945.

De La Puente-Redondo V.A., et al., "Comparison of Different PCR Approaches for Typing of Francisella Tularensis Strains," Journal of Clinical Microbiology, 2000, vol. 38 (3), pp. 1016-1022.

Deforce D.L.D., et al., "Characterization of DNA Oligonudeotides by Coupling of Capillary zone Electrophoresis to Electrospray Ionization Q-TOF Mass Spectrometry," Analytical Chemistry, 1998, vol. 70 (14), pp. 3060-3068.

Deforce D.L.et al., "Analysis of Oligonucleotides by ESI-MS," Advances in Chromatography (New York), 2000, vol. 40, pp. 539-566.

Del Blanco Garcia N., et al., "Genotyping of Francisella Tularensis Strains by Pulsed-field gel Electrophoresis, Amplified Fragment Length Polymorphism Fingerprinting, and 16S rRNA gene Sequencing," Journal of Clinical Microbiology, 2002, vol. 40 (8), pp. 2964-2972.

Del Vecchio V.G., et al., "Molecular Genotyping of Methicillin-Resistant *Staphylococcus aureus* via Fluorophore-Enhanced Repetitive-Sequence PCR," Journal of Clincal Microbiology, 1995, vol. 33 (8), pp. 2141-2144.

Demesure B., et al., "A set of Universal Primers for Amplification of Polymorphic Non-coding Regions of Mitochondrial and Chioroplast DNA in plants," Molecular Ecology, 1995, vol. 4, pp. 129-131.

Denis M., et al., "Development of a Semiquantitative PCR Assay Using Internal Standard and Colorimetricdetection on Microwell Plate for Pseudorabies Virus," Molecular and Cellular Probes, 1997, vol. 11 (6), pp. 439-448.

Deurenberg R.H., et al., "Rapid Detection of Panton-Valentine Leukocidin from Clinical Isolates of *Staphylococcus aureus* Strains by Real-Time PCR," FEMS Microbiology Letters, 2004, vol. 240 (2), pp. 228-228.

Deurenberg R.H., et al., "The Prevalence of the *Staphylococcus aureus* tst Gene among Community- and Hospital-Acquired Strains and Isolates from Wegener's Granulomatosis Patients," FEMS Microbiology Letters, 2005, vol. 245 (1), pp. 185-189.

Di Guilmi A.M., et al., "Human Adenovirus Serotype 3 (Ad3) and the Ad3 fiber Protein Bind to a 130-kDa Membrane Protein on HLa Cells," Virus Research, 1995, vol. 38 (1), pp. 71-81.

Dias Neto E., et al., "Shotgun Sequencing of the Human Transcriptome with ORF Expressed Sequence Tags," Proceedings of the National Academy of Sciences, 2000, vol. 97 (7), pp. 3491-3496.

Diep B.A., et al., "Complete Genome Sequence of USA300, an Epidemic Clone of Community Acquired Meticillin-Resistant Staphylococcus Aureus," Lancet, 2006, vol. 367 (9512), pp. 731-739.

Dinauer D.M., et al., "Sequence-based typing of HLA class II DQB1," Tissue Antigens, 2000, vol. 55 (4), pp. 364-368.

Ding C., et al., "A High-Throughput Gene Expression Analysis Technique using Compettiive PCR and Matrixassisted Laser Desorption Ionization time-of-Flight MS," Proceedings of the National Academy of Sciences, 2003, vol. 100 (6), pp. 3059-3064.

Donehower L.A., et al., "The Use of Primers from Highly Conserved Pol Regions to Identify Uncharacterized Retroviruses by the Polymerase Chain Reaction," Journal of Virological Methods, 1990, vol. 28 (1), pp. 33-46.

Donofrio J.C.et al., "Detection of Influenza A and B in Respiratory Secretions with the Polymerase Chain Reaction," PCR Methods and Applications, 1992, vol. 1 (4), pp. 263-268.

Doty P., et al., "Strand Separation and Specific Recombination in Deoxyribonucleic Acids: Physical Chemical Studies," Proceedings of the National Academy of Sciences of USA, 1960, vol. 46 (4), pp. 461-476.

Drosten C., et al., "Identification ofa Novel Coronavirus in Patients with Severe Acute Respiratory Syndrome," New England Journal of Medicine, 2003, vol. 348 (20), pp. 1967-1976.

Dubernet S., et al., "A PCR-based Method for Identification of *Lactobacilli* at to Genus Level," FEMS Microbiology Letter, 2002, vol. 43 (7), pp. 3049-3053.

Ebner K., et al., "Molecular Detection and Quantitative Analysis of the Entire Spectrum of Human Adenoviruses by a Two-Reaction Real-Time PCR Assay," Journal of Clinical Microbiology, 2005, vol. 43 (7), pp. 3049-3053.

Ebner K., et al., "Typing of Human Adenoviruses in Specimens from Immunosuppressed Patients by PCR-Fragment Length Analysis and Real-Time Quantitative PCR," Journal of Clinical Microbiology, 2006, vol. 44 (8), pp. 2808-2815.

Echavarria M., et al., "Detection of Adenoviruses (AdV) in Culture-Negative EnvironmentalSamples by PCR During an AdV-Associated Respiratory Disease Outbreak," Journal of Clinical Microbiology, 2000, vol. 38 (8), pp. 2982-2984.

Echavarria M., et al., "PCR Method for Detection of Adenovirus in Urine of Healthy and Human Immunodeficiency Virus-Infected Individuals," Journal of Clinical Microbiology, 1998, vol. 36 (11), pp. 3323-3326.

Echavarria M., et al., "Prediction of Severe Disseminated Adenovirus Infection by Serum PCR," Lancet, 2001, col. 358 (9279), pp. 384-385.

Echavarria M., et al., "Rapid Detection of Adenovirus in Throat Swab Specimens by PCR DuringRespiratory Disease Outbreaks among Military Recruits," Journal of Clinical Microbiology, 2003, vol. 41 (2), pp. 810-812.

Echavarria M., et al., "Use of PCR to Demonstrate Presence of Adenovirus Species B, C, or F as Well as Coinfection with Two Adenovirus Species in Children with Flu-Like Symptoms," Journal of Clinical Microbiology, 2006, vol. 44 (2), pp. 625-627.

Ecker D. J., et al., "Rapid Identification and Strain-Typing of Respiratory Pathogens for Epidemic Surveillance," Proceedings of the National Academy of Sciences, 2005, vol. 102 (22), pp. 8012-8017.

Ecker D. J., et al., "The Ibis T5000 Universal Biosensor. An Automated Platform for Pathogen Identification and Strain Typing," Journal of the Association for Laboratory Automation, 2006, vol. 11 (6), pp. 341-351.

Ecker D.J., et al., "Ibis T5000: a universal biosensor approach for microbiology," Nature Reviews Microbiology, 2008, vol. 6 (7), pp. 553-558.

Edwards K.M., et al., "Adenovirus Infections in Young Children," Pediatrics, 1985, vol. 76 (3), pp. 420-424.

Ellis J. S., et al., "Molecular Diagnosis of Influenza," Reviews in Medical Virology, 2002, vol. 12 (6), pp. 375-389.

Ellis J.S., et al., "Multiplex Reverse Transcription-PCR for Surveillance of Influenza a and B Viruses in England and Wales in 1995 and 1996," Journal of Clinical Microbiology, 1997, vol. 35(8), pp. 2076-2082.

Elnifro E.M., et al., "PCR and Restriction Endonuclease Analysis for Rapid Identification of Adenovirus Subgenera," Journal of Clinical Microbiology, 2000, vol. 38 (6), pp. 2055-2061.

Elsayed S., et al., "Development and Validation of a Molecular Beacon Probe-Based Real-Time Polymerase Chain Reaction Assay for Rapid Detection of Methicillin Resistance in *Staphylococcus aureus*," Archives of pathology and laboratory medicine, 2003, vol. 127 (7), pp. 845-849.

EMBL "*Arabidopsis thaliana* T-DNA flanking sequence, left border, clone 346C06," Accession No. AJ552897, Mar. 29, 2003.

EMBL "Dog (Clone: CXX.147) primer for STS 147, 3' end, sequence tagged site," Accession No. L15697, Mar. 4, 2000.

EMBL "Human, muscle, Mitochondrial Mutant, 22 nt, segment 2 of 2," Accession No. S90302, Sep. 1, 2004.

EMBL, "Sequence 10 from patent US 6563025," Accession No. AR321656, Aug. 18, 2003.

EMBL "Synthetic Construct DNA, Reverse Primer for Human STS sts-AA031654 at 1p36" Accession No. AB068711, May 21, 2003.

Enright M.C., et al., "A multilocus sequence typing scheme for *Streptococcus pneumoniae*: identification of clones associated with serious invasive disease," Microbiology, 1998, vol. 144 (Pt 11), pp. 3049-3060.

Enright M.C., et al., "Multilocus Sequence Typing for Characterization of Methicillin-Resistant and Methicillin-Susceptible Clones of *Staphylococcus aureus*," Journal of Clinical Microbiology, 2000, vol. 38(3), pp. 1008-1015.

Enright M.C., et al., "Multilocus Sequence Typing of *Streptococcus pyogenes* and theRelationships between Emm Type and Clone," Infection and Immunity, 2001, vol. 69 (4), pp. 2416-2427.

Enright M.C., et al., "The Evolutionary History of Methicillin-Resistant *Staphylococcus aureus*(MRSA)," Proceedings of the National Academy of Sciences of USA, 2002, vol. 99 (11), pp. 7687-7692.

Enright M.C., "The Evolution of a Resistant Pathogen—the Case of MRSA," Current Opinion inPharmacology, 2003, vol. 3 (5), pp. 474-479.

Eremeeva M.E., et al., "Evaluation of a PCR Assay for Quantitation of Rickettsia rickettsii and Closely Related Spotted Fever Group Rickettsiae," Journal of Clinical Microbiology, 2003, vol. 41 (12), pp. 5466-5472.

Erlich H.A., ed., PCR Technology: Principles and Applications for DNA Amplification, W.H. Freeman and Company, 1989.

Esmans E.L., et al., "Liquid Chromatography-Mass Spectrometry in Nucleoside, Nucleotide and Modified Nucleotide Characterization," Journal of Chromatography, 1998, vol. 794, pp. 109-127.

Eugene-Ruellan G., et al., "Detection of Respiratory Syncytial Virus A and B and Parainfluenzavirus 3 Sequences in Respiratory Tracts of Infants by a Single PCR with Primers Targeted to the L-Polymerase Gene and Differential Hybridization," Journal of Clinical Microbiology, 1998, vol. 36 (3), pp. 796-801.

Evans P., et al., "Practical Algorithms for Universal DNA Primer Design: An Exercise in Algorithm Engineering," Currents in Computational Molecular Biology, 2001, Les Publications CRM, pp. 25-26.

Ex Parte Re-Examination Certificate for U.S. Appl. No. 90/010,209 mailed Jul. 7, 2009.

Ex Parte Re-Examination Certificate for U.S. Appl. No. 90/010,210, mailed Dec. 28, 2010.

Ex Parte Re-Examination Certificate for U.S. Appl. No. 90/010,447 mailed Feb. 15, 2011.

Examiner Interview Summary mailed Oct. 3, 2005 for U.S. Appl. No. 10/326,046, filed Dec. 18, 2002.

Examiner Interview Summary mailed Nov. 6, 2008 for U.S. Appl. No. 10/728,486, filed Dec. 5, 2003.

Examiner Interview Summary mailed Oct. 24, 2008 for U.S. Appl. No. 11/582,859, filed Oct. 17, 2006.

Examiner Interview Summary mailed Feb. 27, 2006 for U.S. Appl. No. 10/326,644, filed Dec. 18, 2002.

Examiner Interview Summary mailed Jan. 27, 2006 for U.S. Appl. No. 10/323,211, filed Dec. 18, 2002.

Examiner Interview Summary mailed May 28, 2008 for U.S. Appl. No. 10/660,998, filed Sep. 12, 2003.

Examiner Interview Summary mailed Oct. 28, 2008 for U.S. Appl. No. 11/331,987, filed Jan. 13, 2006.

Examiner Interview Summary mailed Oct. 29, 2008 for U.S. Appl. No. 11/331,978, filed Jan. 13, 2006.

Examiner Interview Summary mailed Jul. 31, 2006 for U.S. Appl. No. 10/326,643, filed Dec. 18, 2002.

Examiner Interview Summary Record mailed Oct. 29, 2009 for U.S. Appl. No. 10/660,122, filed Sep. 11, 2003.

Examiner Interview Summary Report mailed May 19, 2003 for U.S. Appl. No. 09/891,793, filed Jun. 26, 2001.

Facklam R., et al., "Emm Typing and Validation of Provisional M Types for Group A *Streptococci*," Emerging Infectious Diseases, 1999, vol. 5 (2), pp. 247-253.

Fang H., et al., "Rapid Screening and Identification of Methicillin-Resistant *Staphylococcus aureus* from Clinical Samples by Selective-Broth and Real-Time PCR Assay," Journal of Clinical Microbiology, 2003, vol. 41 (7), pp. 2894-2899.

Farlow J., et al., "Francisella Tularensis Strain Typing Using Multiple-Locus, Variable-Number Tandem Repeat Analysis," Journal of Critical Microbiology, 2001, vol. 39 (9), pp. 3186-3192.

Farrell D. J., "The Reliability of Microscan Conventional and Rapid Panels to Identify *Staphylococcus aureus* and Detect Methicillin Resistance: An Evaluation Using the Tube Coagulase Test and mecA PCR," Pathology, 1997, vol. 29 (4), pp. 406-410.

Fedele C.G., et al., "Multiplex Polymerase Chain Reaction for the Simultaneous Detection and Typing of Polyomavirus JC, BK and SV40 DNA in Clinical Samples," Journal of Virological Methods, 1999, vol. 82 (2), pp. 137-144.

Fedele C.G., et al., "Quantitation of Polyomavirus DNA by a Competitive Nested Polymerase Chain Reaction," Journal of Virological Methods, 2000, vol. 88 (1), pp. 51-61.

Feng P., "Impact of Molecular Biology on the Detection of Food Pathogens," Molecular Biotechnology, 1997, vol. 7 (3), pp. 267-278.

Figueiredo L.M., et al., "Identification of Brazilian Flavivirus by a simplified reverse transcription-polymerase chain reaction method using Flavivirus universal primers," American Journal of Tropical Medicine and Hygiene, 1998, vol. 59 (3), pp. 357-362.

Final Office Action mailed Aug. 6, 2010 for U.S. Appl. No. 11/929,910, filed Oct. 30, 2007.

Final Office Action mailed Jul. 8, 2010 for U.S. Appl. No. 12/326,800, filed Dec. 2, 2008.

Final Office Action mailed May 12, 2010 for U.S. Appl. No. 11/674,538, filed Feb. 13, 2007.

Final Office Action mailed Nov. 17, 2009 for U.S. Appl. No. 11/582,875, filed Oct. 17, 2006.

Final Office Action mailed Feb. 18, 2010 for U.S. Appl. No. 10/754,415, filed Jan. 9, 2004.

Final Office Action mailed Nov. 20, 2009 for U.S. Appl. No. 11/331,987, filed Jan. 13, 2006.

Final Office Action mailed Jun. 23, 2010 for U.S. Appl. No. 11/930,017, filed Oct. 30, 2007.

Final Office Action mailed Feb. 26, 2009 for U.S. Appl. No. 11/582,863, filed Oct. 17, 2006.

Final Office Action mailed Jan. 30, 2009 for U.S. Appl. No. 10/844,938, filed May 12, 2004.

Final Rejection mailed Oct. 14, 2009 for U.S. Appl. No. 10/943,344, filed Sep. 17, 2004.

Flora J.W., et al, "Dual-Micro-ESI Source for Precise Mass Determination on a Quadrupole time-of-Flight Mass Spectrometer for Genomic and Proteomic Applications," Annual Biochemistry, 2002, vol. 373 (7), pp. 538-546.

Fong W.K., et al., "Rapid Solid-Phase Immunoassay for Detection of Methicillin-Resistant*Staphylococcus aureus* Using Cycling Probe Technology," Journal of Clinical Microbiology, 2000, vol. 38 (7), pp. 2525-2529.

Fox A., et al., "Identification and Detection of Bacteria: Electrospray MS-MS Versus Derivatization/GC-MS," Proceedings of the ERDEC Scientific Conference on Chemical and Biological Defense Research, Aberdeen Proving Ground, MD, Nov. 15-18, 1994, pp. 39-44.

Fox A.,et al., "Report of the Bioterrorism Workshop," Journal of Microbiological Methods, 2002, vol. 51 (3), pp. 247-254.

Fox J.P., et al., "The Virus Watch Program: A Continuing Surveillance of Viral Infections in Metropolitan New York Families," American Journal of Epidemiology, 1969, vol. 89 (1), pp. 25-50.

Fox K.F., et al., "Identification of Brucella by ribosomal-spacer-region Pcr and differentiation of Brucell canis from other *Brucella* spp. pathogenic for humans by carbohydrate profiles," Journal of Clinical Microbiology, 1998, vol. 36 (11), pp. 3217-3222.

Francois J-C., et al., "Sequence-Specific Recognition and Cleavage of Duplex DNA via Triple-Helix Formation by Oligonucleotides Covalently Linked to a Phenanthroline-Copper Chelate," Proceedings of the National Academy of Sciences of USA, 1989, vol. 86 (24), pp. 9702-9706.

Francois P., et al., "Rapid Detection of Methicillin-Resistant *Staphylococcus aureus* Directly from Sterile or Nonsterile Clinical Samples by a New Molecular Assay," Journal of Clinical Microbiology, 2003, vol. 41 (1), pp. 254-260.

Fraser C.M., et al., "The Mimimal Gene Complement of *Mycoplasma genitalium*," Science, 1995, vol. 270 (5235), pp. 397-403.

Freiberg C., et al., "Genome-Wide mRNA Profiling: Impact on Compound Evaluation and Target Identification in Anti-Bacterial Research," Targets, 2002, vol. 1 (1), pp. 20-29.

Freymuth F., et al., "Comparison of Multiplex PCR Assays and Conventional Techniques for the Diagnostic of Respiratory Virus Infections in Children Admitted to Hospital With an Acute Respiratory Illness," Journal of Medical Virology, 2006, vol. 78 (11), pp. 1498-1504.

Freymuth F., et al., "Detection of Respiratory Syncytial Virus, Parainfluenzavirus 3, Adenovirus Andrhinovirus Sequences in Respiratory Tract of Infants by Polymerase Chain Reaction and Hybridization," Clinical and Diagnostic Virology, 1997, vol. 8 (1), pp. 31-40.

Fuerstenau S.D., et al., "Molecular Weight Determination of Megadalton DNA Electrospray Ions Using Charge Detection Time-of-flight Mass Spectrometry," Rapid Communications in Mass Spectrometry, 1995, vol. 9 (15), pp. 1528-1538.

Fujimoto T., et al., "Single-Tube Multiplex. PCR for Rapid and Sensitive Diagnosis of Subgenus B and Other Subgenera Adenoviruses in Clinical Samples," Microbiology and Immunology, 2000, vol. 44 (10), pp. 821-826.

Fujimura S., et al., "Characterization of the mupA Gene in Strains of Methicillin-Resistant *Staphylococcus aureus* with a Low Level of Resistance to Mupirocin," Antimicrobial Agents and Chemotheraphy, 2001, vol. 45 (2), pp. 641-642.

Fujimura S., et al., "Isoleucyl-tRNA Synthetase Mutations in *Staphylococcus aureus* Clinicallsolates and In Vitro Selection of Low-Level Mupirocin-Resistant Strains," Antimicrobial Agents and Chemotheraphy, 2003, vol. 47 (10), pp. 3373-3374.

Fujioka S., et al., "Analysis of Enterovirus Genotypes using Single-Strand Conformation Polymorphisms of Polymerase Chain Reaction Product," Journal of Virological Methods, 1995, vol. 51 (2-3), pp. 253-258.

Gabriel M.N., et al., "Improved mtDNA Sequence Analysis of Forensic Remains using a "Mini-Primer Set" Amplification Strategy," Journal of Forensic Sciences, 2001, vol. 46 (2), pp. 247-253.

Gall J. G. D., et al., "Construction and Characterization of Hexon-Chimeric Adenoviruses: Specification of Adenovirus Serotype," Journal of Virology, 1998, vol. 72 (12), pp. 10260-10264.

Gammelin M., et al., "Two Subtypes of Nucleoproteins (NP) of Influenza a Viruses," Virology, 1989, vol. 170 (1), pp. 71-80.

Garcia S., et al., "Quantitative Real-Time PCR Detection of Rift Valley Fever Virus and Its Application to Evaluation of Antiviral Compounds," Journal of Clinical Microbiology, 2001, vol. 39 (12), pp. 4456-4461.

Garcia-Martinez J., et al., "Use of the 16s-23s Ribosomal Genes Spacer Region in Studies of Prokaryotic Diversity," Journal of Microbiological Methods, 1999, vol. 36 (1-2), pp. 55-64.

Gattermann N., et al., "Heteroplasmic Point Mutations of Mitochondria! DNA Affecting Subunit I of Cytochrome c Oxidise in Two Patients with Acquired Idiopathic Siderblastic Anemia," Blood, 1997, vol. 90 (12), pp. 4961-4972.

Gaydos C.A., et al., "Adenovirus Vaccines in the U.S. Military," Military Medicine, 1995, vol. 160 (6), pp. 300-304.

Geha D.J., et al., "Multiplex PCR for Identification of Methicillin-Resistant *Staphylococci* in the Clinical Laboratory," Journal of Clinical Microbiology, 1994, vol. 32 (7), pp. 1768-1772.

Genbank, "{Deletion 6} [Human, Muscle, Mitochondrial Mutant, 22 nt, Segment 2 of 2]," Accession No. S90302.1, Jun. 10, 1992.

Genbank "Acinetobacter genomosp. 10 strain CIP 70.12 RNA polymerase subunit B (rpoB) gene, complete cds," Accession No. 78099429, Mar. 11, 2006.

Genbank, "Bovine parainfluenza virus 3 strain Shipping Fever, complete genome," Accesion No. AF178655, Sep. 19, 2000.

Genbank, "*Clostridium tetani* E88, complete genome," Accession No. AE015927.1, Feb. 4, 2003.

Genbank "*E. coli* operon rpoBC coding for the beta- and beta'-subunits of RNA polymerase (genes rpoC and rpoB), and genes rplL, rlpJ, rplA, and rplK coding for 50S ribosomal subunit proteins L7/L12, L10, L1, and L11, respectively. (Map position 89-90 min.)," Accession No. 42813, Feb. 28, 1992.

Genbank, "*E.coli* 16S ribosomal RNA," Accession No. 174375, Aug. 11, 1995.

Genbank, "*E.coli* Open Reading Frame Upstream of Leu Operon," Accession No. M21150, Sep. 15, 1990.

Genbank "*E.coli* rRNA operon (rrnB) coding for Glu-tRNA-2, 5S, 16S and 23S rRNA," Accession No. 147581, Sep. 14, 1992.

Genbank, "Enterococcus malodoratus strain ATCC43197 elongation factor Tu (tufA) gene, partial cds," Accession No. AF274728, Dec. 11, 2000.

Genbank "*Escherichia coli* str. K-12 substr. MG1655, Complete Genome," Accession No. NC000913, Oct. 15, 2001.

Genbank, "Homo Sapiens Haplotype V Mitochondrion, Complete Genome", Accession No. AF381990.1, Dec. 28, 2001.

Genbank, "Human Adenovirus Type 4 Hexon Gene," for Accession No. X84646, Jun. 30, 1995.

Genbank, "Human coronavirus 229E, complete genome," Accession No. AF304460, Jul. 11, 2001.

Genbank, "Human Isolate L34 Mitochondrion D-loop Region", Accession No. U08081.1, Aug. 16, 1994.

GenBank, "il11b08.y1 Human insulinoma *Homo sapiens* cDNA clone Image:6029534 5—similar to SW:COX3_Human P00414 Cytochrome C Oxidase Polypeptide III ;, mRNA sequence", Accession No. BQ581956.1, Jun. 20, 2002.

Genbank, "Influenza B Virus B/Panama/45/90 Polymerase (PB2) mRNA, Complete Cds", Accession No. AF005737, pp. 1-3, Oct. 4, 1997.

Genbank, "Mastadenovirus h7 hexon gene," Accession No. Z48571, Apr. 18, 2005.

GenBank, "or72a01.s1 NCI_CGAP_Lu5 *Homo sapiens* cDNA Clone Image:16013523—similar to SW:COX1_Human P00395 Cytochrome C Oxidase Polypeptide I ;, mRNA sequence", Accession No. AI002209.1, Jun. 10, 1998.

Genbank "*Staphylococcus aureus* RN4220 ErmC gene, partial cds," Accession No. 18542231, Sep. 16, 2003.

Genbank "*Staphylococcus aureus* Strain MSSA476, Complete Genome," Accession No. BX571857.1, Jun. 24, 2004.

Genbank, "*Staphylococcus aureus* subsp. aureus Mu50, complete genome," Accession No. 15922990, Oct. 4, 2001.

Genbank "*Staphylococcus aureus* Subsp. Aureus MW2, Complete Genome," Accession No. G121281729, May 31, 2002.

Genbank, "*Staphylococcus epidermidis* ATCC 12228, complete genome," Accession No. AE015929.1, Jan. 2, 2003.

Genbank "*Streptococcus agalactiae* 2603V/R, complete genome," Accession No. AE009948.1, Aug. 28, 2002.

Genbank, "*Streptococcus anginosus* Elongation Factor Tu (tuf) Gene, Partial cds," Accession No. AF276257.1, Jul. 1, 2001.

Genbank "*Streptococcus pneumoniae* isolate 95.1 In00S DNA gyrase subunit B (gyrB) gene, complete cds," Accession No. 73916349, Sep. 30, 2005.

Genbank, "*Streptococcus pyogenes* strain MGAS8232, complete genome," Accession No. AE009949.1, Apr. 3, 2002.

Genbank, "Venezuelan equine encephalitis virus nonstructural polyprotein and structural polyprotein genes, complete cds," Accession No. AF375051.1, Jun. 26, 2001.

Gendel S.M., "Computational Analysis of the Specificity of 16S rRNA-Derived Signature Sequencesfor Identifying Food-Related Microbes," Food Microbiology, 1996, vol. 13, pp. 1-15.

Gibb T.R., et al., "Development and Evaluation of a 5' Fluorogenic Nuclease Assay to Detect and Differentiate Between Ebola Virus Subtypes Zaire and Sudan," Journal of Clinical Microbiology, 2001, vol. 39 (11), pp. 4125-4130.

Gilbert N., et al., "Comparison of Commercial Assays for the Quantitation of HBV DNA Load in Healthcare Workers: Calibration Differences," Journal of Virological Methods, 2002, vol. 100 (1-2), pp. 37-47.

Giles R.E., et al., "Maternal Inheritance of Human Mitochondrial DNA," Proceedings of the National Academy of Sciences, 1980, vol. 77 (11), pp. 6715-6719.

Gill S.R., et al., "Insights on Evolution of Virulence and Resistance from the Complete Genome Analysis of an Early Methicillin-Resistant *Staphylococcus aureus* Strain and a Biofilm-Producing Methicillin-Resistant *Staphylococcus epidemidis* Strain," Journal of Bacteriology, 2005, vol. 187 (7), pp. 2426-2438.

Gilliland G., et al., "Analysis of Cytokine mRNA and DNA: Detection and Quantitation by Competitive Polymerase Chain Reaction," Proceedings of the National Academy of Sciences of USA, 1990, vol. 87 (7), pp. 2725-2729.

Ginther C., et al., "Identifying Individuals by Sequencing Mitochondrial DNA from Teeth," Nature Genetics, 1992, vol. 2 (2), pp. 135-138.

Gjoen K.V., et al., "Specific Detection of Coxsackie Viruses A by the Polymerase Chain Reaction," Clinical and Diagnostic Virology, 1997, vol. 8 (3), pp. 183-188.

Golden M. R., et al., "Pilot Study of COBAS PCR and Ligase Chain Reaction for Detection of Rectal Infections Due to Chlamydia trachomatis," Journal of Clinical Microbiology, 2003, vol. 41 (5), pp. 2174-2175.

Goto K., et al., "Applications of the Partial 16S rDNA Sequence as an Index for Rapid Identification of Species in the Genus Bacillus," Journal of General and Applied Microbiology, 2000, vol. 46 (1), pp. 1-8.

Gravet A., et al., "Characterization of a Novel Structural Member, LukE-LukD, of the Bi-Component Staphylococcal Leucotoxins Family," FEBS Letters, 1998, vol. 436 (2), pp. 202-208.

Gray G.C., et al., "Adult Adenovirus Infections: Loss of Orphaned Vaccines Precipitates Military Respiratory Disease Epidemics," Clinical Infectious Diseases, 2000, vol. 31, pp. 663-670.

Greenberg B.D., et al., "Intraspecific Nucleotide Sequence Variability Surrounding the Origin of Replicationin Human Mitochondrial DNA," Gene, 1983, vol. 21, pp. 33-49.

Griffey, et al., "Detection of Base Pair Mismatches in Duplex DNA and RNA Oligonucleotides Using Electrospray Mass Spectrometry," SPIE, 1997, vol. 2985, pp. 82-86.

Griffin T.J., et al., "Direct genetic analysis by matrix-assisted laseer desorption/ionization mass spectrometry," PNAS, 1999, vol. 96 (11), pp. 6301-6306.

Griffin T.J., et al., "Single-Nucleotide Polymorphism Analysis by Maldi-TOF Mass Spectrometry," Trends in Biotechnology, 2000, vol. 18 (2), pp. 77-84.

Grondahl B., et al., "Rapid Identification of Nine Microorganisms Causing Acute Respiratory TractInfections by Single-Tube Multiplex Reverse Transcription-PCR: Feasibility Study," Journal of Clinical Microbiology, 1999, vol. 37 (1), pp. 1-7.

Grundmann H., et al., "Emergence and Resurgence of Meticillin—Resistant Staphylococcus aureus as a Public-Health Threat," Lancet, 2006, vol. 368 (9538), pp. 874-885.

Grzybowski T., et al., "Extremely High Levels of Human Mitochondrial DNA Heteroplasmy in Single Hair Roots," Electrophoresis, 2000, vol. 21 (3), pp. 548-553.

Gu Z., et al., "Multiplexed, Real-Time PCRr for Quantitative Detection of Human Adenovirus," Journal of Clinical Microboilogy, 2003, vol. 41 (10), pp. 4636-4641.

Guatelli J.C., et al., "Nucleic Acid Amplification In Vitro: Detection of Sequences with Low Copy Numbers and Application to Diagnosis of Human Immunodeficiency Virus Type 1 Infection," Clinical Microbiology Reviews, 1989, vol. 2 (2), pp. 217-226.

Haff L.A., et al., "Multiplex Genotyping of PCR Products with Mass Tag-Labeled Primers," Nucleic Acids Research, 1997, vol. 25 (18), pp. 3749-3750.

Hahner S., et al., "Analysis of Short Tandem Repeat Polymorphisms by Electrospray Ion Trap Mass Spectrometry," Nucleic Acids Research, 2000, vol. 28 (18), pp. E82.1-E82.8.

Haines J.D., et al., "Medical Response to Bioterrorism: Are we Prepared," Journal of Oklahoma State Medical Association, 2000, vol. 93, pp. 187-196.

Hall T.A., et al., "Base Composition Analysis of Human Mitochondrial DNA Using Electrospray Ionization Mass Spectrometry: A Novel Tool for the Identification and Differentiation of Humans," Analytical Biochemistry, 2005, vol. 344 (1), pp. 53-69.

Hamdad F., et al., "Detection of Methicillin/Oxacillin Resistance and Typing in Aminoglycoside-Susceptible Methicillin-Resistant and Kanamycin-Tobramycin-Resistant Methicillin-Susceptible," Microbial Drug Resistance, 2006, vol. 12 (3), pp. 177-185.

Hamel S., et al., "Consensus PCR and Microarray for Diagnosis of the Genus Staphylococcus, Species, and Methicillin Resistance," Biotechniques, 2001, vol. 31 (6), pp. 1364-1372.

Hammerle T., et al., "A Sensitive PCR Assay System for the Quantitation of Viral Genome Equivalents:Hepatitis C Virus (HCV)," Archives of Virology, 1996, vol. 141 (11), pp. 2103-2114.

Hannis J.C., et al., "Accurate Characterization of the Tyrosine Hydroxylase Forensic Allele 9.3 through Development of Electrospray Ionization Fourier Transform Ion Cyclotron Resonance Mass Spectrometry," Rapid Communications in Mass Spectrometry, 1999, Vol. 13 (10), pp. 954-962.

Hannis J.C., et al., "Detection of Double-Stranded PCR Amplicons at the Attomole Level Electrosprayed from Low Nanomolar Solutions using FT-ICR Mass Spectrometry," Journal of Analytical Chemistry, 2001, vol. 369 (3-4), pp. 246-251.

Hannis J.C., et al., "Genotyping Complex Short Tandem Repeats Using Electrospray lonzation Fourier Transform Ion Cyclotron Resonance Multi-Stage Mass Spectrometry," Proceedings of SPIE, 2000, vol. 3926, pp. 36-47.

Hannis J.C., et al., "Genotyping Short Tandem repeats using flow Injection and Electrospray Ionization , Fourier Transform ion Cyclotron Resonance Mass Spectrometry," Rapid Communications in Mass Spectrometry, 2001, vol. 15 (5), pp. 348-350.

Hannis J.C., et al., "Nanoelectrospray Mass Spectrometry Using Non-Metalized, Tapered (50-10 .mu.m) Fused-silica Capillaries," Rapid Communication in Mass spectrometry, 1998, vol. 12, pp. 443-448.

Hanssen A.M., et al., "Sccmecin Staphylococci: Genes on the Move," FEMS Immuol Medical Microbiol, 2006, vol. 46, pp. 8-20.

Hasebe F. et al., "Combined Detection and Genotyping of Chikungunya Virus by a Specific Reverse Transcription-Polymerase Chain Reaction," Journal of Medical Virology, 2002, vol. 67 (3), pp. 370-374.

Hassan A.A., et al., "Inter- and Intraspecies Variations of the 16S-23S rDNA Intergenic Spacer Region of Various Streptococcal Species," Systematic and Applied Microbiology, 2003, vol. 26 (1), pp. 97-103.

Haugland R.A., et al., "Identification of Putative Sequence Specific PCR Primers for Detection of the Toxygenic Fungal Species Stachybotrys Chartarum," Molecular and Cellular Probes, 1998, vol. 12 (6), pp. 387-396.

Hayashi H., et al., "Phylogenetic Analysis of the Human gut Microbiota using 16S rDNA clone Libraries and Strictly Anaerobic Culture-based Methods," Journal of Microbiology, Immunology, 2002, vol. 46 (8), pp. 535-548.

He L., et al, "Development of a Capillary High-performance Liquid Chromatography Tandem Mass Spectrometry System Using SWIFT Technology in an Ion Trap/Reflectron Time-of-flight Mass Spetrometer," Biochemical and Biophysical Research Communications, 1997, vol. 11, pp. 1739-1748.

Heim A., et al., "Rapid and Quantitative Detection of Human Adenovirus Dna by Real-Time PCR," Journal of Medical Viral, 2003, vol. 70, pp. 228-239.

Henchal E.A., et al., "Sensitivity and Specificity of a Universal Primer set for the Rapid Diagnosis of Dengue Virus Infections by Polymerase Chain Reaction and Nucleic acid Hybridization," American Journal of Tropical Medicine and Hygiene, 1991, vol. 45 (4), pp. 418-428.

Herrmann B., et al., "Differentiation of Chiamydia spp. By Sequence Determination and Restriction Endonuclease Cleavage of RNase P RNA Genes," Journal of Clinical Microbiology, 1996, vol. 34 (8), pp. 1897-1902.

Higgins G.S., et al., "Competitive Oligonucleotide Single-base Extension Combined with Mass Spectrometric Detection for Mutation Screening," Biotechniques, 1997, vol. 23 (4), pp. 710-714.

Higgins J.A., et al., "Sensitive and Rapid Identification of Biological Threat Agents," Annals of the New York Academy of Sciences, 1999, vol. 894, pp. 130-148.

Hill F., et al., "Polymerase Recognition of Synthetic Oligodeoxyribonucleotides Incorporating Degenerate Pyrimidine and Purine Bases," Proceedings of the National Academy of Sciences, 1998, vol. 95, pp. 4258-4263.

Hiramatsu K., et al., "The Emergence and Evolution of Methicillin-Resistant Staphylococcusaureus," Trends Microbiology, 2001, vol. 9 (10), pp. 486-493.

Hodgson J.E., et al., "Molecular Characterization of the Gene Encoding High-Level Mupirocin Resistancein Staphylococcus aureus J2870," Antimicrobial Agents and Chemotherapy, 1994, vol. 38 (5), pp. 1205-1208.

Hoffman E., et al., "Rescue of Influenza B Virus from Eight Plasmids," Proceedings of the National Academy of Sciences, 2002, vol. 99 (17), pp. 11411-11416.

Hoffmann E., et al., "Universal Primer Set for the Full-Length Amplification of all Influenza a Viruses.," Archives of Virology, 2001, vol. 146 (12), pp. 2275-2289.

Hofstadler S.A., et al., "TIGER: The Universal Biosensor," International Journal of Mass Spectrometry, 2005, vol. 242, pp. 23-41.

Holden M.T., et al., "Complete Genomes of Two Clinical *Staphylocuccus aureus* Strain: Evidence for the Rapid Evolution of Virulence and Drug Resistance," Proceedings of the National Academy of Sciences, 2004, vol. 101 (26), pp. 9786-9791.

Holland M.M., et al., "Mitochondria! DNA Sequence Analysis of Human Skeletal Remains: Identification of Remains from the Vietnam War," Journal of Forensic Sciences, 1993, vol. 38 (3), pp. 542-553.

Holland M.M., et al., "Mitochondrial DNA Sequence Analsysis—Validation and Use for Forensic Casework," Forensic Science Review, 1999, vol. 11 (1), pp. 22-50.

Holm L., et al., "Removing Near-Neighbour Redundancy from Large Protein Sequence Collections," Bioinformatics, 1998, vol. 14 (5), pp. 423-429.

Holmes E.C., et al., "Whole-Genome Analysis of Human Influenza A Virus Reveals Multiple Persistent Lineages and Reassortment among Recent H3N2 Viruses," Public Library of Science Biology, 2005, vol. 3 (9), pp. 1579-1589.

Honda K., et al., "Universal Method of Hypersensitive Nested PCR Toward Forensic DNA typing," International Congress Series, 1998, vol. 7, pp. 28-30.

Hongoh Y., et al., "Evaluation of Primers and PCR Conditions for the Analysis of 16s rRNA Genes from a Naturalenvironment," FEMS Microbiology Letters, 2003, vol. 221 (2), pp. 299-304.

Hood E., et al., "Chemical and Biological Weapons: New Questions, New Answers," Environmental Health Perspectives, 1999, vol. 107 (12), pp. 931-932.

Houng H.S., et al., "Rapid Type-Specific Diagnosis of Adenovirus Type 4 Infection Using a Hexon—Based Quantitative Fluorogenic Pcr," Diagnostic Microbiology and Infectious Disease, 2002, vol. 42 (4), pp. 227-236.

Howell N., et al., "Persistent Heteroplasmy of a Mutation in the Human Mtdna Control Region: Hypermutation As an Apparent Consequence of Simple-Repeat Expansion/Contraction," American Journal of Human Genetics, 2000, vol. 66 (5), pp. 1589-1598.

Huber C.G., et al., "On-Line Cation Exchange for Suppression of Adduct Formation in Negative-Ion Electrospray Mass Spectrometry of Nucleic Acids," Analytical Chemistry, 1998, vol. 70 (24), pp. 5288-5295.

Huletsky A., et al., "New Real-Time Pcr Assay for Rapid Detection of Methicillin-Resistantstaphylococcus Aureus Directly from Specimens Containing a Mixture of *Staphylococci*," Journal of Clinical Microbiology, 2004, vol. 42 (5), pp. 1875-1884.

Hunag C., et al., "Detection of Arboviral RNA Directly from Mosquito Homogenates by Reverse Transcription-Polymerase Chain Reaction," Journal of Virological Methods, 2001, vol. 94 (1-2), pp. 121-128.

Hung E.C., et al., "Detection of SARS coronavirus RNA in the cerebrospinal fluid of a patient with severe acute respiratory syndrome," Clinical Chemistry, 2003, vol. 49 (12), pp. 2108-2109.

Hurdle J.G., et al., "Analysis of Mupirocin Resistance and Fitness in *Staphylococcus aureus* by Molecular Genetic and Structural Modeling Techniques," Antimicrobial Agents and Chemotherapy, 2004, vol. 48 (11), pp. 4366-4376.

Hurst G.B., et al., "Detection of Bacterial DNA Polymerase Chain Reaction Products by Matrix-Assisted Laser Desorptionfionization Mass Spectrometry," Rapid Communications in Mass Spectrometry, 1996, vol. 10 (3), pp. 377-382.

Hutchison C.A., et al., "Maternal Inheritance of Mammalian Mitochondrial DNA," Nature, 1974, vol. 251 (5475), pp. 536-538.

Hyde-Deruysch Er R., et al., "Polyomavirus Early-Late Switch is not Regulated at the Level of Transcription Initiation and is associated with changes in RNA Processing," Proceedings of the National Academy of Sciences, 1988, vol. 85, pp. 8993-8997.

Ieven M., et al., "Rapid Detection of Methicillin Resistance in Coagulase-Negative *Staphylococci* by Commercially Available Fluorescence Test," Journal of Clinical Microbiology, 1995, vol. 33 (8), pp. 2183-2185.

Ihle O., et al., "Efficient Purification of DNA Fragments using a Protein Binding Membrane," Nucleic Acids Research, 2000, vol. 28 (16), pp. e76.

Inglis T.J., et al., "Rapid Genotypic Confirmation of Methicillin Resistance," Pathology, 1996, vol. 28 (3), pp. 259-261.

Ingman M., et al., "Mitochondrial Genome Variation and the Origin of Modern Humans," Nature, 2000, vol. 408 (6813), pp. 708-713.

International Preliminary Examination Report for Application No. PCT/US2002/06763, mailed on Jun. 11, 2003, 6 pages.

International Preliminary Examination Report for Application No. PCT/US2002/20336, mailed on May 12, 2004, 8 pages.

International Preliminary Examination Report for Application No. PCT/US2003/09802, mailed on Apr. 8, 2005, 7 pages.

International Preliminary Examination Report for Application No. PCT/US2003/22835, mailed on Mar. 5, 2005, 4 pages.

International Preliminary Examination Report for Application No. PCT/US2003/38505, mailed on Mar. 3, 2006, 5 pages.

International Preliminary Examination Report for Application No. PCT/US2003/38757, mailed on Feb. 2, 2007, 5 pages.

International Preliminary Examination Report for Application No. PCT/US2003/38761, mailed on Jun. 27, 2006, 6 pages.

International Preliminary Report on Patentability and Written Opinion for Application No. PCT/US2005/00386, mailed on Jul. 10, 2006, 6 pages.

International Preliminary Report on Patentability and Written Opinion for Application No. PCT/US2005/030058, mailed on Aug. 20, 2007, 6 pages.

International Preliminary Report on Patentability and Written Opinion for Application No. PCT/US2005/033707, mailed on Mar. 20, 2007, 6 pages.

International Preliminary Report on Patentability for Application No. PCT/US2004/033742, mailed on Jun. 20, 2006, 1 page.

International Preliminary Report on Patentability for Application No. PCT/US2006/028397, mailed on Jan. 22, 2008, 1 page.

International Preliminary Report on Patentability for Application No. PCT/US2008/054926, mailed on Aug. 26, 2009, 1 page.

International Preliminary Report on Patentability, Written Opinion and International Search Report for Application No. PCT/US2004/015123, mailed on Oct. 3, 2005, 8 pages.

International Search Report and the Written Opinion for Application No. PCT/US2008/064891, mailed on Jun. 29, 2009, 15 pages.

International Search Report and Written Opinion for Application No. PCT/US2005/018031, mailed on Jun. 28, 2006, 14 pages.

International Search Report and Written Opinion for Application No. PCT/US2006/007747, mailed on Sep. 5, 2006, 13 pages.

International Search Report and Written Opinion for Application No. PCT/US2006/028397, mailed on Mar. 5, 2007, 14 pages.

International Search Report and Written Opinion for Application No. PCT/US2006/040747, mailed on Mar. 17, 2009, 19 pages.

International Search Report and Written Opinion for Application No. PCT/US2006/061307, mailed on Jan. 9, 2008, 21 pages.

International Search Report and Written Opinion for Application No. PCT/US2007/20045 mailed on Jan. 8, 2009, 18 pages.

International Search Report and Written Opinion for Application No. PCT/US2008/054926, mailed on Jan. 26, 2009, 15 pages.

International Search Report and Written Opinion for Application No. PCT/US2008/057717, mailed on Jan. 13, 2009, 18 pages.

International Search Report and Written Opinion for Application No. PCT/US2008/057901, mailed on Aug. 28, 2008, 14 pages.

International Search Report for Application No. PCT/US02/20336, mailed on Feb. 3, 2003, 4 pages.

International Search Report for Application No. PCT/US04/007236, mailed on Feb. 24, 2006, 2 pages.

International Search Report for Application No. PCT/US2002/06763, mailed on Oct. 23, 2002, 4 pages.

International Search Report for Application No. PCT/US2003/009802, mailed on Aug. 3, 2004, 2 pages.

International Search Report for Application No. PCT/US2003/038505 mailed on Apr. 12, 2005.

International Search Report for Application No. PCT/US2003/038830, mailed on Aug. 25, 2004, 4 pages.

International Search Report for Application No. PCT/US2003/22835, mailed on Dec. 12, 2003, 1 page.

International Search Report for Application No. PCT/US2003/38505, mailed on Apr. 12, 2005, 2 pages.

International Search Report for Application No. PCT/US2003/38757, mailed on Jun. 24, 2004, 2 pages.

International Search Report for Application No. PCT/US2003/38761, mailed on Dec. 30, 2005, 5 pages.
International Search Report for Application No. PCT/US2003/38795, mailed on Apr. 19, 2004, 3 pages.
International Search Report for Application No. PCT/US2004/011877, mailed on Apr. 20, 2006, 4 pages.
International Search Report for Application No. PCT/US2004/012671, mailed on Sep. 28, 2007, 2 pages.
International Search Report for Application No. PCT/US2004/015123, mailed on Oct. 3, 2005, 2 pages.
International Search Report for Application No. PCT/US2004/015196, mailed on Jul. 1, 2005, 3 pages.
International Search Report for Application No. PCT/US2004/028869, mailed onJul. 17, 2006, 4 pages.
International Search Report for Application No. PCT/US2004/033742, mailed on May 15, 2006, 2 pages.
International Search Report for Application No. PCT/US2005/000386, mailed on May 9, 2006, 3 pages.
International Search Report for Application No. PCT/US2005/005356, mailed on Aug. 7, 2007, 4 pages.
International Search Report for Application No. PCT/US2005/006133, mailed on Jul. 26, 2007, 4 pages.
International Search Report for Application No. PCT/US2005/007022, mailed on Oct. 20, 2006, 1 page.
International Search Report for Application No. PCT/US2005/009557, mailed on Sep. 19, 2005, 1 page.
International Search Report for Application No. PCT/US2005/018337, mailed on Oct. 10, 2006, 2 pages.
International Search Report for Application No. PCT/US2005/024799, mailed on Dec. 28, 2006, 4 pages.
International Search Report for Application No. PCT/US2005/030058, mailed on Aug. 20, 2007, 1 page.
International Search Report for Application No. PCT/US2005/033707, mailed on Feb. 6, 2006, 3 pages.
International Search Report for Application No. PCT/US2007/066194, mailed on Jan. 15, 2008, 4 pages.
International Search Report for Application No. PCT/US2008/057901, mailed on Jun. 29, 2009, 15 pages.
International Search Report for Application No. PCT/US2008/065332, mailed on Nov. 28, 2008, 5 pages.
International Search Report for Application No. PCT/US2009/045635, mailed on Oct. 7, 2009, 9 pages.
Inyaku K., et al., "Rapid Detection and Identification of Mycobacteria in Sputum Samples by NestedPolymerase Chain Reaction and Restriction Fragment Length Polymorphisms of dnaJ Heat ShockProtein Gene," Journal of Medical Sciences, 1993, vol. 42 (1), pp. 21-31.
Iqbal S.S., et al., "A Review of Molecular Recognition Technologies for Detection of Biological Threat Agents," Biosensors & Bioelectronics, 2000, vol. 15 (11-12), pp. 549-578.
Isola N.R., et al., "MALDI-TOF mass spectrometric method for detection of hybridized DNA oligomers," Analytical Chemistry, 2001, vol. 73 (9), pp. 2126-2131.
Iteman I., et al., "Comparison of Conserved Structural and Regulatory Domains within Divergent 16S rRNA-23S rRNA Spacer Sequences of Cyanobacteria," Microbiology, vol. 146 (Pt 6), pp. 1275-1286, published 2000.
Ito T., et al., "Insights on Antibiotic Resistance of Staphylococcus aureus from its Whole Genome: Genomic Island Scc," Drug Resistance Updates, 2003, vol. 6 (1), pp. 41-52.
Ito T., et al., "Structural Comparison of Three Types of Staphylococcal Cassette Chromosome mecIntegrated in the Chromosome in Methicillin-Resistant Staphylococcus aureus," Antimicrobial Agents and Chemotherapy, 2001, vol. 45 (5), pp. 1323-1336.
Jackson P.E., et al., "Mass Spectrometry for Genotyping: an Emerging Tool for Molecular Medicine," Molecular Medicine Today, 2000, vol. 6 (7), pp. 271-276.
James A.M., et al., "Borelia Lonestari Infection after a Bite by an Amblyomma Americanum Tick," The Journal of Infectious Diseases, 2001, vol. 183 (12), pp. 1810-1814.
Jankowski K., et al., "Mass Spectrometry of DNA. Part 2 Quantitative Estimation of Base Composition," European Journal of Mass Spectrometry, 1980, vol. 1 (1), pp. 45-52.
Jansen R.C., et al., "Genotype-by-environment Interaction in Genetic Mapping of Multiple Quantitative Trait Loci," Theoretical and Applied Genetics, 1995, vol. 91, pp. 33-37.
Jaulhac B., et al., "Specific Detection of the Toxic Shock Syndrome Toxin-1 Gene Using the Polymerase Chain Reaction," Molecular and Cellular Probes, 1991, vol. 5, pp. 281-284.
Jaulhac B., et al., "Synthetic DNA Probes for Detection of Genes for Enterotoxins A, B, C, D, E and for Tsst-1 In Staphylococcal Strains," Journal of Applied Bacterial, 1992, vol. 72 (5), pp. 386-392.
Jensen M.A., et al., "Rapid Identification of Bacteria on the Basis of Polymcrase Chain Reaction-Amplified Ribosomal DNA Spacer Polymorphisms," Applied and Environmental Microbiology, 1993, vol. 59 (4), pp. 945-952.
Jeong J., et al., "Early Screening of Oxacillin-Resistant Staphylococcus aureus and Staphylococcus epidermidis From Blood Culture," Journal of Korean Medical Science, 2002, vol. 17, pp. 168-172.
Jiang C., et al., "Multiple Trait Analysis of Genetic Mapping for Quantitative Trait Loci Genetics," Genetics, 1995, vol. 140 (3), pp. 1111-1127.
Jiang Y., et al., "A Highly Efficient and Automated Method for Purifying and Desalting PCR Products for Analysis by Electrospray Ionization Mass Spectrometry," Analytical Biochemistry, 2003, vol. 316 (1), pp. 50-57.
Johansson A., et al., "Evaluation of Pcr-based Methods for Discrimination of Francisella species and Subspecies and Development of a Specific PCR that Distinguishes the two Major Subspecies of Francisella Tularensis," Journal of Clinical Microbiology, 2000, vol. 38 (11), pp. 4180-4185.
Johnson W.M., et al., "Detection of Genes for Enterotoxins, Exfoliative Toxins, and Toxic Shock Syndrome Toxin 1 in Staphylococcus aureus by the Polymerase Chain Reaction," Journal of Clinical Microbiology, 1991, vol. 29 (3), pp. 426-430.
Johnson Y.A., et al., "Precise Molecular Weight Determination of PCR Products of the rRNA Intergenic Spacer Region Using Electrospray Quadrupole Mass Spectrometry for Differentiation of B. subtilis and B. atrophaeus, Closely Related Species of Bacilli," Journal of Microbiological Methods, 2000, vol. 40 (3), pp. 241-254.
Jonas D., et al., "Rapid PCR-Based Identification of Methicillin-Resistant Staphylococcus aureusfrom Screening Swabs," Journal of Clinical Microbiology, 2002, vol. 40 (5), pp. 1821-1823.
Jurinke C., et al., "Application of Nested PCR and Mass Specctrometry for DNA Based Virus Detection: HBV-DNA Detected in the Majority of Isolated Anti-Hbc Positive Sera," Genetic Analysis: Biomolecular Engineering, 1998, vol. 14 (3), pp. 97-102.
Jurinke C., et al., "Detection of Hepatitis B: Virus DNA in Serum Samples Via Nested PCR and MALDI-TOF Mass Spectrometry," Genetic Analysis: Biomolecular Engineering, 1996, vol. 13 (3), pp. 67-71.
Jurinke C., et al., "MALDI-TOF Mass Spectrometry. A Versatile Tool for High-Performance DNA Analysis," Molecular Biotechnology, 2004, vol. 26 (2), pp. 147-163.
Kacian D.L., et al., "A Replicating RNA Molecule Suitable for a Detailed Analysis of Extracellular Evolution and Replication," Proceeding of the National Academy of Sciences, 1972, vol. 69 (10), pp. 3038-3042.
Kageyama A., et al. "Rapid Detection of Human Fecal Eubacterium Species and Related Genera by Tested PCR Method," Journal of Microbiology, Immunology, 2001, vol. 45 (4), pp. 315-318.
Kajon A.E., et al., "Genome Type Analysis of Brazilian Adenovirus Strains of Serotypes 1, 2, 3, 5,and 7 collected Between 1976 and 1995," Journal of Medical, 1999, vol. 58 (4), pp. 408-412.
Kasai H., et al., "Construction of the gyrB Database for the Identification and Classification of Bacteria," Genome Informatics. Workshop on Genome Informatics, 1998, pp. 13-21.
Katano H., et al., "Identification of Adeno-Associated Virus Contamination in Cell and Virus Stocks by PCR," Biotechniques, 2004, vol. 36 (4), pp. 676-680.
Katayama Y., et al., "Genetic Organization of the Chromosome Region Surrounding mecA inClinical Staphylococcal Strains: Role of IS431—Mediated mecl Deletion in Expression of Resistance inmed-Canying, Low-Level Methicillin-Resistant Staphylococcus haemolyticus," Antimicrobial Agents and Chemotherapy, 2001, vol. 45 (7), pp. 1955-1963.

Ke D., et al., "Development of a PCR Assay for Rapid Detection of Enterococci," Journal of Clinical Microbiology, 1999, vol. 37 (11), pp. 3497-3503.

Kearns A.M., et al., "Rapid Detection of Methicillin-Resistant Staphylococci by Multiplex PCR," The Journal of Hospital Inspection, 1999, vol. 43 (1), pp. 33-37.

Keller A., et al., "Empirical Statistical Model to Estimate the Accuracy of Peptide Identifications Made by MS/MS and Database Search," Analytical Chemistry, 2002, vol. 74 (20), pp. 5383-5392.

Khan A.S., et al., "An Outbreak of Crimean-Congo Haemorrhagic Fever in the United Arab Emirates, 1994-1995," The American Journal of Tropical Medicine and Hygiene, 1997, vol. 57 (5), pp. 519-525.

Khan S.A., et al., "Simultaneous Detection of Erythromycin-Resistant Methylase Genes ermA and ermC from *Staphylococcus* Spp. By Multiplex-PCR," Molecular and Cellular Probes, 1999, vol. 13 (5), pp. 381-387.

Kidd A.H., et al., "Rapid Subgenus Identification of Human Adenovirus Isolates by a General PCR," Journal of Clinical Microbiology, 1996, vol. 34 (3), pp. 622-627.

Kidd-Ljunggren K., et al., "The hepatitis B virus X gene: analysis of functional domain variation and gene phylogeny using multiple sequences," Journal of General Virology, 1995, vol. 76 (pt 9), pp. 2119-2130.

Kikuchi K., et al., "Restriction Fragment Length Polymorphism Analysis of Clinical Isolates of Mycobacterium Haemophilum," Journal of Clinical Microbiology, vol. 32 (7), pp. 1763-1767, published 1994.

Kilbourne E.D., "Influenza Pandemics of the 20th Century," Emerging Infectious Diseases Journal, 2006, vol. 12 (1), pp. 9-14.

Kilbourne E.D., "Influenza Pandemics: Can We Prepare for the Unpredictable," Viral Immunology, 2004, vol. 17 (3), pp. 350-357.

Kilpatrick D.R., et al., "Group-Specific Identification of Polioviruses by PCR Using Primer Containing Mixed—Base or Deoxyinosine Residues at Positions of Codon Degeneracy," Journal of Clinical Microbiology, 1996, vol. 34 (12), pp. 2990-2996.

Kim B.J., et al., "Identification of Mycobacterial Species by Comparative Sequence Analysis of the RNA Polymerase Gene (rpoB)," Journal of Clinical Microbiology, 1999, vol. 37 (6), pp. 1714-1720.

Kinney R.M., et al., "Nucleotide Sequences of the 26S mRNAs of the Viruses Defining the Venezuelan Equine Encephalitis Antigenic Complex," The American Journal of Tropical Medicine and Hygiene, 1998, vol. 59 (6), pp. 952-964.

Kirpekar F., et al., "Matrix Assisted Laser Desorption/Ionization Mass Spectrometry of Enzymatically Synthesjzed RNA up to 150 kDa," Nucleic Acids Research, vol. 22 (19), pp. 3866-3870, publised 1994.

Kitagawa Y., et al., "Rapid Diagnosis of Methicillin-Resistant *Staphylococcus aureus* Bacteremia by Nested Polymerase Chain Reaction," Annals of Surgery, 1996, vol. 224 (5), pp. 665-671.

Knoth K., et al., "Highly Degenerate, Inosine-Containing Primers Specifically Amplify Rare cDNA using the Polymerase Chain Reaction," Nucleic Acids Research, 1988, vol. 16 (22), pp. 10932.

Kolbert C.P., et al., "Branched-DNA Assay for Detection of the mecA Gene in Oxacillin-Resistant and Oxacillin-Sensitive Staphylococci," Journal of Clinical Microbiology, 1998, vol. 36 (9), pp. 2640-2644.

Kowalak J.A., et al., "A Novel Method for the Determination of Post-Transcriptional Modification in RNA by Mass Spectrometry," Nucleic Acids Research, 1993, vol. 21 (19), pp. 4577-4585.

Krafft A.E., et al., "Evaluation of PCR Testing of Ethanol-Fixed Nasal Swab Specimens as an Augmented Surveillance Strategy for Influenza Virus and Adenovirus Identification," Journal of Clincal Microbiology, 2005, vol. 43 (4), pp. 1768-1775.

Krahmer M.T., et al., "Electrospray Quadrupole Mass Spectrometry Analysis of Model Oligonucleotides and Polymerase Chain Reaction Products: Determination of Base Substitutions, Nucleotide Additions/Deletions, and Chemical Modifications," Analytical Chemistry, 1999, vol. 71 (14), pp. 2893-2900.

Krahmer M.T., et al, "MS for Identification of Single Nucleotide Polymorphisms and MS/MS for Discrimination of Isomeric PCR Products," Analytical Chemistry, 2000, vol. 72 (17), pp. 4033-4040.

Kramer L.D., et al., "Dection of Encephalitis Viruses in Mosquitoes (Diptera: Culicidea) and Avian Tissues," Journal of Medical Entomology, 2002, vol. 39 (2), pp. 312-323.

Kramer L.D., et al., "Dection of St. Louis Encephalitis and Western Equine Encephalomyelitis RNA in Mosquitoes Tested Without Maintainance of a Cold Chain," Journal of the American Mosquito Control Association, 2001, vol. 17 (4), pp. 213-215.

Kresken M., et al., "Prevalence of Mupirocin Resistance in Clinical Isolates of *Staphylococccus aureus* and *Staphylococcus epidermidis*: Results of the Antimicrobial Resistance Surveillance Study of the Paul-Ehrlich-Society for Chemotherapy, 2001," International Journal of Antimicrobial Agents, 2004, vol. 23 (6), pp. 577-581.

Krishnan P.U., et al., "Detection of Methicillin and Mupirocin Resistance in *Staphylococcus aureusisolates* Using Conventional and Molecular Methods: A Descriptive Study from a Burns Unit with Highprevalence of Mrsa," Journal of Clinical Pathology, 2002, vol. 55 (10), pp. 745-748.

Kroes I., et al., "Bacterial Diversity Within the Human Subgingival Crevice," Proceeding of the National Academy of Sciences, 1999, vol. 96 (25), pp. 14547-14552.

Krossoy B., et al., "The Putative Polymerase Sequence of Infectious Salmon Anemia Virus Suggests a New Genus within the Orthomyxoviridae," Journal of Virology, 1999, vol. 73 (3), pp. 2136-2142.

Ksiaxek T.G., et al., "A Novel Coronavirus Associated with Severe Acute Respiratory Syndrome," The New England Journal of Medicine, 2003, vol. 348 (20), pp. 1953-1966.

Kupke T., et al., "Molecular Characterization of Lantibiotic-Synthesizing Enzyme EpiD Reveals a Function for Bacterial Dfp Proteins in Coenzyme A Biosynthesis," Journal of Biological Chemistry, 2000, vol. 275 (41), pp. 31838-31846.

Kuroda M., et al., "Whole Genome Sequencing of Meticillin-Resistant *Staphylococcus aureus*," The Lancet, 2001, vol. 357 (9264), pp. 1225-1240.

Kwok S., et al., "Avoiding False Positives with PCR," Nature, 1989, vol. 339 (6221), pp. 237-238.

Labandeira-Rey, M. et al., "*Staphylococcus aureus* Panton Valentine Leukocidin Causes Necrotizing Pneumonia," Sciencexpress, 2007, 8 pages.

Lacroix J.M., et al, "PCR-Based Technique for the Detection of Bacteria in Semen and Urine," Journal of Microbiological Methods, 1996, vol. 26, pp. 61-71.

Lacroix L., et al., "Triplex Formation by Oligonucleotides Containing 5-(1-PropynyI)-2-deoxyuridine: Decreased Magnesium Dependence and Improved Intracellular Gene Targeting," Biochemistry, 1999, vol. 38 (6), pp. 1893-1901.

Laken S.J., et al., "Genotyping by Mass Spectrometric Analysis of Short DNA Fragments," Nature Biotechnology, 1998, vol. 16 (13), pp. 1352-1356.

Lamb R.A., et al., "Sequence of Interrupted and Uninterrupted mRNAs and Cloned DNA Coding for the Two Overlapping Nonstructural Proteins of Influenza Virus," Cell, 1980, vol. 21 (2), pp. 475-485.

Lambert A.J., et al., "Detection of North American Eastern and Western Equine Encephalitis Viruses by Nucleic Acid Amplification Assays," Journal of Clinical Microbiology, 2003, vol. 41 (1), pp. 379-385.

Lau L.T., et al, "A Real-Time PCR for SARS-Coronavirus Incorporating Target Gene Pre-Amplification," Biochemical and Biophysical Research Communications, 2003, vol. 312 (4), pp. 1290-1296.

Lau L.T., et al., "Nucleic Acid Sequence-Based Amplification Methods to Detect Avian Influenza Virus," Biochemical and Biophysical Research Communications, 2004, vol. 313 (2), pp. 336-342.

Le Cann P., et al., "Quantification of Human Astroviruses in Sewage Using Real-Time RT-PCR," Research in Microbiology, 2004, vol. 155 (1), pp. 11-15.

Lebedev Y., et al., "Oligonucleotides Containing 2-Aminoadenine and 5-Methycytosine are More Effective as Primers for PCR Amplification than their Nonmodified Counterparts," Genetic Analysis: Biomolecular Engineering, 1996, vol. 13 (1), pp. 15-21.

Lednicky J.A., et al., "Polyomaviruses and Human Tumors: A Brief Review of Current Concenpts and Interpretations," Frontiers Bioscience, 1999, vol. 4, pp. D153-D164.

Lee J.A., et al., "Rapid Identification of Human Adenovirus Types 3 and 7 from Respiratory Specimens via Multiplex Type-Specific PCR," Journal of Clinical Microbiology, 2005, vol. 43 (11), pp. 5509-5514.

Lee J.H., et al., "Simultaneous Detection of Three Mosquito-Borne Encephalitis Viruses (Eastern equine, La Crosse, and St. Louis) with a Single-Tube Multiplex Reverse Transcriptase Polymerase Chaine Reaction Assay," Journal of the American Mosquito Control Association, 2002, vol. 18 (1), pp. 26-31.

Leif H., et al., "Isolation and Characterization of the Proton-Translocating NADH: Ubiqu None Oxidoreductase from *Escherichia coli*," European Journal of Biochemistry, 1995, vol. 230 (2), pp. 538-548.

Lengyel A., et al., "Characterization of the Main Protein Components of Adenovirus Virion and itsPossible Use in Laboratory Diagnostics," Acta Microbiologica Immunologica Hungarica, 1998, vol. 43 (3-4), pp. 281-283.

Leroy E.M., et al., "Diagnosis of Ebola Haemorrhagic Fever by RT-PCR in an Epidemic Setting," Journal of Medicinal Virology, 2000, vol. 60 (4), pp. 463-467.

Levi K., et al., "Evaluation of an Isothermal Signal Amplification Method for Rapid Detection of Methicillin-Resistant *Staphylococcus aureus* from Patient-Screening Swabs," Journal of Clinical Microbiology, 2003, vol. 41 (7), pp. 3187-3191.

Levine S.M., et al., "PCR-Based Detection of *Bacillus anthracis* in Formalin-Fixed Tissue from a Patient Receiving Ciprofloxacin," Journal of Clinical Microbiology, 2002, vol. 40 (11), pp. 4360-4362.

Levison P.R., et al., "Recent Developments of Magnetic Beads for Use in Nucleic Acid Purification," Journal of Chromatography, 1998, vol. A816, pp. 107-111.

Lewers K.S., et al., "Detection of Linked QTL for Soybean Brown Stem Rot Resistance in "BSR 101" as Expressed in a Growth Chamber Environment," Molecular Breeding, 1999, vol. 5, pp. 33-42.

Li C., et al., "Evolution of H9N2 Influenza Viruses from Domestic Poultry in Mainland China," Virology, 2005, vol. 340 (1), pp. 70-83.

Li J., et al., "Single Nucleotide Polymorphism Determination Using Primer Extension and Time-of-Flight Mass Spectrometry," Electrophoresis, 1999, vol. 20 (6), pp. 1258-1265.

Li Q., et al., "Genetic Variability of Hexon Loops 1 and 2 between Seven Genome Types of Adenovirus Serotype 7," Archives of Virology, 1999, vol. 144 (9), pp. 1739-1749.

Li Q., et al., "Screening of the High Yield Influenza B Virus on MDCK c14d Cloning of its Whole Genome," International Congress Series, 2004, pp. 610-614.

Li Q.G., et al., "Analysis of 15 Different Genome Types of Adenovirus Type 7 Isolated on FiveContinents," Journal of Virology, 1986, vol. 60 (1), pp. 331-335.

Li Q.G., et al., "Comparison of 17 Genome Types of Adenovirus Type 3 Identified among Strains Recovered from Six Continents," Journal of Clinical Microbiology, 1988, vol. 26 (5), pp. 1009-1015.

Liebermann H., et al., "Mapping of Epitopes on the Fiber Knobs of Human Adenovirus Serotypes 8 and 15," Intervirology, 2002, vol. 45 (1), pp. 59-66.

Liebermann H., et al., "Mapping of Linear Epitopes on Fibre Knob of Human Adenovirus Serotype 5," Virus Research, 2001, vol. 73 (2), pp. 145-151.

Lim L.P., et al., "The MicroRNAs of Caenorhabditis Elegans," Genes and Development, 2003, vol. 17 (8), pp. 991-1008.

Limbach P.A., et al., "Enzymatic Sequencing of Oligonucleotides with Electrospray Mass Spectrometry," 42nd ASMS Conference on Mass Spectrometry, 1994.

Limoncu M.N., et al., "Emergence of Phenotypic Resistance to Ciprofloxacin and Levofloxacin Inmethicillin-Resistant and Methicillin-Sensitive *Staphylococcus aureus* Strains," International Journal of Antimicrobial Agents, 2003, vol. 21 (5), pp. 420-424.

Lin B., et al., "Use of Oligonucleotide Microarrays for Rapid Detection and Serotyping of Acute Respiratory Disease-Associated Adenoviruses," Journal of Clinical Microbiology, 2004, vol. 42 (7), pp. 3232-3239.

Lin P.H., et al., "Oxidative Damage to Mitochondrial Dna in Atrial Muscle of Patients with Atrial Fibrillation," Free Radical Biology and Medicine, 2003, vol. 35 (10), pp. 1310-1318.

Lina G., et al., "Bacterial Competition for Human Nasal Cavity Colonization: Role of Staphylococcalagr Alleles," Applied and Environmental Microbiology, 2003, vol. 69 (1), pp. 18-23.

Lina G., et al., "Involvement of Panton-Valentine Leukocidin-Producing *Staphylococcus aureus* in Primary Skin Infections and Pneumonia," Clinical Infectious Diseases, 1999, vol. 29 (5), pp. 1128-1132.

Linssen B., et al., "Development of Reverse Transcription—PCR Assays Specific for Detection of Equine Encephalitis Viruses," Journal of Clinical Microbiology, 2000, vol. 38 (4), pp. 1527-1535.

Little D.P., et al., "MALDI on a Chip: Analysis of Arrays of Low-Femtomole to Subfemtomole Quantities of Synthetic Oligonucleotides and DNA Diagnostic Products Dispensed by a Piezoelectric Pipet," Analytical Chemistry, 1997, vol. 69, pp. 4540-4546.

Little D.P., et al, "Rapid Sequencing of Oligonucleotides by High-Resolution Mass Spectrometry," Journal of the American Chemical Society, 1994, vol. 116 (11), pp. 4893-4897.

Liu C., et al., "Improving the Microdialysis Procedure for Electrospray Ionization Mass Spectrometry of Biological Samples," Journal of Mass Spectrometry, 1997, vol. 32 (4), pp. 425-431.

Liu J.H., et al., "Interregional Transmission of the Internal Protein Genes of H2 Influenza Virus in Migratory Ducks from North America to Eurasia," Virus Genes, 2004, vol. 29 (1), pp. 81-86.

Liu Y., et al., "An Unusual Gene Arrangement for the Putative Chromosome Replication Origin and Circadianexpression of dnaN in *Synechococcus* sp. Strain PCC 7942," Gene, 1996, vol. 172 (1), pp. 105-109.

Livermore D.M., "The Threat from the Pink Corner," Annals of Medicine, 2003, vol. 35 (4), pp. 226-234.

Loakes D., et al., "Nitroindoles as Universal Bases," Nucleosides and Nucleotides, 1995, vol. 14 (3-5), pp. 1001-1003.

Loo J.A., et al., "Applying Charge Discrimination with Electrospray Ionization-Mass Spectrometry to Protein Analysis," Journal of American Society for Mass Spectrometry, 1995, vol. 6, pp. 1098-1104.

Lott T.J., et al., "Nucleotide Sequence Analysis of the 5-8s rDNA and Adjacent ITS2 Region of Candidaalbicans and Related Species," Yeast, 1993, vol. 9, pp. 1199-1206.

Louie L., et al., "Evaluation of Three Rapid Methods for Detection of Methicillin Resistance in *Staphylococcus aureus*," Journal of Clinical Microbiology, 2000, vol. 38 (6), pp. 2170-2173.

Love B.C., et al., "Cloning and Sequence of the GroESL Heat-Shock Operon of Pasteurella Multocida," Gene, 1995, vol. 166 (1), pp. 179-180.

Lovseth A., et al., "Modified Multiplex PCR Method for Detection of Pyrogenic Exotoxin Genes in Staphylococcal Isolates," Journal of Clinical Microbiology, 2004, vol. 42 (8), pp. 3869-3872.

Lowe T., et al., "A Computer Program for Selection of Oligonucleotide Primers for Polymerase Chain Reactions," Nucleic Acids Research, 1990, vol. 18 (7), pp. 1757-1761.

Lu X., et al., "Molecular Typing of Human Adenoviruses by PCR and Sequencing of a Partial Region of the Hexon Gene," Archives of Virology, 2006, vol. 151 (8), pp. 1587-1602.

Lubman D.M., Application for Continuation Grant by David Mitchell Lubman dated Jun. 4, 1996 and Jun. 14, 1996.

Lubman D.M., Application for Continuation Grant by David Mitchell Lubman dated Jun. 10, 1994 and Jun. 24, 1994.

Lubman D.M., Application for Grant by David Mitchell Lubman dated Sep. 1, 1994 and Sep. 27, 1994.

Lubman D.M., Application for Grant by David Mitchell Lubman dated Oct. 25, 1992 and Oct. 29, 1992.

Ludwig S.L., et al., "Prevalence of Antibodies to Adenovirus Serotypes 4 and 7 among Unimmunized US Army Trainees: Results of a Retrospective Nationwide Seroprevalence Survey," The Journal of Infectious Diseases, 1998, vol. 178 (6), pp. 1776-1778.

Ludwig W., et al., "Bacterial Phylogeny Based on 16S and 23S rRNA Sequence Analysis," FEMS Microbiolofy Reviews, 1994, vol. 15 (2-3), pp. 155-173.

Lukashov V.V., et al., "Evolutionary Relationships among Parvoviruses: Virus-Host Coevolution among Autonomous Primate Parvoviruses and Links between Adeno-Associated and Avian Parvoviruses," Journal of Virology, 2001, vol. 75 (6), pp. 2729-2740.

Ma X.X., et al., "Novel Type of Staphylococcal Cassette Chromosome mec Identified in Community-Acquired Methicillin-Resistant *Staphylococcus aureus* Strains," Antimicrobial Agents and Chemotherapy, 2002, vol. 46 (4), pp. 1147-1152.

Mack D.H., et al., "A Sensitive Method for the Identification of Uncharacterized Viruses Related Toknown Virus Groups: Hepadnavirus Model System," Proceedings of the National Academy of Sciences, 1988, vol. 85 (18), pp. 6977-6981.

Magnuson V.L., et al., "Substrate Nucleotide-Determined Non-Templated Addition of Adenine by TagDNA Polymerase: Implications for PCR-Based Genotyping and Cloning," BioTechniques, 1996, vol. 21 (4), pp. 700-709.

Maiwald M., et al., "Characterization of Contaminating DNA in Taq Polymerase which Occurs During Amplification with a Primer Set for Legionella 5S Ribosomal RNA," Molecular and Cellular Probes, 1994, vol. 8 (1), pp. 11-14.

Malasig M.D., et al., "Simplified Microneutralization Test for Serotyping Adenovirus Isolates," Journal of Clinical Microbiology, 2001, vol. 39 (8), pp. 2984-2986.

Mangrum J.D., et al., "Solution Composition and Thermal Denaturation for the Production of Single-Stranded PCR Amplicons: Piperidine-Induced Destabilization of the DNA Duplex," Journal of the American Society for Mass Spectrometry, 2002, vol. 13 (3), pp. 232-240.

Manian F.A., "Asymptomatic Nasal Carriage of Mupirocin-Resistant, Methicillin-Resistant *Staphylococcus aureus* (MRSA) in a Pet Dog Associated with MRSA Infection in Household Contacts," Clinical Infectious Diseases, 2003, vol. 36 (2), pp. e26-e28.

Marks F., et al., "Genotyping of Plasmodium Falciparum Pyrimethamine Resistance by Matrix-Assisted Laser Desorption-Ionization Time-of-Flight Mass Spectrometry," Antimicrobial Agents and Chemotherapy, 2004, vol. 48 (2), pp. 466-472.

Marmur J., et al., "Strand Separation and Specific Recombination in Deoxyribonucleic Acids: Biological Studies," Proceedings of the National Academy of Sciences, 1960, vol. 46 (4), pp. 453-461.

Martemyanov K.A., et al., "Extremely Thermostable Elongation Factor (3 from Aquifer aeolicus: Cloning, Expression, Purification, and Characterization in a Heterologous Translation System," Protein Expression and Purification, 2000, vol. 18 (3), pp. 257-261.

Martineau F., et al., "Development of a PCR Assay for Identification of *Staphylococci* at Genus andSpecies Levels," Journal of Clinical Microbiology, 2001, vol. 39 (7), pp. 2541-2547.

Martineau F., et al., "Species-Specific and Ubiquitous-DNA-Based Assays for Rapid Identification of *Staphylococcus aureus*," Journal of Clinical Microbiology, 1998, vol. 36 (3), pp. 618-623.

Martin-Lopez J.V., et al., "Simultaneous PCR Detection of ica Cluster and Methicillin and Mupirocinresistance Genes in Catheter-Isolated *Staphylococcus*," International Microbiology, 2004, vol. 7 (1), pp. 63-66.

Mason V.P., et al., "Diversity and linkage of Replication and Mobilisation Genes in *Bacillus* Rolling Irclereplicating Plasmids from Diverse Geographical Origins," FEMS Microbiology Ecology, 2002, vol. 42 (2), pp. 235-241.

Matray T.J., et al., "Synthesis and Properties of RNA Analogs-Oligoribonucleotide N3-->p5 Phosphoramidates," Nucleic Acids Research, 1999, vol. 27 (20), pp. 3976-3985.

Matsuoka M., et al., "Characteristic Expression of Three Genes, msr(A), mph(C) and erm(Y), Thatconfer Resistance to Macrolide Antibiotics on *Staphylococcus aureus*," FEMS Microbiology Letters, 2003, vol. 220 (2), pp. 287-293.

May A.C., "Percent Sequence Identity: the Need to be Explicit," Structure, 2004, vol. 12 (5), pp. 737-738.

McCabe K.M., et al., "Bacterial species identification after DNA amplification with a universal primer pair," Molecular Genetics and Metabolism, 1999, vol. 66 (3), pp. 205-211.

McLafferty F.W., et al., "Comparison of Algorithms and Databases for Matching Unknown Mass Spectra," Journal of the American Society for Mass Spectrometry, 1998, vol. 9 (1), pp. 92-95.

McLuckey S.A., et al., "Ion Trap Tandem Mass Spectrometry Applied to Small Multiply Charged Oligonucleotides with a Modified Base," Journal of the American Society for Mass Spectrometry, 1994, vol. 5, pp. 740-747.

Mehrotra M., et al., "Multiplex PCR for Detection of Genes for *Staphylococcus aureus* Enterotoxins, Exfoliative Toxins, Toxic Shock Syndrome Toxin 1, and Methicillin Resistance," Journal of Clinical Microbiology, 2000, Vol. 38 (3), pp. 1032-1035.

Meiyu F., et al., "Detection of Flaviviruses by Reverse Transcriptase-Polymerase Chain Reaction with the Universal Primer Set," Microbiology and Immunology, 1997, vol. 41 (3), pp. 209-213.

Mellor J., et al., "Genotype Dependence of Hepatitis C Virus Load Measurement in Commercially Available Quantitative Assays," Journal of Clinical Microbiology, 1999, vol. 37 (8), pp. 2525-2532.

Merlino J., et al., "New Chromogenic Identification and Detection of *Staphylococcus aureus* andMethicillin-Resistant *S. Aureus*," Journal of Clinical Microbiology, 2000, vl. 38 (6), pp. 2378-2380.

Merlino J., et al., "Rapid Detection of Non-Multidrug-Resistant and Multidrug-Resistant Methicillin—Resistant *Staphylococcus aureus* Using Cycling Probe Technology for the mecA Gene," European Journal of Clinical Microbiology & Infectious Diseases, 2003, vol. 22 (5), pp. 322-323.

Messmer T.O., et al., "Discrimination of *Streptococcus pneumoniae* from Other Upper respiratory tract Streptococci by arbitrary primed PCR," Clinical Biochemistry, 1995, vol. 28 (6), pp. 567-572.

Metzgar D., et al., "PCR Analysis of Egyptian Respiratory Adenovirus Isolates, Including Identification of Species, Serotypes and Coinfections," Journal of Clinical Microbiology, 2005, vol. 43 (11), pp. 5743-5752.

Miller K.W., et al., "A Compendium of Human Mitochondria! DNA Control Region: Development of an International Standard Forensic Database," Croatian Medical Journal, 2001, vol. 42 (3), pp. 315-327.

Miragaia M., et al., "Genetic Diversity among Methicillin-Resistant *Staphylococcus epidemidis*(MRSE," Microbial Drug Resistance, 2005, vol. 11 (2), pp. 83-93.

Miura-Ochiai R., et al., "Quantitative Detection and Rapid Identification of Human Adenoviruses," Journal of Clinical Microbiology, 2007, vol. 45 (3), pp. 958-967.

Mollet C., et al., "rpoB Sequence Analysis as a Novel Basis for Bacterial Identification," Molecular Microbiology, 1997, vol. 26 (5), pp. 1005-1011.

Monroy A.M., et al., "Exvaluation of Reverse Transcriptase Polymerase Chain Reaction for theDetection of Eastern Equine Encephalumyelitis Virus during Vector Surveillance," Journal of Medical Entomology, 1996, Vol. 33 (3), pp. 449-457.

Moore C., et al., "Development and Evaluation of a Real-Time Nucleic Acid Sequence Based Amplification Assay for Rapid Detection of Influenza A," Journal of Medical Virology, 2004, vol. 74 (4), pp. 619-628.

Moricca S., et al., "Detection of Fusarium Oxysporum f.sp. Vasinfectum in Cotton Tissue by Polymerase Chain Reaction," Plant Pathology, 1998, vol. 47 (4), pp. 486-494.

Morinaga N., et al., "Purification, Cloning and Charactarizarion of Variant LukE-LukD with Strong Leukocidal Activity of Staphylococcal Bi-Component Leukotoxin Family," Microbiology and Immunology, 2003, vol. 47 (1), pp. 81-90.

Morse R., et al., "Nucleotide Sequence of Part of the ropC Gene Encoding the B Subunit of DNADependentRNA Polymerase from some Gram-Positive Bacteria and Comparative Amino AcidSequence Analysis," Systematic and Applied Microbiology, 1996, vol. 19, pp. 150-157.

Muddiman D.C., et al., "Application of Secondary Ion and Matrix-Assisted Laser Desorption-Ionization Time-of-Flight Mass Spectrometry for the Quantitative Analysis of Biological Molecules," Mass Spectrometry Reviews, 1995, vol. 14 (6), pp. 383-429.

Muddiman D.C., et al., "Characterization of PCR Products from Bacilli Using Electrospray Ionization FTICR Mass Spectrometry," Analytical Chemistry, 1996, vol. 68 (21), pp. 3705-3712.

Muddiman D.C., et al., "Important Aspects Concerning the Quantification of Biomolecules by Time-of-Flight Secondaryion Mass Spectrometry," Applied Spectrometry, 1996, vol. 50 (2), pp. 161-166.

Muddiman D.C., et al., "Length and Base Composition of PCR-Amplified Nucleic Acids Using Mass Measurements from Electrospray Ionization Mass Spectrometry," Analytical Chemistry, 1997, vol. 69 (8), pp. 1543-1549.

Muddiman D.C., et al., "Precise Mass Measurement of a Double-Stranded 500 Base-(309 kDa) Polymerase Chain Reaction Product by Negative Ion Electrospray Ionization Fourier Transform Ion Cyclotron Resonance Mass Spectrometry," Rapid Communications in Mass Spectrometry, 1999, vol. 13 (2), pp. 1201-1204.

Muddiman D.C., et al., "Sequencing and Characterization of Larger Oligonucleotides by Electrospray Ionization Fourier Transform Ion Cyclotron Resonance Mass Spectrometry," Reviews in Analytical Chemistry, 1998, vol. 17 (1), pp. 1-68.

Muhammed W.T., et al., "Electrospray Ionization Quadrupole Time-of-Flight Mass Spectrometry and Guadrupole Mass Spectrometry for Genotyping Single Nucleotide Substitutions in Intact Polymerase Chain Reaction Products in K-Ras and p53," Rapid Communications in Mass Spectrometry, 2002, vol. 16 (24), pp. 2278-2285.

Murakami K., et al., "Identification of Methicillin-Resistant Strains of Staphylococci by PolymeraseChain Reaction," Journal of Clinical Microbiology, 1991, vol. 29 (10), pp. 2240-2244.

Mushegian A.R., et al., "A Minimal Gene Set for Cellular Life Derived by Comparison of Complete Bacterial Genomes," Proceedings of the National Academy of Science, 1996, vol. 93 (19), pp. 10268-10273.

Na B.K., et al., "Detection and Typing of Respiratory Adenoviruses in a Single-Tube Multiplex Polymerase Chain Reaction," Journal of Medical Virology, 2002, vol. 66 (4), pp. 512-517.

Nagpal M.L., et al., "Utility of 16S-23S rRNA Spacer Region Methodology: How Similar are Interspace Regions within a Genome and Between Strains for Closely Related Organisms?," Journal of Microbiological Methods, 1998, vol. 33, pp. 211-219.

Nagy M., et al., "Sequence Analysis of Porcine Adenovirus Serotype 5 Fibre Gene: Evidence for Recombination," Virus Genes, 2002, vol. 24 (2), pp. 181-185.

Naito Y., et al., "Molecular Mass Measurement of Polymerase Chain Reaction Products Amplified from Human Blood DNA by Electrospray Ionization Mass Spectrometry," Rapid Communications in Mass Spectrometry, 1995, vol. 9 (15), pp. 1484-1486.

Nakagawa S., et al., "Gene sequences and specific detection for Panton-Valentine leukocidin," Biochemical and Biophysical Research Communications, 2005, vol. 328 (4), pp. 995-1002.

Nakao H., et al., "Development of a Direct PCR Assay for Detection of the Diphtheria Toxin Gene," Journal of Clinical Microbiology, 1997, vol. 35 (7), pp. 1651-1655.

Narita S., et al., "Phage conversion of Panton-Valentine leukocidin in *Staphylococcus aureus*: molecular analysis of a PVL-converting phage, cpSLT," Gene, 2001, vol. 268 (1-2), pp. 195-206.

Naumov G.I., et al., "Discrimination between the soil yeast species Williopsis saturnus and Williopsis suaveolens by the polymerase chain reaction with the universal primer N21," Microbiology, 2000, vol. 69 (2), pp. 229-233.

NEB Catalog. 1998/1999 pp. 1, 79, 121 and 284.

Neumann G., et al., "Host Range Restriction and Pathogenicity in the Context of Influenza Pandemic," Emerging Infectious Diseases, 2006, vol. 12 (6), pp. 881-886.

Newcombe J., et al., "PCR of Peripheral Blood for Diagnosis of Meningococcal Disease," Journal of Clinical Microbiology, 1996, vol. 34 (7), pp. 1637-1640.

Ng E.K., et al., "Quantitative Analysis an Prognostic Implication of SARS Coronavirus Rna in the Plasma and Serum of Patients with Severe Acute Respiratory Syndrome," Clinical Chemistry, 2003, vol. 49 (12), pp. 1976-1980.

Ng E.K., et al., "Serial Analysis of the Plasma Concentration of SARS Coronavirus RNA in Pediatric Patients with Severe Acute Respiratory Syndrome," Clinical Chemistry, 2003, vol. 49 (12), pp. 2085-2088.

Ni J., et al., "Interpretation of Oligonucleotide Mass Spectra for Determinationof Sequence Using Electrospray Ionization and Tandem Mass Spectrometry," Analytical Chemistry, 1996, vol. 68 (13), pp. 1989-1999.

Nilsson M., et al., "Evaluation of Mitochondrial DNA Coding Region Assays for Increased Discrimination in Forensic Analysis," Forensic Science International: Genetics, 2008, vol. 2 (1), pp. 1-8.

Nishikawa T., et al., "Reconstitution of Active Recombinant Ship Toxin (Stc)1 from Recombinant Stxl—A and Sbtl—B Subunits Independently Produced by *E. coli* Clones," FEMS Microbiol Letters, 1999, vol. 178 (1), pp. 13-18.

Non-Final Office Action mailed Feb. 2, 2007 for U.S. Appl. No. 10/844,938, filed May 12, 2004.

Non-Final Office Action mailed Oct. 2, 2009 for U.S. Appl. No. 11/929,707, filed Oct. 30, 2007.

Non-Final Office Action mailed Aug. 4, 2010 for U.S. Appl. No. 12/049,949, filed Mar. 17, 2008.

Non-Final Office Action mailed Apr. 6, 2009 for U.S. Appl. No. 11/331,987, filed Jan. 13, 2006.

Non-Final Office Action mailed Apr. 7, 2006 for U.S. Appl. No. 10/964,571, filed Oct. 12, 2004.

Non-Final Office Action mailed Aug. 7, 2007 for U.S. Appl. No. 10/844,938, filed May 12, 2004.

Non-Final Office Action mailed Jun. 10, 2009 for U.S. Appl. No. 10/844,938, filed May 12, 2004.

Non-Final Office Action mailed Jan. 12, 2010 for U.S. Appl. No. 11/491,376, filed Jul. 21, 2006.

Non-Final Office Action mailed Oct. 13, 2010 for U.S. Appl. No. 10/754,415, filed Jan. 9, 2004.

Non-Final Office Action mailed Sep. 16, 2009 for U.S. Appl. No. 11/233,630, filed Sep. 21, 2005.

Non-Final Office Action mailed Apr. 17, 2009 for U.S. Appl. No. 12/211,641, filed Sep. 16, 2008.

Non-Final Office Action mailed Nov. 19, 2003 for U.S. Appl. No. 09/798,007, filed Mar. 2, 2001.

Non-Final Office Action mailed Aug. 20, 2007 for U.S. Appl. No. 11/582,863, filed Oct. 17, 2006.

Non-Final Office Action mailed May 20, 2008 for U.S. Appl. No. 10/844,938, filed May 12, 2004.

Non-Final Office Action mailed Oct. 20, 2004 for U.S. Appl. No. 09/891,793, filed Jun. 26, 2001.

Non-Final Office Action mailed Feb. 23, 2009 for U.S. Appl. No. 10/660,122, filed Sep. 11, 2003.

Non-Final Office Action mailed May 26, 2010 for U.S. Appl. No. 11/869,449, filed Oct. 9, 2007.

Non-Final Office Action mailed Jul. 27, 2006 for U.S. Appl. No. 11/209,439, filed Aug. 8, 2005.

Non-Final Office Action mailed Jun. 28, 2010 for U.S. Appl. No. 11/930,002, filed Oct. 30, 2007.

Non-Final Office Action mailed Sep. 28, 2009 for U.S. Appl. No. 11/930,017, filed Oct. 30, 2007.

Non-Final Office Action mailed Dec. 29, 2010 for U.S. Appl. No. 12/616,422, filed Nov. 11, 2009.

Non-Final Office Action mailed Apr. 30, 2010 for U.S. Appl. No. 11/930,108, filed Oct. 31, 2007.

Norder H., et al., "Typing of Hepatitis B Virus Genomes by a Simplified Polymerase Chain Reaction," Journal of Medical Virology, 1990, vol. 31 (3), pp. 215-221.

Nordhoff E., et al., "Matrix Assisted Laser Desorption/Ionization Mass Spectrometry of Nucleic Acids with Wavelengths in the Ultraviolet and Infrared," Rapid Communications in Mass Spectrometry, 1992, vol. 6 (12), pp. 771-776.

Notice of Allowance mailed Jun. 3, 2009 for U.S. Appl. No. 11/331,978, filed Jan. 13, 2006.

Notice of Allowance mailed Aug. 5, 2010 for U.S. Appl. No. 11/233,630, filed Sep. 21, 2005.

Notice of Allowance mailed Aug. 6, 2009 for U.S. Appl. No. 10/728,486, filed Dec. 5, 2003.

Notice of Allowance mailed Dec. 10, 2010 for U.S. Appl. No. 11/233,630, filed Sep. 21, 2005.

Notice of Allowance mailed Dec. 10, 2010 for U.S. Appl. No. 11/491,376, filed Jul. 21, 2006.

Notice of Allowance mailed Nov. 12, 2009 for U.S. Appl. No. 10/728,486, filed Dec. 5, 2003.

Notice of Allowance mailed Dec. 15, 2008 for U.S. Appl. No. 11/331,978, filed Jan. 13, 2006.

Notice of Allowance mailed Sep. 18, 2009 for U.S. Appl. No. 10/660,998, filed Sep. 12, 2003.

Notice of Allowance mailed Nov. 24, 2009 for U.S. Appl. No. 11/331,978, filed Jan. 13, 2006.

Notice of Allowance mailed Oct. 29, 2009 for U.S. Appl. No. 10/660,122, filed Sep. 11, 2003.

Nubel U., et al., "PCR primers to amplify 16S rRNA genes from Cyanobacteria," Applied and Environmental Microbiology, 1997, vol. 63 (8), pp. 3327-3332.

Null Allison P., et al., "Enzymatic Strategies for the Characterization of Nucleic Acids by Electrospray Ionization Mass Spectrometry," Rapid Communications in Mass Spectrometry, 2003, vol. 17 (24), pp. 2699-2706.

Null A.P., et al., "Determination of a Correction to Improve Mass Measurement Accuracy of Isotopically Unresolved Polymerase Chain Reaction Amplicons by Electrospray Ionization Fourier Transform Ion Cyclotron Resonance Mass Spectrometry," Rapid Communications in Mass Spectrometry, 2003, vol. 17 (15), pp. 1714-1722.

Null A.P., et al., "Evaluation of Sample Preparation Techniques for Mass Measurements of PCR Products Using ESIFT- ICR Mass Spectrometry," The American Society for Mass Spectrometry, 2002, vol. 13 (4), pp. 338-344.

Null A.P., et al., "Genotyping of Simple and Compound Short Tandem Repeat Loci Using Electrospray Ionization Fourier Transform Ion Cyclotron Resonance Mass Spectrometry," Analytical Chemistry, 2001, vol. 73 (18), pp. 4514-4521.

Null A.P., et al., "Implications of Hydrophobicity and Free Energy of Solvation for Characterization of Nucleic Acids by Electrospray Ionization Mass Spectrometry," Analytical Chemistry, 2003, vol. 75 (6), pp. 1331-1339.

Null A.P., et al., "Perspectives on the Use of Electrospray Ionization Fourier Transform Ion Cyclotron Resonance Mass Spectrometry for Short Tandem Repeat Genotyping in the Post Genome Era," Journal of Mass Spectrometry, 2001, vol. 36 (6), pp. 589-606.

Null A.P., et al., "Preparation of Single-Stranded PCR Products for Electrospray Ionization Mass Spectrometry Using the DNA Repair Enzyme Lambda Exonuclease," Analyst, 2000, vol. 125 (4), pp. 619-626.

Nunes E.L., et al., "Detection of ileS-2 Gene Encoding Mupirocin Resistance in Methicillin-Resistant*Staphylococcus aureus* by Multiplex PCR," Diagnostic Microbiology and Infectious Disease, 1999, vol. 34 (2), pp. 77-81.

Nygren M., et al., "Quantification of HIV-1 Using Multiple Quantitative Polymerase Chain ReactionStandards and Bioluminometric Detection," Analytical Biochemistry, 2001, vol. 288 (1), pp. 28-38.

Oberacher H., et al., "Analysis of Polymerase Chain Reaction Products by On-Line Liquid Chromatography Mass Spectrometry for Genotyping of Polymeric Short tandem Repeat Loci," Analytical Chemistry, 2001, vol. 73 (21), pp. 5109-5115.

Oberacher H., et al., "Increased foresnic efficiency of DNA fingerprints through simultaneous resolution of length and nucleotide variability by high-performance mass spectrometry," Human Mutation, 2008, vol. 29 (3), pp. 427-432.

Oberste M.S., et al., "Improved molecular identification of enteroviruses by RT-PCR and amplicon sequencing," Journal of Medical Virology, 2003, vol. 26 (3), pp. 375-377.

Oberste M.S., et al., "Molecular epidemiology and type-specific detection of echovirus 11 isolates fromthe Americas, Europe, Africa, Australia, southern Asia and the Middle East," Virus Research, 2003, vol. 91 (2), pp. 241-248.

Oberste M.S., et al., "Molecular phylogeny and proposed classification of the Simian picornaviruses," Journal of Virology, 2002, vol. 76 (3), pp. 1244-1251.

Office Action mailed Mar. 23, 2009 for U.S. Appl. No. 10/418,514, filed Apr. 18, 2003.

Office Action mailed Apr. 1, 2004 for U.S. Appl. No. 10/156,608, filed May 24, 2002.

Office Action mailed Jul. 1, 2008 for U.S. Appl. No. 10/418,514, filed Apr. 18, 2003.

Office Action mailed May 1, 2006 for U.S. Appl. No. 10/660,998, filed Sep. 12, 2003.

Office Action mailed Feb. 2, 2011 for U.S. Appl. No. 11/869,449, filed Oct. 9, 2007.

Office Action mailed Jan. 2, 2009 for U.S. Appl. No. 11/060,135, filed Feb. 17, 2005.

Office Action mailed Jun. 2, 2006 for U.S. Appl. No. 10/933,928, filed Sep. 3, 2004.

Office Action mailed Jun. 2, 2008 for U.S. Appl. No. 11/331,978, filed Jan. 13, 2006.

Office Action mailed Oct. 2, 2008 for U.S. Appl. No. 11/233,630, filed Sep. 21, 2005.

Office Action mailed Aug. 3, 2006 for U.S. Appl. No. 10/660,998, filed Sep. 12, 2003.

Office Action mailed Aug. 3, 2009 for U.S. Appl. No. 11/754,174, filed May 25, 2007.

Office Action mailed Dec. 3, 2003 for U.S. Appl. No. 10/325,527, filed Dec. 18, 2002.

Office Action mailed Feb. 3, 2011 for U.S. Appl. No. 12/326,800, filed Dec. 2, 2008.

Office Action mailed Nov. 3, 2008 for U.S. Appl. No. 10/728,486, filed Dec. 5, 2003.

Office Action mailed Apr. 4, 2008 for U.S. Appl. No. 10/829,826, filed Apr. 22, 2004.

Office Action mailed Dec. 4, 2006 for Indian Application No. 1136KOLNP2003 filed Mar. 4, 2002.

Office Action mailed Feb. 4, 2009 for U.S. Appl. No. 11/404,561, filed Apr. 12, 2006.

Office Action mailed Jun. 4, 2009 for U.S. Appl. No. 10/754,415, filed Jan. 9, 2004.

Office Action mailed May 4, 2010 for U.S. Appl. No. 90/010,447, filed Apr. 9, 2009.

Office Action mailed May 4, 2010 for U.S. Appl. No. 90/010,448, filed Apr. 9, 2009.

Office Action mailed Nov. 4, 2009 for European Application No. 02709785.6 filed Mar. 4, 2002.

Office Action mailed Sep. 4, 2008 for Australian Application No. 2003297687 filed Dec. 5, 2003.

Office Action mailed Aug. 5, 2010 for European Application No. 02709785.6 filed Mar. 4, 2002.

Office Action mailed Sep. 5, 2006 for U.S. Appl. No. 10/660,996, filed Sep. 12, 2003.

Office Action mailed Dec. 6, 2007 for U.S. Appl. No. 10/418,514, filed Apr. 18, 2003.

Office Action mailed Jan. 6, 2011 for Israel Application No. 157661 filed Mar. 4, 2002.

Office Action mailed Jul. 6, 2006 for U.S. Appl. No. 10/660,122, filed Sep. 11, 2003.

Office Action mailed Jul. 6, 2007 for U.S. Appl. No. 10/829,826, filed Apr. 22, 2004.

Office Action mailed Mar. 6, 2009 for U.S. Appl. No. 11/233,630, filed Sep. 21, 2005.

Office Action mailed Nov. 6, 2002 for U.S. Appl. No. 09/798,007, filed Mar. 2, 2001.

Office Action mailed Apr. 7, 2009 for Canadian Application No. 2525498 filed May 13, 2004.

Office Action mailed Apr. 7, 2009 for European Application No. 07760292.8 filed Apr. 6, 2007.

Office Action mailed Apr. 7, 2009 for U.S. Appl. No. 10/660,998, filed Sep. 12, 2003.

Office Action mailed Aug. 7, 2007 for U.S. Appl. No. 10/660,998, filed Sep. 12, 2003.

Office Action mailed Feb. 7, 2008 for European Application No. 03796752.8 filed Dec. 5, 2003.

Office Action mailed Jun. 7, 2010 for European Application No. 06800205.4 filed Jul. 27, 2006.

Office Action mailed Jan. 8, 2003 for U.S. Appl. No. 09/798,007, filed Mar. 2, 2001.

Office Action mailed Jan. 8, 2007 for U.S. Appl. No. 09/891,793, filed Jun. 26, 2001.

Office Action mailed Mar. 8, 2005 for U.S. Appl. No. 09/891,793, filed Jun. 26, 2001.

Office Action mailed Mar. 8, 2007 for U.S. Appl. No. 11/060,135, filed Feb. 17, 2005.

Office Action mailed Sep. 8, 2006 for Chinese Application No. 02809122.1 filed Mar. 4, 2002.

Office Action mailed Dec. 9, 2004 for U.S. Appl. No. 10/156,608, filed May 24, 2002.

Office Action mailed Dec. 9, 2009 for U.S. Appl. No. 90/010,210, filed Jun. 27, 2008.

Office Action mailed Dec. 9, 2009 for U.S. Appl. No. 90/010,447, filed Apr. 9, 2009.

Office Action mailed Dec. 9, 2009 for U.S. Appl. No. 90/010,448, filed Apr. 9, 2009.
Office Action mailed Feb. 9, 2007 for Chinese Application No. 02809122.1 filed Mar. 4, 2002.
Office Action mailed Jan. 9, 2008 for Japanese Application No. 2002570692 filed Mar. 4, 2002.
Office Action mailed Jul. 9, 2008 for U.S. Appl. No. 10/660,122, filed Sep. 11, 2003.
Office Action mailed Jul. 9, 2008 for U.S. Appl. No. 11/331,987, filed Jan. 13, 2006.
Office Action mailed Mar. 9, 2004 for U.S. Appl. No. 09/891,793, filed Jun. 26, 2001.
Office Action mailed Nov. 9, 2010 for U.S. Appl. No. 11/331,987, filed Jan. 13, 2006.
Office Action mailed Aug. 10, 2004 for U.S. Appl. No. 09/891,793, filed Jun. 26, 2001.
Office Action mailed Aug. 10, 2004 for U.S. Appl. No. 09/798,007, filed Mar. 2, 2001.
Office Action mailed Aug. 10, 2004 for U.S. Appl. No. 10/156,608, filed May 24, 2002.
Office Action mailed Aug. 10, 2004 for U.S. Appl. No. 10/326,642, filed Dec. 18, 2002.
Office Action mailed Dec. 10, 2008 for U.S. Appl. No. 10/829,826, filed Apr. 22, 2004.
Office Action mailed Dec. 10, 2009 for U.S. Appl. No. 11/929,910, filed Oct. 30, 2007.
Office Action mailed Feb. 10, 2005 for U.S. Appl. No. 09/798,007, filed Mar. 2, 2001.
Office Action mailed Feb. 10, 2006 for Australian Application No. 2002244250 filed Mar. 4, 2002.
Office Action mailed Jun. 10, 2009 for U.S. Appl. No. 90/010,210, filed Jun. 27, 2008.
Office Action mailed Jun. 10, 2010 for U.S. Appl. No. 90/010,447, filed Apr. 9, 2009.
Office Action mailed Jun. 10, 2010 for U.S. Appl. No. 90/010,448, filed Apr. 9, 2009.
Office Action mailed Oct. 10, 2007 for U.S. Appl. No. 10/754,415, filed Jan. 9, 2004.
Office Action mailed Sep. 10, 2008 for Australian Application No. 2003302236 filed Dec. 5, 2003.
Office Action mailed Aug. 11, 2005 for U.S. Appl. No. 09/891,793, filed Jun. 26, 2001.
Office Action mailed Aug. 11, 2010 for U.S. Appl. No. 90/010,447, filed Apr. 9, 2009.
Office Action mailed Aug. 11, 2010 for U.S. Appl. No. 90/010,448, filed Apr. 9, 2009.
Office Action mailed Dec. 11, 2007 for U.S. Appl. No. 10/660,998, filed Sep. 12, 2003.
Office Action mailed Jul. 11, 2003 for U.S. Appl. No. 09/798,007, filed Mar. 2, 2001.
Office Action mailed Jun. 11, 2010 for U.S. Appl. No. 90/010,210, filed Jun. 27, 2008.
Office Action mailed Mar. 11, 2005 for U.S. Appl. No. 10/325,527, filed Dec. 18, 2002.
Office Action mailed May 11, 2007 for U.S. Appl. No. 10/728,486, filed Dec. 5, 2003.
Office Action mailed Feb. 12, 2009 for U.S. Appl. No. 11/136,134, filed May 24, 2005.
Office Action mailed Jul. 12, 2006 for U.S. Appl. No. 09/891,793, filed Jun. 26, 2001.
Office Action mailed Jul. 12, 2006 for U.S. Appl. No. 10/660,996, filed Sep. 12, 2003.
Office Action mailed Jun. 12, 2008 for U.S. Appl. No. 10/754,415, filed Jan. 9, 2004.
Office Action mailed Jun. 12, 2009 for Chinese Application No. 200480016187.9 filed May 13, 2004.
Office Action mailed Mar. 12, 2008 for European Application No. 06849755.1 filed Apr. 12, 2006.
Office Action mailed May 12, 2002 for U.S. Appl. No. 09/798,007, filed Mar. 2, 2001.
Office Action mailed Aug. 13, 2009 for U.S. Appl. No. 11/674,538, filed Feb. 13, 2007.
Office Action mailed Jul. 13, 2004 for U.S Appl. No. 09/891,793, filed Jun. 26, 2001.
Office Action mailed Jul. 13, 2007 for U.S. Appl. No. 11/233,630, filed Sep. 21, 2005.
Office Action mailed Jul. 13, 2010 for U.S. Appl. No. 11/929,930, filed Oct. 30, 2007.
Office Action mailed Mar. 13, 2006 for U.S. Appl. No. 10/754,415, filed Jan. 9, 2004.
Office Action mailed Nov. 13, 2003 for U.S. Appl. No. 09/891,793, filed Jun. 26, 2001.
Office Action mailed Sep. 13, 2006 for U.S. Appl. No. 09/891,793, filed Jun. 26, 2001.
Office Action mailed Jul. 14, 2004 for U.S. Appl. No. 10/326,642, filed Dec. 18, 2002.
Office Action mailed Jun. 14, 2004 for U.S. Appl. No. 09/891,793, filed Jun. 26, 2001.
Office Action mailed Mar. 14, 2011 for U.S. Appl. No. 11/930,002, filed Oct. 30, 2007.
Office Action mailed Apr. 15, 2008 for U.S. Appl. No. 10/418,514, filed Apr. 18, 2003.
Office Action mailed Aug. 15, 2008 for U.S. Appl. No. 11/331,978, filed Jan. 13, 2006.
Office Action mailed Dec. 15, 2008 for Israel Application No. 157661 filed Mar. 4, 2002.
Office action mailed Dec. 15, 2010 for Canadian Application No. 2508726 filed Dec. 5, 2003.
Office Action mailed Jan. 15, 2008 for Israel Application No. 157661 filed Mar. 4, 2002.
Office Action mailed Jul. 15, 2009 for U.S. Appl. No. 11/060,135, filed Feb. 17, 2005.
Office Action mailed Mar. 15, 2010 for European Application No. 08730682.5 filed Feb. 25, 2008.
Office Action mailed Nov. 15, 2007 for U.S. Appl. No. 11/331,978, filed Jan. 13, 2006.
Office Action mailed Sep. 15, 2005 for U.S. Appl. No. 10/156,608, filed May 24, 2002.
Office Action mailed Apr. 16, 2002 for U.S. Appl. No. 09/798,007, filed Mar. 2, 2001.
Office Action mailed Apr. 16, 2008 for U.S. Appl. No. 11/233,630, filed Sep. 21, 2005.
Office Action mailed Apr. 16, 2009 for U.S. Appl. No. 90/010,210, filed Jun. 27, 2008.
Office Action mailed Aug. 16, 2004 for U.S. Appl. No. 10/325,527, filed Dec. 18, 2002.
Office Action mailed Aug. 16, 2010 for U.S. Appl. No. 11/929,707, filed Oct. 30, 2007.
Office Action mailed Feb. 16, 2011 for U.S. Appl. No. 11/929,910, filed Oct. 30, 2007.
Office Action mailed Jul. 16, 2007 for U.S. Appl. No. 11/331,987, filed Jan. 13, 2006.
Office Action mailed Mar. 16, 2006 for U.S. Appl. No. 09/891,793, filed Jun. 26, 2001.
Office Action mailed Mar. 16, 2010 for Canadian Application No. 2616281 filed Jul. 21, 2006.
Office Action mailed May 16, 2008 for U.S. Appl. No. 11/404,561, filed Apr. 12, 2006.
Office Action mailed Nov. 16, 2009 for Japanese Application No. 2005508488 filed Dec. 5, 2003.
Office Action mailed Nov. 16, 2009 for Japanese Application No. 2005508560 filed Dec. 5, 2003.
Office Action mailed Jun. 17, 2008 for U.S. Appl. No. 11/582,863, filed Oct. 17, 2006.
Office Action mailed Mar. 17, 2006 for U.S. Appl. No. 10/660,122, filed Sep. 11, 2003.
Office Action mailed Nov. 17, 2006 for U.S. Appl. No. 10/754,415, filed Jan. 9, 2004.
Office Action mailed Oct. 17, 2007 for U.S. Appl. No. 10/728,486, filed Dec. 5, 2003.
Office Action mailed Oct. 17, 2008 for U.S. Appl. No. 11/331,978, filed Jan. 2006.
Office Action mailed Sep. 17, 2008 for European Application No. 03796752.8 filed Dec. 5, 2003.

Office Action mailed Sep. 17, 2008 for U.S. Appl. No. 10/660,122, filed Sep. 11, 2003.
Office Action mailed Feb. 18, 2010 for European Application No. 03814656.9 filed Dec. 5, 2003.
Office Action mailed Jan. 18, 2011 for U.S. Appl. No. 11/930,108, filed Oct. 31, 2007.
Office Action mailed May 18, 2005 for New Zealand Application No. 527857 filed Mar. 4, 2002.
Office Action mailed Sep. 18, 2006 for U.S. Appl. No. 10/660,997, filed Sep. 12, 2003.
Office Action mailed Sep. 18, 2008 for Australian Application No. 2003298030 filed Dec. 5, 2003.
Office Action mailed Sep. 18, 2008 for U.S. Appl. No. 10/660,998, filed Sep. 12, 2003.
Office Action mailed Jan. 19, 2007 for U.S. Appl. No. 11/059,776, filed Feb. 17, 2005.
Office Action mailed May 19, 2005 for U.S. Appl. No. 09/891,793, filed Jun. 26, 2001.
Office Action mailed Nov. 19, 2004 for U.S. Appl. No. 10/156,608, filed May 24, 2002.
Office Action mailed Sep. 19, 2006 for U.S. Appl. No. 10/660,122, filed Sep. 11, 2003.
Office Action mailed Sep. 19, 2007 for U.S. Appl. No. 10/660,122, filed Sep. 11, 2003.
Office Action mailed Apr. 20, 2007 for U.S. Appl. No. 10/660,122, filed Sep. 11, 2003.
Office Action mailed Apr. 20, 2009 for U.S. Appl. No. 10/891,337, filed Jul. 14, 2004.
Office Action mailed Dec. 20, 2006 for U.S. Appl. No. 10/728,486 filed Dec. 5, 2003.
Office Action mailed Jul. 20, 2005 for U.S. Appl. No. 10/156,608, filed May 24, 2002.
Office Action mailed Jun. 20, 2002 for U.S. Appl. No. 09/798,007, filed Mar. 2, 2001.
Office Action mailed Jun. 20, 2007 for U.S. Appl. No. 11/136,134, filed May 24, 2005.
Office Action mailed Nov. 20, 2003 for U.S. Appl. No. 10/323,438, filed Dec. 18, 2002.
Office Action mailed Nov. 20, 2006 for U.S. Appl. No. 09/891,793, filed Jun. 26, 2001.
Office Action mailed Nov. 20, 2006 for European Application No. 02709785.6 filed Mar. 4, 2002.
Office Action mailed Sep. 20, 2010 for U.S. Appl. No. 90/010,447, filed Apr. 9, 2009.
Office Action mailed Sep. 20, 2010 for U.S. Appl. No. 90/010,448, filed Apr. 9, 2009.
Office Action mailed Apr. 21, 2009 for U.S. Appl. No. 90/010,209, filed Jun. 27, 2008.
Office Action mailed Mar. 21, 2008 for U.S. Appl. No. 10/660,122, filed Sep. 11, 2003.
Office Action mailed May 21, 2008 for U.S. Appl. No. 10/943,344, filed Sep. 17, 2004.
Office Action mailed May 21, 2009 for U.S. Appl. No. 11/136,134, filed May 24, 2005.
Office Action mailed Nov. 21, 2003 for U.S. Appl. No. 10/326,642, filed Dec. 18, 2002.
Office Action mailed Nov. 21, 2006 for U.S. Appl. No. 10/660,997, filed Sep. 12, 2003.
Office Action mailed Oct. 21, 2005 for U.S. Appl. No. 10/326,641, filed Dec. 18, 2002.
Office Action mailed Oct. 21, 2009 for U.S. Appl. No. 12/326,800, filed Dec. 2, 2008.
Office Action mailed Apr. 22, 2009 for U.S. Appl. No. 11/491,376, filed Jul. 21, 2006.
Office Action mailed Jul. 22, 2008 for U.S. Appl. No. 90/010,209, filed Jun. 27, 2008.
Office Action mailed Jul. 22, 2008 for U.S. Appl. No. 90/010,210, filed Jun. 27, 2008.
Office Action mailed Nov. 22, 2006 for U.S. Appl. No. 10/660,996, filed Sep. 12, 2003.
Office Action mailed Oct. 22, 2007 for U.S. Appl. No. 11/331,987, filed Jan. 13, 2006.
Office Action mailed Sep. 22, 2003 for U.S. Appl. No. 09/798,007, filed Mar. 2, 2001.
Office Action mailed Sep. 22, 2010 for Canadian Application No. 2510007 filed Dec. 5, 2003.
Office Action mailed Apr. 23, 2010 for U.S. Appl. No. 90/010,210, filed Jun. 27, 2008.
Office Action mailed Feb. 23, 2009 for U.S. Appl. No. 10/943,344, filed Sep. 17, 2004.
Office Action mailed Jan. 23, 2008 for U.S. Appl. No. 10/728,486, filed Dec. 5, 2003.
Office Action mailed Jan. 23, 2008 for U.S. Appl. No. 11/059,776, filed Feb. 17, 2005.
Office Action mailed May 23, 2003 for U.S. Appl. No. 09/891,793, filed Jun. 26, 2001.
Office Action mailed May 23, 2005 for U.S. Appl. No. 10/156,608, filed May 24, 2002.
Office Action mailed Oct. 23, 2003 for New Zealand Application No. 527857 filed Mar. 4, 2002.
Office Action mailed Apr. 24, 2009 for U.S. Appl. No. 90/010,447, filed Apr. 9, 2009.
Office Action mailed Apr. 24, 2009 for U.S. Appl. No. 90/010,448, filed Apr. 9, 2009.
Office Action mailed Aug. 24, 2010 for U.S. Appl. No. 90/010,210, filed Jun. 27, 2008.
Office Action mailed Dec. 24, 2004 for New Zealand Application No. 527857 filed Mar. 4, 2002.
Office Action mailed Feb. 24, 2004 for U.S. Appl. No. 10/326,642, filed Dec. 18, 2002.
Office Action mailed Jan. 24, 2005 for U.S. Appl. No. 10/326,642, filed Dec. 18, 2002.
Office Action mailed Jan. 24, 2007 for U.S. Appl. No. 10/660,998, filed Sep. 12, 2003.
Office Action mailed Jul. 24, 2007 for Mexican Application No. PAA2003007927 filed Sep. 2, 2003.
Office Action mailed Jul. 24, 2007 for U.S. Appl. No. 11/060,135, filed Feb. 17, 2005.
Office Action mailed Jul. 24, 2009 for U.S. Appl. No. 11/754,182, filed May 25, 2007.
Office Action mailed Jun. 24, 2008 for European Application No. 06800205.4 filed Jul. 27, 2006.
Office Action mailed Nov. 24, 2009 for U.S. Appl. No. 90/010,210, filed Jun. 27, 2008.
Office Action mailed Sep. 24, 2009 for U.S. Appl. No. 90/010,210, filed Jun. 27, 2008.
Office Action mailed Aug. 25, 2009 for U.S. Appl. No. 11/754,169, filed May 25, 2007.
Office Action mailed Jun. 25, 2009 for U.S. Appl. No. 11/869,449, filed Oct. 9, 2007.
Office Action mailed Jun. 25, 2009 for U.S. Appl. No. 90/010,210, filed Jun. 27, 2008.
Office Action mailed Mar. 25, 2008 for U.S. Appl. No. 11/060,135, filed Feb. 17, 2005.
Office Action mailed Aug. 26, 2003 for U.S. Appl. No. 09/891,793, filed Jun. 26, 2001.
Office Action mailed Aug. 26, 2010 for Canadian Application No. 2508584 filed Dec. 5, 2003.
Office Action mailed Jul. 26, 2004 for U.S. Appl. No. 10/323,438, filed Dec. 18, 2002.
Office Action mailed Mar. 26, 2008 for U.S. Appl. No. 11/136,134, filed May 24, 2005.
Office Action mailed May 26, 2005 for U.S. Appl. No. 10/156,608, filed May 24, 2002.
Office Action mailed May 26, 2006 for U.S. Appl. No. 10/660,997, filed Sep. 12, 2003.
Office Action mailed Feb. 27, 2003 for U.S. Appl. No. 09/798,007, filed Mar. 2, 2001.
Office Action mailed Feb. 27, 2006 for U.S. Appl. No. 10/418,514, filed Apr. 18, 2003.
Office Action mailed Feb. 27, 2007 for U.S. Appl. No. 10/754,415, filed Jan. 9, 2004.
Office Action mailed Feb. 27, 2007 for U.S. Appl. No. 10/943,344, filed Sep. 17, 2004.

Office Action mailed Jul. 27, 2006 for U.S. Appl. No. 10/728,486, filed Dec. 5, 2003.
Office Action mailed Jul. 27, 2009 for Canadian Application No. 2439655 filed Mar. 4, 2002.
Office Action mailed Mar. 27, 2007 for U.S. Appl. No. 10/418,514, filed Apr.18, 2003.
Office Action mailed Aug. 28, 2006 for U.S. Appl. No. 10/754,415, filed Jan. 9, 2004.
Office Action mailed Feb. 28, 2006 for U.S. Appl. No. 10/660,996, filed Sep. 12, 2003.
Office Action mailed Jul. 28, 2009 for U.S. Appl. No. 11/754,163, filed May 25, 2007.
Office Action mailed Jul. 28, 2010 for U.S. Appl. No. 90/010,210, filed Jun. 27, 2008.
Office Action mailed May 28, 2003 for U.S. Appl. No. 09/798,007, filed Mar. 2, 2001.
Office Action mailed Mar. 29, 2010 for Australian Application No. 2006272776 filed Jul. 21, 2006.
Office Action mailed May 29, 2007 for U.S. Appl. No. 11/059,776, filed Feb. 17, 2005.
Office Action mailed Oct. 29, 2009 for U.S. Appl. No. 90/010,447, filed Apr. 9, 2009.
Office Action mailed Oct. 29, 2009 for U.S. Appl. No. 90/010,448, filed Apr. 9, 2009.
Office Action mailed Sep. 29, 2005 for U.S. Appl. No. 10/418,514 filed Apr. 18, 2003.
Office Action mailed Sep. 29, 2009 for U.S. Appl. No. 10/418,514 filed Apr. 18, 2003.
Office Action mailed Aug. 30, 2007 for U.S. Appl. No. 10/754,415, filed Jan. 9, 2004.
Office Action mailed Jul. 30, 2008 for Australian Application No. 2004248107 filed Apr. 23, 2004.
Office Action mailed Jul. 30, 2009 for Japanese Application No. 2002570692 filed Mar. 4, 2002.
Office Action mailed Jun. 30, 2004 for U.S. Appl. No. 09/798,007, filed Mar. 2, 2001.
Office Action mailed Jun. 30, 2010 for U.S. Appl. No. 90/010,210, filed Jun. 27, 2008.
Office Action mailed Jun. 30, 2010 for U.S. Appl. No. 90/010,447, filed Apr. 9, 2009.
Office Action mailed Jun. 30, 2010 for U.S. Appl. No. 90/010,448, filed Apr. 9, 2009.
Office Action mailed May 30, 2006 for U.S. Appl. No. 10/660,996, filed Sep. 12, 2003.
Office Action mailed Nov. 30, 2009 for U.S. Appl. No. 10/660,122, filed Sep. 11, 2003.
Office Action mailed Sep. 30, 2005 for Chinese Application No. 02809122.1 filed Mar. 4, 2002.
Office Action mailed Jan. 31, 2003 for U.S. Appl. No. 09/798,007, filed Mar. 2, 2001.
Office Action mailed Jan. 31, 2007 for Philippines Application No. PH12003500824 filed Mar. 4, 2002.
Office Action mailed Oct. 31, 2008 for U.S. Appl. No. 11/136,134, filed May 24, 2005.
O'Guinn M.L., et al., "Field Detection of Eastern Equine Encephalitis Virus in the Amazon BasinRegion of Peru Using Reverse Transcription-Polymerase Chain Reaction Adapted for FieldIdentification of Arthropod-Borne Pathogens," American Journal of Tropical Medicine and Hygiene, 2004, vol. 70 (2), pp. 164-171.
Oizumi N., et al., "Relationship between mutations in the DNA gyrase and topoisomerase IV genes and nadifloxacin resistance in clinically isolated quinolone-resistant *Staphylococcus aureus*," Journal of Infection and Chemotherapy, 2001, vol. 7 (3), pp. 191-194.
Okada M., et al., "Detection and sequence-based typing of human adenoviruses using sensitiveuniversal primer sets for the hexon gene," Archives of Virology, 2007, vol. 152 (1), pp. 1-9.
Okuma K., et al., "Dissemination of New Methicillin-Resistant *Staphylococcus aureus* Clones in the Community," Journal of Clinical Microbiology, 2002, vol. 40 (11), pp. 4289-4294.
Oliveira D.C., et al., "Genetic Organization of the Downstream Region of the mecA Element inMethicillin-Resistant Staphylococcus aureus Isolates Carrying Different Polymorphisms of This Region," Antimicrobial Agents and Chemotherapy, 2000, vol. 44 (7), pp. 1906-1910.
Oliveira D.C., et al., "Multiplex PCR Strategy for Rapid Identification of Structural Types and Variants of the mec Element in Methicillin-Resistant *Staphylococcus aureus*," Antimicrobial Agents and Chemotherapy, 2002, vol. 46 (7), pp. 2155-2161.
Olsen B., et al., "Transhemispheric Exchange of Lyme Disease Spyrochetes by Seabirds," Journal of Clinical Microbiology, 1995, vVol. 33 (12), pp. 3270-3274.
Osiowy C., et al., "Direct Detection of Respiratory Syncytial Virus, Parainfluenza Virus, and Adenovirus in Clinical Respiratory Specimens by a Multiplex Reverse Transcription-PCR Assay," Journal of Clinical Microbiology, 1998, vol. 36 (11), pp. 3149-3154.
Ostrander E.A., et al., "Identification and Characterization of Dinucleotide Repeat (CA)n Markers for Genetic Mapping in Dog," Genomics, 1993, vol. 16 (1), pp. 207-213.
Ounissi H., et al., "Gene Homogeneity for Aminoglycoside-Modifying Enzymes in Gram-PositiveCocci," Antimicrobial Agents and Chemotherapy, 1990, vol. 34 (11), pp. 2164-2168.
Palys T., et al., "Discovery and Classification of Ecological Diversity in the Bacterial World: The Role of DNA Sequence Data," International Journal of Systematic Bacteriology, 1997, vol. 47 (4), pp. 1145-1156.
Pan Z.Q., et al., "Oligonucleotide-targeted degradation of U1 and U2 snRNAs reveals differential interactions of simian virus 40 pre-mRNAs with snRNPs," Nucleic Acids Research, 1989, vol. 17 (16), pp. 6553-6568.
Pannetier C., et al., "Quantitative Titration of Nucleic Acids by Enzymatic Amplification Reactions run to Saturation," Nucleic Acids Research, 1993, vol. 21 (3), pp. 577-583.
Parson W., et al., "Population Data for 101 Austrian Caucasian Mitochondrial Dna dLoop Sequences: Application of mtDNA Sequence Analysis to a Forensic Case," International Journal of Legal Medicine, 1998, vol. 111 (3), pp. 124-132.
Partial European Search Report for Application No. EP01106974, mailed on Dec. 16, 2002, 2 pages.
Pastorino B., et al., "Development of a TaqMan PCR assay without Rna extraction step for the detection and quantification of African Chikungunya viruses," Journal of Virological Methods, 2005, vol. 124 (1-2), pp. 65-71.
Paterson A.H., et al., "Fine Mapping of Quantitative Trait Loci Using Selected Overlapping RecombinantChromosomes, in an Interspecies Cross of Tomato," Genetics, 1990, vol. 124 (3), pp. 735-742.
Pawa A., et al., "Co-transfer of plasmids in association with conjugative transfer of mupirocin or mupirocin and penicillin resistance in methicillin-resistant *Staphylococcus aureus*," Journal of Clinical Microbiology, 2000, vol. 49 (12), pp. 1103-1107.
Payne D., et al., "Antimicrobials: The Challenge of Antibiotic Resistant Bacterial Pathogens: The Medical Need, The Market and Prospects for New Antimicrobial Agents," Current Opinion in Microbiology, 2004, vol. 7, pp. 435-438.
Peng X., et al., "Rapid Detection of Shigella Species in Environmental Sewage by an Immunocapture PCR with Universal Primers," Applied and Environmental Microbiology, 2002, vol. 68 (5), pp. 2580-2583.
Perez-Roth E., et al., "Multiplex PCR for Simultaneous Identification of *Staphylococcus aureus* andDetection of Methicillin and Mupirocin Resistance," Journal of Clinical Microbiology, 2001, vol. 39 (11), pp. 4037-4041.
Peters S.E., et al., "Quantification of the detection of Pneumocystis carinii by DNA amplification," Molecular and Cellur Probes, 1992, vol. 6 (2), pp. 115-117.
Pfeffer M., et al., "Genus-Specific Detection of Alphaviruses by a Semi-Nested ReverseTranscription-Polymerase Chain Reaction," American Journal of Tropical Medicine and Hygiene, 1997, vol. 57 (6), pp. 709-718.
Pfeffer M., et al., "Specific Detection of Chikungunya Virus Using a RT-PCR/Nested PCR Combination," Journal of Veterinary Medicine B, 2002, vol. 49 (1), pp. 49-54.
Pieles U., et al., "Matrix-Assisted Laser Desorption Ionization Time-of-Flight Spectrometry: APowerful Tool for the Mass and Sequence Analysis of Natural and Modified Oligonucleotides, 787 reexamination," Nucleic Acids Research, 1993, vol. 21 (14), pp. 3191-3196.
Pillai S.D., et al., "Rapid molecular detection of microbial pathogens: breakthroughs and challenges," Archives of Virology, 1997, vol. 13, pp. 67-82.
Piper J., et al., "Commercially Available Technique for Rapid Laboratory Detection of MethicillinResistance Among *Staphylococcus aureus*," Diagnostic Microbiology and Infectious Disease, 1988, vol. 11 (3), pp. 177-180.
Poddar S.K., et al., "Detection of adenovirus using Pcr and molecular beacon," Journal of Virological Methods, 1999, vol. 82 (1), pp. 19-26.
Pomerantz S.C., et al., "Determination of oligonucleotide composition from mass spectrometrically measured molecular weight," Journal of the American Society for Mass Spectrometry, 1993, vol. 4 (3), pp. 204-209.
Pring-Akerblom P., et al., "Multiplex Polymerase Chain Reaction for Subgenus-Specific Detection of Human Adenoviruses in Clinical Samples," Journal of Medical Virology, 1999, vol. 58 (1), pp. 87-92.
Pring-Akerblom P., et al., "PCR-based detection and typing of human adenoviruses in clinical samples," Research in Virology, 1997, vol. 148 (3), pp. 225-231.
Promega. T4 Polynucleotide Kinase, Technical Bulletin No. 519, 2002.
Puthavathana P., et al., "Molecular characterization of the complete genome of human influenza H5N1 virus Isolates from Thailand," Journal of General Virology, 2005, vol. 86 (2), pp. 423-433.
Qadri S.M., et al., "Rapid Detection of Methicillin-Resistant *Staphylococcus aureus* by CrystalMRSA ID System," Journal of Clinical Microbiology, 1994, vol. 32 (7), pp. 1830-1832.
Raaum R.L., et al., "Catarrhine Primate Divergence Dates Estimated from Complete Mitochondria Genomes: Concordance with Fossil and Nuclear DNA Evidence," Journal of Human Evolution, 2005, vol. 48 (3), pp. 237-257.
Ramisse V., et al., "Identification and characterization of *Bacillus anthracis* by multiplex PCR analysis of sequences on plasmids pX01 and pX02 and chromosomal DNA," FEMS Microbiology Letters, 1996, vol. 145 (1), pp. 9-16.
Reid S.M., et al., "Primary Diagnosis of Foot-and-Mouth Disease by Reverse Transcription Polymerase Chain Reaction," Journal of Virological Methods, 2000, vol. 89 (1-2), pp. 167-176.
Reilly K., et al., "Design and Use of 16s Ribosomal Dna-Directed Primers in Competitive PCRs to Enumerate Proteolytic Bacteria in the Rumen," Microbial Ecology, 2002, vol. 43 (2), pp. 259-270.
Reischl U., "Application of Molecular Biology-Based Methods to theDiagnosis of Infectious Diseases 1, e72-e77.," Frontiers in Bioscience, 1996, vol. 1 (1), pp. e72-e77.
Reischl U., et al., "Rapid Identification of Methicillin-Resistant *Staphylococcus aureus* and Simultaneous Species Confirmation Using Real-Time Fluorescence PCR," Journal of Clinical Microbiology, 2000, vol. 38 (6), pp. 2429-2433.
Roberts M.M., et al., "Three-Dimensional Structure of the Adenovirus Major Coat Protein Hexon," Science, 1986, vol. 232 (4754), pp. 1148-1151.
Roberts M.S., et al., "Recombination and Migration Rates in Natural Populations of *Bacillus subtilis* and Bacillus Mojavensis," Evolution, 1995, vol. 49 (6), pp. 1081-1094.
Robinson D.A., et al., "Multilocus sequence typing and the evolution of methicillin-resistant*Staphylococcus aureus*," Clinical Microbiology and Infection, 2004, vol. 10, pp. 92-97.
Rong S., et al., "Design and Application of 60mer Oligonucleotide Microarray in SARS Coronavirus Detection," Chinese Science Bulletin, 2003, vol. 48 (12), pp. 1165-1169.
Ross P.L., et al., "Analysis of DNA Fragments from Conventional and Microfabricated PCR Devices Using Delayed Extraction MALDI-TOF Mass Spectrometry," Analytical Chemistry, 1998, vol. 70 (10), pp. 2067-2073.
Ross P.L., et al., "Discrimination of Single-Nucleotide Polymorphisms in Human DNA Using Peptide Nucleic Acid Probes Detected by MALDI-TOF Mass Spectrometry," Analytical Chemistry, 1997, vol. 69 (20), pp. 4197-4202.
Rota P.A., et al., "Sequencing of a cDNA clone of the nucleoprotein gene of influenza B/Ann Arbor/1/86," Nucleic Acids Research, 1989, vol. 17 (9), pp. 3595.

Ruan Y., et al., "Comparative full-length genome sequence analysis of 14 SARS coronavirus isolates and common mutations associated with the putative origins of infection," The Lancet, 2003, vol. 361, pp. 1779-1785, 1832.
Ruest A., et al., "Comparison of the Directigen Flu A+B test, the QuickVue Influenza Test, and Clinical Case Definition to Viral Culture and Reverse Transcription-PCR for Rapid Diagnosis of Influenza Virus Infection," Journal of Clinical Microbiology, 2003, vol. 41 (8), pp. 3487-3493.
Rupf S., et al., "Quantitative determination of *Streptococcus mutans* by using competitive polymerasechain reaction," European Journal of Oral Sciences, 1999, vVol. 107 (2), pp. 75-81.
Russell K.L., et al., "Transmission Dynamics and Prospective Environmental Sampling of Adenovirus in a Military Recruit Setting," Journal of Infectious Diseases, 2006, vol. 194 (7), pp. 877-885.
Sabat A., et al., "Comparison of PCR-Based Methods for Typing *Staphylococcus aureus* Isolates" Journal of Clinical Microbiology, 2006, vol. 44 (10), pp. 3804-3807.
Sackesen C., et al., "Use of polymerase chain reaction for detection of adenovirus in children withor without wheezing," Turkish Journal of Pediatrics, 2005, vol. 47 (3), pp. 227-231.
Sakai H., et al., "Simultaneous Detection of *Staphylococcus aureus* and Coagulase-Negative *Staphylococci* in Positive Blood Cultures by Real-Time PCR with Two Fluorescence Resonance Energy Transfer Probe Sets," Journal of Clinical Microbiology, 2004, vol. 42 (12), pp. 5739-5744.
Sala M., et al., "Ambiguous Base Pairing of the Purine Analogue 1-(2-Deoxy-B-D-Ribofuranosyl)-Imidazole-4- Carboxamide During PCR," Nucleic Acids Research, 1996, vol. 24 (17), pp. 3302-3306.
Sambrook J., et al., "Molecular Cloning-A Laboratory Manual," 1989, Cold Spring Harbor Laboratory Press, Table of Contents.
Sampath R., et al., "Global Surveillance of Emerging Influenza Virus Genotypes by Mass Spectrometry," Plos ONE, 2007, vol. 2 (5), pp. e489.
Sampath R., et al., "Rapid Identification of Emerging Infectious Agents using PCR and Electrospray Ionization Mass Spectrometry," Annals of the New York Academy of Science, 2007, vol. 1102, pp. 109-120.
Sampath R., et al., "Rapid Identification of Emerging Pathogens: Coronavirus," Emerging Infectious Diseases, 2005, vol. 11 (3), pp. 373-379.
Sanchez A., et al., "Detection and molecularcharacterization of Ebola viruses causing disease in human and nonhuman primates," Journal of Infectious Diseases, 1999, vol. 179 (1), pp. S164-S169.
Sanchez J.L., et al., "Epidemic of Adenovirus-Induced Respiratory Illness Among US Military Recruits: Epidemiologic and Immunologic Risk Factors in Healthy, Young adults," Journal of Medical Virology, 2001, vol. 65 (4), pp. 710-718.
Sanchez-Seco M.P., et al., "A Generic Nested-RT-PCR followed by Sequencing for Detection and Identification of Members of the Alphavirus Genus," Journal of Virological Methods, 2001, vol. 95 (1-2), pp. 153-161.
Santos S.R., et al., "Identification and phylogenetic sorting of bacterial lineages with universally conserved genes and proteins," Environmental Microbiology, 2004, vol. 6 (7), pp. 754-759.
Sarantis H., et al., "Comprehensive Detection and Serotyping of Human Adenoviruses by PCR and Sequencing," Journal of Clinical Microbiology, 2004, vol. 42 (9), pp. 3963-3969.
Sauer S., et al., "A Novel Procedure for Efficient Genotyping of Single Nucleotide Polymorphisms," Nucleic Acids Research, 2000, vol. 28 (5), pp. E13.1-E13.8.
Scaramozzino N., et al., "Comparison of Flavivirus universal Primer Pairs and Development of a Rapid, Highly Sensitive Hem inested Reverse Transcription-PCR Assay for Detection of Flaviviruses Targeted to a Conserved Region of the NS5 Gene Sequences," Journal of Clinical Microbiology, 2001, vol. 39 (5), pp. 1922-1927.
Schabereiter-Gurtner C., et al., "Application of Broad-Range 16s rRNA PCR Amplification and DGGE Fingerprinting for Detection of Tick-Infecting Bacteria," The Journal of Microbiological Methods, 2003, vol. 52 (2), pp. 251-260.

Scheffner M., et al., "The E6 Oncoprotein Encoded by Human Papillomavirus Types 16 and 18 Promotes the Degradation of p53," Cell, 1990, vol. 63 (6), pp. 1129-1136.

Schena M., et al., "Genome Analysis with Gene Expression Microarrays," Bioessays, 1996, vol. 18 (5), pp. 427-431.

Scheuermann R.N., et al., "Polymerase chain-reaction-based mRNA quantification Using an internal standard: analysis of oncogene expression," Methods in Enzymology, 1993, vol. 218, pp. 446-473.

Schlecht N. F., et al., "Viral Load as a Predictor of the Risk of Cervical Intraepithelial Neoplasia," British Journal of Cancer, 2003, vol. 103 (4), pp. 519-524.

Schmidt T.M., et al., "Analysis of a marine pikoplankton community by 16s rRNA gene cloning and sequencing," Journal of Bacteriology, 1991, vol. 173 (14), pp. 4371-4378.

Schmitz F.J., et al., "Development of a Multiplex-PCR for Direct Detection of the Genes for Enterotoxin B and C, and Toxic Shock Syndrome Toxin-1 in Staphylococcus aureus Isolates," Journal of Medical Microbiology, 1998, vol. 47 (4), pp. 335-340.

Schmitz F.J., et al., "Development of Resistance to Ciprofloxacin, Rifampin, and Mupirocin inMethicillin-Susceptible and -Resistant Staphylococcus aureus Isolates," Antimicrobial Agents and Chemotherapy, 2000, vol. 44 (11), pp. 3229-3231.

Schmitz F.J., et al., "Specific information concerning taxonomy, pathogenicity and methicillin esistance of staphylococci obtained by a multiplex PCR," Journal of Medical Microbiology, 1997, vol. 46 (9), pp. 773-778.

Schram K.H., et al., "Mass Spectrometry of Nucleic Acid Components," Methods of Biochemical Analysis, 1990, vol. 34, pp. 203-280.

Schultz J.C., et al., "Polymerise Chain Reaction Products Analyzed by Charge Detection Mass Spectrometry," Rapid Communications in Mass Spectrometry, 1999, vol. 13 (1), pp. 15-20.

Schwartz M., et al., "Prenatal Diagnosis of Alpha-1-Antitrypsin Deficiency Using Polymerase Chainreaction (PCR). Comparison of Conventional Rflp Methods with PCR used in Combination with Allelespecific Oligonucleotides or RFLP analysis, 787 Reexamination," Clinical Genetics, 1989, vol. 36 (6), pp. 419-426.

Schweiger B., et al., "Application of a Fluorogenic PCR Assay for Typing and Subtyping of Influenza Viruses in Respiratory Samples," Journal of Clinical Microbiology, 2000, vol. 38 (4), pp. 1552-1558.

Sciacchitano C.J., "Analysis of Polymerase Chain Reaction-Amplified DNA Fragments of Clostridium Botulinum Type E Neurotoxin Gene by High Performance Capillary Electrophoresis," Journal of Liquid Chromatography & Related Technologies, 1996, vol. 19 (13), pp. 2165-2178.
Scott-Taylor T.H., et al., "Conserved Sequences of the Adenovirus Genome for Detection of all Human Adenovirus Types by Hybridization," Journal of Clinical Microbiology, 1992, vol. 30 (7), pp. 1703-1710.
Seifarth W., et al., "Rapid identification of all known retroviral reverse transcriptase sequences with a novel versatile detection assay," AIDS Research and Human Retroviruses, 2000, vol. 16 (8), pp. 721-729.
Sellner L., et al., "A Single-Tube Nested RT-PCR for the Detection of Ross River Virus," Methods in Molecular Biology, 1998, vol. 92, pp. 145-152.
Sellner L.N., et al., "Sensitive detection of Ross River virus—a one-tube nested RT-PCR," Journal ofVirological Methods, 1994, vol. 49 (1), pp. 47-58.
Senko M.W., et al., "Determination of Monoisotopic Masses and Ion Populations for Large Biomoleculesfrom Resolved Isotopic Distributions," Journal of the American Society for Mass Spectrometry, 1995, vol. 6, pp. 229-233.
Seshadri R., et al., "Differential Expression of Translational Elements by Life Cycle Variants of *Coxiella burnetii*," Infection and Immunity, 1999, vol. 67 (11), pp. 6026- 6033.
Shadan F.F., et al., "n-Butyrate, a Cell Cycle Blocker, Inhibits the Replication of Polyomaviruses and Papillomaviruses but Not That of Adenoviruses and Herpesviruses," Journal of Virology, 1994, vol. 68 (8), pp. 4785-4796.
Shaver Y.J., et al., "Restriction Fragment Length Polymorphism of rRNA Operons for Discrimination and Intergenic Spacer Sequences for Cataloging of Bacilus Subtilis Sub-Groups," Journal of Microbiological Methods, 2002, vol. 50 (2), pp. 215-223.
Shaver Y.J., et al., "Variation in 16s-23s rRNA Intergenic Spacer Regions Among Bacilus Subtilis 168 Isolates," Molecular Microbiology, 2001, vol. 42 (1), pp. 101-109.
Shimaoka M., et al., "Detection of the gene for toxic shock syndrome toxin 1 in *Siaphylococcusaureus* by enzyme-labelled oligonucleotideprobes," Journal of Medical Microbiology, 1996, vol. 44 (3), pp. 215-218.
Shimaoka M., et al., "Development of Enzyme-Labeled Oligonucleotide Probe for Detection of mecA gene in Methicillin-Resistant *Staphylococcus aureus*," Journal of Clinical Microbiology, 1994, vol. 32 (8), pp. 1866-1869.
Shrestha N. K., et al., "Rapid Identification of *Staphylococcus aureus* and the mecA Gene from BacT/ALERT Blood Culture Bottles by Using the Lightcycler System," Journal of Clinical Microbiology, 2002, vol. 40 (7), pp. 2659-2661.
Simonsen L., et al., "The Impact of Influenza Epidemics on Hospitalizations," Journal of Infectious Diseases, 2000, vol. 181 (3), pp. 831-837.
Skov R.L., et al., "Evaluation of a new 3-h hybridization method for detecting the mecA gene in *Staphylococcus aureus* and comparison with existing genotypic and phenotypic susceptibility testing methods," Journal of Antimicrobial Chemotherapy, 1999, vol. 43 (4), pp. 467-475.
Smirnov I.P., et al., "Application of DNA-binding polymers for preparation of DNA for analysis by matrix-assisted laser desorption/ionization mass spectrometry," Rapid Communications in Mass Spectrometry, 2001, vol. 15 (16), pp. 1427-1432.
Smith T.F., "Comparison of Biosequences," Advances in Applied Mathematics, 1981, vol. 2, pp. 482-489.
Song F., et al., "Identification of cry11-type Genes from Bacilus Thuringiensis Strains and Characterization of a Novel Cry11-Type Gene," Applied and Environmental Microbiology, 2003, vol. 69, pp. 5207-5211.
Spackman E., et al., "Development of a real-time reverse transcriptase PCR assay for type A influenzavirus and the avian H5 and H7 hemagglutinin subtypes," Journal of Clinical Microbiology, 2002, vol. 40 (9), pp. 3256-3260.
Spiess L., et al., "Trehalose is a potent PCR enhancer: Lowering of DNA melting temperature and thermal stabilization of Taq polymerase by the disaccharide trehalose," Clinical Chemistry, 2004, vol. 50 (7), pp. 1256-1259.
Srinivasan J.R., et al., "Matrix-Assisted Laser Desorption/lonization Time-of-Flight Mass Spectrometry as a Rapid Screening Method to Detect Mutations Causing Tay-Sachs Disease," Rapid Communications in Mass Spectrometry, 1997, vol. 11 (10), pp. 1144-1150.
Steffens D.L., et al., "Sequence Analysis of Mitochondrial DNA Hypervariable Regions Using Infrared Fluorescence Detection," BioTechniques, 1998, vol. 24 (6), pp. 1044-1046.
Stephensen C.B., et al., "Phylogenetic analysis of a highly conserved region of the poymerase gene from 11 coronaviruses and development of a consensus poymerase chain reaction assay," Virus Research, 1999, vol. 60 (2), pp. 181-189.
Stone B., et al., "Rapid detection and simultaneous subtype differentiation of influenza a viruses by real time Pcr," Journal of Virological Methods, 2004, vol. 117 (2), pp. 103-112.
Stoneking M., et al., "Population Variation of Human mtDNA Control Region Sequences Detected by Enzymatic Amplification and Sequence-Specific Oligonucleotide Probes," American Journal of Human Genetics, 1991, vol. 48 (2), pp. 370-382.
Strommenger B., et al., "Multiplex PCR Assay for Simultaneous Detection of Nine Clinically Relevant Antibiotic Resistance Genes in *Staphylococcus aureus*," Journal of Clinical Microbiology, 2003, vol. 41 (9), pp. 4089-4094.
Studdert M.J., et al., "Polymerase Chain Reaction Tests for the Identification of Ross River, Kunjinand Murray Valley Encephalitis Virus Infections in Horses," Austrailian Verterinary Journal, 2003, vol. 81 (1-2), pp. 76-80.
Stuhlmeier R., et al., "Fast, Simultaneous, and Sensitive Detection of Staphylococci," Journal of Clinical Pathology, 2003, vol. 56 (10), pp. 782-785.

Sumner J.W., et al., "PCR Amplification and Comparison of Nucleotide Sequences from the groESL Heat Shock Operon of Ehrlichia Species," Journal of Critical Microbiology, 1997, vol. 35 (8), pp. 2087-2092.

Sundsfjord A., et al., "Genetic Methods for Detection of Antimicrobial Resistance," APMIS : Acta Pathologica, Microbiologica, et Immunologica Scandinavica, 2004, vol. 112 (11-12), pp. 815-837.

Supplementary European Search Report for Application No. 04775904.8, mailed on Jul. 7, 2008, 8 pages.

Supplementary European Search Report for Application No. EP02709785.6, mailed Sep. 1, 2005, 5 pages.

Supplementary European Search Report for Application No. EP03796752.8, mailed on Aug. 7, 2007, 3 pages.

Supplementary European Search Report for Application No. EP03810055.8, mailed on Jun. 8, 2007, 4 pages.

Supplementary European Search Report for Application No. EP03814656, mailed on Oct. 16, 2007, 2 pages.

Supplementary European Search Report for Application No. EP04752257.8, mailed on Feb. 15, 2006, 2 pages.

Supplementary European Search Report for Application No. EP05753037, mailed on Aug. 21, 2009, 2 pages.

Supplementary Partial European Search Report for Application No. EP05751872.2, mailed on Jan. 28, 2008, 8 pages.

Supplementary Partial European Search Report for Application No. EP05856582.1, mailed on Oct. 27, 2008, 10 pages.

Swaminathan B., et al., "PulseNet: The Molecular Subtyping Network for Foodborne Bacterial Disease Surveillance, United States," Emerging Infectious Diseases, 2001, vol. 7 (3), pp. 382-389.

Swanborg R.H., et al., "Human Herpesvirus 6 and Chlamydia Pneumoniae as Etiologic Agents in Multiplesclerosis—a Critical Review," Microbes and Infection / Institut Pasteur, 2002, vol. 4 (13), pp. 1327-1333.

Swenson J.M., et al., "Performance of Eight Methods, Including Two New Rapid Methods, for Detection of Oxacillin Resistance in a Challenge Set of Staphylococcus aureus Organisms," Journal of Clinical Microbiology, 2001, vol. 39 (10), pp. 3785-3788.

Takagaki Y., et al., "Four Factors are Required for 3'-End Cleavage of Pre-mRNAs," Genes and Development, 1989, vol. 3 (11), pp. 1711-1724.

Takahashi H., et al., "Characterization of gryA, gryB, grIA and grIB mutations in fluoroquinolon—resistant clinical isolates of Staphylococcus aureus," The Journal of Antimicrobial Chemotherapy, 1998, vol. 41 (1), pp. 49-57.

Takahata M., et al., "Mutations in the GyrA and Gr1A Genes of Quinolone-Resistant Clinical Isolates of Methicillin-Resistant Staphylococcus Aureus," The Journal of Antimicrobial Chemotherapy, 1996, vol. 38 (3), pp. 543-546.

Takayama R., et al., "Quantification of Adenovirus Species B and C Viremia by Real-Time PCRr in Adults and Children Undergoing Stem Cell Transplantation," Journal of Medical Virology, 2007, vol. 79 (3), pp. 278-284.

Takeuchi S., et al., "Serotyping of Adenoviruses on Conjunctival Scrapings by PCR and Sequence Analysis," Journal of Clinical Microbiology, 1999, vol. 37 (6), pp. 1839-1845.

Talaat A.M., et al., "Genome-Directed Primers for Selective Labeling of Bacterial Transcripts for DNA Microarray Analysis," Nature Biotechnology, 2000, vol. 17, pp. 679-682.

Tan T.Y., "Use of Molecular Techniques for the Detection of Antibiotic Resistance in Bacteria," Expert review of Molecular diagnostics, 2003, vol. 3 (1), pp. 93-103.

Tanabe F., et al., "The Properties and Mec A Gene of the Methicillin-Resistant Staphylococcus aureus Isolated in Fukushima Medical College Hospital," Fukushima Journal of Medical Science, 1993, vol. 39 (1), pp. 35-42.

Tang K., et al., "Detection of 500-Nucleotide DNA by Laser Desorption Mass Spectrometry," Rapid Communications in Mass Spectrometry, 1994, vol. 8 (9), pp. 727-730.

Tang K., et al., Double-Stranded DNA Analysis by Matrix Assisted Laser Desorption/Ionization, 42nd ASMS Conference on Mass Spectrometry, 1994.

Tang K., et al., "Matrix-Assisted Laser Desorption/Ionization of Restriction Enzyme-Digested DNA," Rapid Communications in Mass Spectrometry, 1994, vol. 8 (2), pp. 183-186.

Tang K., et al., "Matrix-Assisted Laser Desorption/Ionization Mass Spectrometry of Oligonucleotides," Dissertation submitted to the Faculty of Vanderbilt University, 1994.

Tarassishin L., et al., "Adenovirus Core Protein VII Displays a Linear Epitope Conserved in a Range of Human Adenoviruses," Journal of General Virology, 1999, vol. 80 (Pt 1), pp. 47-50.

Tarassishin L., et al., "An Epitope on the Adenovirus Fibre Tail is Common to all Human Subgroups," Archives of Virology, 2000, vol. 145 (4), pp. 805-811.

Tatuch Y., et al., "Heteroplasmic mtDNA Mutation (T-G) at 8993 Can Cause Leigh Disease When the Percentage of Abnormal mtDNA is High," The American Journal of Human Genetics, 1992, vol. 50 (4), pp. 852-858.

Taubenberger J.K., et al., "Characterization of the 1918 Influenza Virus Polymerase Genes," Nature, 2005, vol. 437 (7060), pp. 889-893.

Taylor L.H., et al., "Risk Factors for Human Disease Emergence," Philosophical Transactions of the Royal Society of London Series B, Biological Sciences, 2001, vol. 356 (1411), pp. 983-989.

Tenover F.C., et al., "Characterization of a Strain of Community-Associated Methicillin-Resistant Slaphylococcus aureus Widely Disseminated in the United States," Journal of Clinical Microbiology, 2006, vol. 44 (1), pp. 108-118.

Teramura T., et al., "Quantitative Detection of Serum Adenovirus in a Transplant Recipient," Lancet, 2002, vol. 359 (9321), pp. 1945.

Thiel V., et al., "Infectious RNA Transcribed in Vitro from a cDNA The Human Coronavirus Genome Cloned in Vaccinia Virus," The Journal of General Virology, 2001, vol. 82 (Pt 6), pp. 1273-1281.

Thompson J.D., et al., "Clustal W: Improving the Sensitivity of Progressive Multiple Sequence Alignmen Through Sequence Weighting, Position-Specific Gap Penalties and Weight Matrix Choice," Nucleic Acids Research, 1994, vol. 22 (22), pp. 4673-4680.

Thompson W.W., et al., "Influenza-Associated Hospitalizations in the United States," The Journal of the American Medical Association, 2004, vol. 292 (11), pp. 1333-1340.

Tokue Y., et al., "Comparison of a Polymerase Chain Reaction Assay and a Conventional Microbiologic Method for Detection of Methicillin-Resistant Slaphylococcus aureus," Antimicrobial Agents and Chemotherapy, 1992, vol. 36 (1), pp. 6-9.

Tong J., et al., "Ligation Reaction Specificities of an NAD+-Dependent DNA Ligase from the Hyperthermophile Aquifex Aeolicus," Nucleic Acids Research, 2000, vol. 28 (6), pp. 1447-1454.

Top FH Jr., "Control of Adenovirus Acute Respiratory Disease in U.S. Army Trainees," The Yale Journal of Biology and Medicine, 1975, vol. 48 (3), pp. 185-195.

Torroni A., et al., "Classification of European mtDNAs from an Analysis of Three European Populations," Genetics, 1996, vol. 144 (4), pp. 1835-1850.

Towner K.J., et al., "Development and Evaluation of a PCR-Based Immunoassay for the Rapid Detection of Methicillin-Resistant Staphylococcus aureus," Journal of Medical Microbiology, 1998, vol. 47 (7), pp. 607-613.

Tsuneyosh I, et al., "Mass Spectrometric Gene Diagnosis of One-Base Substitution from Polymerase Chain Reaction Amplified Human DNA," Rapid Communications in Mass Spectometry, 1997, vol. 11 (7), pp. 719-722.

Tsunoda T., et al., "Time and Memory Efficient Algorithm for Extracting Palindromic and RepetitiveSubsequences in Nucleic Acid Sequences," Pacific Symposium on Biocomputing, 1999, vol. 4, pp. 202-213.

Udo E.E., et al., "A Chromosomal Location of the MupA Gene in Staphylococcus aureus Expressing High-Level Mupirocin Resistance," The Journal of Antimicrobial Chemotherapy, 2003, vol. 51 (5), pp. 1283-1286.

Udo E.E., et al., "Genetic Analysis of Methicillin-Resistant Staphylococcus aureus Expressing High-and Low-Level Mupirocin Resistance," Journal of Medical Microbiology, 2001, vol. 50 (10), pp. 909-915.

Udo E.E., et al., "Rapid Detection of Methicillin Resistance in Staphylococci Using a Slide Latex Agglutination Kit," International Journal of Antimicrobial Agents, 2000, vol. 15 (1), pp. 19-24.

Unal S., et al., "Detection of Methicillin-Resistant *Staphylococci* by Using the Polymerase Chain Reaction," Journal of Clinical Microbiology, 1992, vol. 30 (7), pp. 1685-1691.
Upton A., et al., "Mupirocin and *Staphylococcus aureus*: A Recent Paradigm of Emerging Antibiotic Resistance," The Journal of Antimicrobial Chemotherapy, 2003, vol. 51 (3), pp. 613-617.
U.S. Appl. No. 60/369,405.
U.S. Appl. No. 60/397,365.
U.S. Appl. No. 60/431,319.
U.S. Appl. No. 60/443,443.
U.S. Appl. No. 60/443,788.
U.S. Appl. No. 60/447,529.
U.S. Appl. No. 60/453,607.
U.S. Appl. No. 60/461,494.
U.S. Appl. No. 60/470,175.
U.S. Appl. No. 60/501,926.
U.S. Appl. No. 60/509,911.
U.S. Appl. No. 60/604,329.
U.S. Appl. No. 60/615,387.
U.S. Appl. No. 60/701,404.
U.S. Appl. No. 60/705,631.
U.S. Appl. No. 60/720,843.
U.S. Appl. No. 60/747,607.
U.S. Appl. No. 60/771,101.
U.S. Appl. No. 60/773,124.
U.S. Appl. No. 60/891,479.
U.S. Appl. No. 60/941,641.
Vabret A., et al., "Development of a PCR-and Hybridization-Based Assay (PCR Adenovirus Consensus) for the Detection and the Species Identification of Adenoviruses in Respiratory Specimens," Journal of Clinical Virology, 2004, vol. 31 (2), pp. 116-122.
Van Aerschot A., et al., "In Search of Acyclic Analogues as Universal Nucleosides in Degenerate Probes," Nucleosides and Nucleotides, 1995, vol. 14 (3-5), pp. 1053-1056.
Van Baar B.L., "Characterisation of Bacteria by Matrix-Assisted Laser Desorption/Ionisation and Electrospray Mass Spectrometry," FEMS Microbiology Reviews, 2000, vol. 24 (2), pp. 193-219.
Van Camp G., et al., "Amplification and Sequencing of Variable Regions in Bacterial 23s Ribosomal RNA Genes with Conserved Primer Sequences," Current Microbiology, 1993, vol. 27 (3), pp. 147-151.
Van Der Vossen J.M., et al., "DNA Based Typing Identification and Detection Systems for Food Spoilage Microorganisms: Development and Implementation," International Journal of Food Microbiology, 1996, vol. 33 (1), pp. 35-49.
Van Der Zee H., et al., "Rapid and Alternative Screening Methods for Microbiological Analysis," Journal of Aoac International, 1997, vol. 80 (4), pp. 934-940.
Van Dinten L.C., et al., "Proteolytic Processing of the Open Reading Frame Ib-EncodedPart of Arterivirus Replicase Is Mediated by nsp4 Serine Protease and is Essential for Virus Replication," Journal of Virology, 1999, vol. 73 (3), pp. 2027-2037.
Van Elden L.J., et al., "Clinical Diagnosis of Influenza Virus Infection: Evaluation of Diagnostic Tools in General Practice," the British Journal of General Practice, 2001, vol. 51 (469), pp. 630-634.
Van Elden L.J., et al., "Simultaneous Detection of Influenza Viruses A and B Using Real-Time Quantitative PCR," Journal of Clinical Microbiology, 2001, vol. 39 (1), pp. 196-200.
Van Ert M.N., et al., "Mass Spectrometry Provides Accurate Characterization of Two Genetic Marker Types in Bacillus Anthracis," Bio Techniques, 2004, vol. 37 (4), pp. 642-651.
Van Leeuwen W.B., et al., "Multilocus Sequence Typing of *Staphylococcus aureus* with DNA Array Technology," Journal of Clinical Microbiology, 2003, vol. 41 (7), pp. 3323-3326.
Van Leeuwen W.B., et al., "Rapid Detection of Methicillin-Resistance in *Staphylococcus aureus* Isolates by the MRSA-Screen Latex Agglutination Test," Journal of Clinical Microbiology, 1999, vol. 37 (9), pp. 3029-3030.
Vanchiere J.A., et al., "Detection of BK Virus and Simian Virus 40 in the Urine of Healthy Children," Journal of Medical Virology, 2005, vol. 75 (3), pp. 447-454.
Vanderhallen H., et al. "Identification of Encephalomyocarditis Virus in Clinical Samples by ReverseTranscription-PCR Followed by Genetic Typing Using Sequence Analysis," Journal of Clinical Microbiology, 1998, vol. 36 (12), pp. 3463-3467.
Vannuffel P., et al., "Rapid and Specific Molecular Identification of Methicillin-Resistant *Staphylococcus aureus* in Endotracheal Aspirates from Mechanically Ventilated Patients," Journal of Clinical Microbiology, 1998, vol. 36 (8), pp. 2366-2368.
Vannuffel P., et al., "Specific Detection of Methicillin-Resistant *Staphylococcus* Species by Multiplex Pcr," Journal of Clinical Microbiology, 1995, vol. 33 (11), pp. 2864-2867.
Verma S., et al., "Modified Oligonucleotides: Synthesis and Strategy for Users," Annual Review of Biochemistry, 1998, pp. 99-134.
Videla C., et al., "Genomic Analysis of Adenovirus Isolated from Argentinian Children with Acute Lower Respiratory Infections," Journal of Clinical Virology, 1999, vol. 14 (1), pp. 67-71.
Vilchez R.A. et al., "Detection of Polyomavirus Simian Virus 40 Tumor Antigen DNA in Aids-Related Systemic Non-Hodgkin Lymphoma," Journal of Acquired Immune Deficiencysyndromes, 2002, vol. 29 (2), pp. 109-116.
Voelter C., et al., "Screening Human Tumor Samples with a Broad-Spectrum Polymerase Chain Reaction Method for the Detection of Polyomaviruses," Virology, 1997, vol. 237 (2), pp. 389-396.
Volokhov D., et al., "Microarray Analysis of Erythromycin Resistance Determinants," Journal of Applied Microbiology, 2003, vol. 95 (4), pp. 787-798.
Von Eiff C., et al., "Pathogenesis of Infections Due to Coagulase-Negative Staphylococci," The Lancet Infectious Diseases, 2002, vol. 2 (11), pp. 677-685.
Walker E.S., et al., "A Decline in Mupirocin Resistance in Methicillin-Resistant *Staphylococcus aureus* Accompanied Administrative Control of Prescriptions," Journal of Clinical Microbiology, 2004, vol. 42 (6), pp. 2792-2795.
Wallace S.S., et al., "The Enigma of Endonuclease VII," DNA Repair, 2003, vol. 2 (5), pp. 441-453.
Wallet F., et al., "Choice of a Routine Method for Detecting Methicillin-Resistance in *Staphylococci*," The Journal of Antimicrobial Chemotherapy, 1996, vol. 37 (5), pp. 901-909.
Walters J.J., et al., "Genotyping Single Nucleotide Polymorphisms Using Intact Polymerase Chain Reaction Products by Electrospray Quadrupole Mass Spectrometry," Rapid Communications in Mass Spectrometry, 2001, vol. 15 (18), pp. 1752-1759.
Wang G., et al., "Targeted Mutagenesis in Mammalian Cells Mediated by Intracellular Triple Helix Formation," Molecular and Cellular Biology, 1995, vol. 15 (3), pp. 1759-1768.
Ward C.L., et al., "Design and Performance Testing of Quantitative Real Time PCR Assays for Influenza A and B Viral Load Measurement," Journal of Clinical Virology, 2004, vol. 29 (3), pp. 179-188.
Watanabe K., et al., "ICB Database: the gyrB Database for Identification and Classification of Bacteria," Nucleic Acids Research, 2001, vol. 29 (1), pp. 344-345.
Weissenbacher M., et al., "Etiologic and Clinical Evaluation of Acute Lower Respiratory TractInfections in Young Argentinean Children: An Overview," Reviews of Infectious Diseases, 1990, vol. 12 (Suppl 8), pp. S889-S898.
Welham K.J., et al., "The Characterization of Micro-Organisms by Matrix-Assisted Laser Desorption/Lonization Time-of-Flight Mass Spectrometry," Rapid Communications in Mass Spectrometry, 1998, vol. 12 (4), pp. 176-180.
Wertheim H.F., et al., "Effect of Mupirocin Treatment on Nasal, Pharyngeal, and Perineal Carriage of *Staphylococcus aureus* in Healthy Adults," Antimicrobial Agents and Chemotherapy, 2005, vol. 49 (4), pp. 1465-1467.
Westermann P., et al., "Inhibition of Expression of SV40 Virus Large T-Antigen by Antisense Oligodeoxyribonucleotides," Biomedica Biochimica Acta, 1989, vol. 1, pp. 85-93.
Whiley D.M., et al., "Simultaneous Detection and Differentiation of Human Polyomaviruses JC and BK by a Rapid and Sensitive PCR-ELAHA Assay and a Survey of the JCV Subtypes within an Australian Population," Journal of Medical Virology, 2004, vol. 72 (3), pp. 467-472.
Wichelhaus T.A., et al., "Rapid Detection of Epidemic Strains of Methicillin-Resistant*Staphylococcus aureus*," Journal of Clinical Microbiology, 1999, vol. 37 (3), pp. 690-693.

Wickham T.J., "Targeting Adenovirus," Gene Therapy, 2000, vol. 7 (2), pp. 110-114.

Widjojoatmodjo M.N., et al., "Rapid Identification of Bacterial by PCR-SingleStrand Conformation Polymorphism," Journal of Clinical Microbiology, 1994, vol. 32 (12), pp. 3002-3007.

Widjojoatmodjo M.N., et al., "The Magnetic Immuno Polymerase Chain Reaction Assay for Direct Detection of *Salmonellae* in Fecal Samples," Journal of Clinical Microbiology, 1992, vol. 30 (12), pp. 3195-3199.

Winger B.E., et al., "High Resolution Accurate Mass Measurements of Biomolecules using a new Electrospray Ionization Ion Cyclotron Resonance Mass Spectrometer," Journal American Society for Mass Spectrometry, 1993, vol. 4 (7), pp. 566-577.

Wolter A., et al., "Negative ion FAB mass Spectrometric Analysis of non-Charged key Intermediates in Oligonucleotide Synthesis: Rapid Identification of Partially Protected Dinucleoside Monophosphates," Biomedical and Environmental Mass Spectrometry, 1987, vol. 14, pp. 111-116.

Woo T.H., et al., "Identification of Leptospira Inadai by Continuous Monitoring of Fluorescence during Rapid Cycle PCR," Systematic and Applied Microbiology, 1998, vol. 21 (1), pp. 89-96.

Wood S.R., et al., "Rapid Detection and Serotyping of Adenovirus by Direct Immunofluorescence," Journal of Medical Virology, 1997, vol. 51 (3), pp. 198-201.

Wright K.E., et al., "Typing and Subtyping of Influenza Viruses in Clinical Samples by PCR," Journal of Clinical Microbiology, 1995, vol. 33 (5), pp. 1180-1184.

Written Opinion for Application No. PCT/US2004/33742, mailed on May 15, 2006, 5 pages.

Wu S., et al., "Genetic Organization of the mecA Region in Methicillin-Susceptible and Methicillin-Resistant Strains of *Staphylococcus sciuri*," The Journal of Bacteriology, 1998, vol. 180 (2), pp. 236-242.

Wu X., et al., "Establishment of a Fluorescent Polymerase Chain Reaction Method for the Detection of SARS-Associated Coronavhus and its Clinical Application," Chinese Medical Journal, 2003, vol. 116 (70, pp. 988-990.

Wunschel D., et al., "Discrimination Among the *B. cereus* Group, in Comparison to *B. subtilis*, by Structural Carbohydrate Profiles and Ribosomal RNA Spacer Region PCR," Systematic and Applied Microbiology, 1994, vol. 17, pp. 625-635.

Wunschel D.S., et al., "Analysis of Double-Stranded Polymerase Chain Reaction Products from the Bacilus Cereus Group by Electrospray Lonization Fourier Transform Lon Cyclotron Resonance Mass Spectrometry," Rapid Communications in Mass Spectrometry, 1996, vol. 10 (1), pp. 29-35.

Wunschel, D.S., et al., "Heterogeneity in *Bacillus cereus* PCR Products Detected by ESI-FTICR Mass Spectrometry," Analytical Chemistry, 1998, vol. 70 (6), pp. 1203-1207.

Wunschel D.S., et al., "Mass spectrometric characterization of DNA for molecular biological applications: advances using MALDI and ESI," Advances in Mass Spectrometry, 1998, vol. 14, Elsevier, pp. 377-406.

Xu L., et al., "Electrophore Mass Tag Dideoxy DNA Sequencing," Analytical Chemistry, 1997, vol. 69 (17), pp. 3595-3602.

Xu W., et al., "Species-Specific Identification of Human Adenoviruses by a Multiplex PCR Assay," Journal of Clinical Microbiology, 2000, vol. 38 (11), pp. 4114-4120.

Xu W., et al., "Type-Specific Identification of Human Adenovirus, 3, 7, and 21 by a Multiplex PCR Assay," Journal of Medical Virology, 2001, vol. 64 (4), pp. 537-542.

Xu X., et al., "Intercontinental Circulation of Human Influenza A(H1N2) Reassortant Viruses During the 2001-2002 Influenza Season," The Journal of Infectious Diseases, 2002, vol. 186 (10), pp. 1490-1493.

Yao Z.P., et al., "Mass Spectrometry Based Proteolytic Mapping for Rapid Virus Identification," Analytical Chemistry, 2002, vol. 74 (11), pp. 2529-2534.

Yasui T., et al., "A Specific Oligonucleotide Primer for the Rapid Detection of *Lactobacillus lindneri* by Polymerase Chain Reaction," Canadian Journal of Microbiology, 1997, vol. 43 (2), pp. 157-163.

Ye K., et al., "Three Distinct Promoters Direct Transcription of Different 5' Untranslated Regions of the Human Interleukin 1 Type 1 Receptor. A Possible Mechanism for Control of Translation," Cytokine, 1996, vol. 8 (6), pp. 421-429.

Yun H.J., et al., "Increased Antibacterial Activity of OW286, A Novel Fluoronaphthyridone Antibiotic, Against *Staphylococcus aureus* Strains with Defined Mutations in DNA Gyrase and Toposiomerase IV," International Journal of Antimicrobial Agents, 2005, vol. 25 (4), pp. 334-337.

Zeng Z.B., "Precision Mapping of Quantitative Trait Loci," Genetics, 1994, vol. 136 (4), 1 pp. 1457-1468.

Zhang J., et al., "PowerBLAST: A New Network BLAST Application for Interactive or Automated Sequence Analysis and Annotation," Genome Research, 1997, vol. 7 (6), pp. 649-656.

Zhang K., et al., "New Quadriplex PCR Assay for Detection of Methicillin and Mupirocin Resistance and Simultaneous Discrimination of *Staphylococcus aureus* from Coagulase-Negative *Staphylococci*," Journal of Clinical Microbiology, 2004, vol. 42 (11), pp. 4947-4955.

Zhang W.D., et al., "Detection and Identification of Human Influenza Viruses by the Polymerase Chain Reaction," Journal of Virological Methods, 1991, vol. 33 (1-2), pp. 165-189.

Zhang Y.Q., et al., "Genome-Based Analysis of Virulence Genes in a Non-Biofilm-Forming *Staphylococcus epidemidis* Strain (ATCC 12228)," Molecular Microbiology, 2003, vol. 49 (6), pp. 1577-1593.

\* cited by examiner

COMPOSITIONS FOR USE IN IDENTIFICATION OF ORTHOPOXVIRUSES

This application is a continuation-in-part of U.S. patent application Ser. No. 10/728,486, filed Dec. 5, 2003, now U.S. Pat. No. 7,718,354. This application also claims the benefit of priority to U.S. Provisional Application Ser. No. 60/604,329, filed Aug. 24, 2004, which is incorporated herein by reference in its entirety.

STATEMENT OF GOVERNMENT SUPPORT

This invention was made with United States Government support under DARPA contract MDA972-00-C-0053. The United States Government has certain rights in the invention.

FIELD OF THE INVENTION

The present invention relates generally to the field of genetic identification and quantification of orthopoxviruses and provides methods, compositions and kits useful for this purpose, as well as others, when combined with molecular mass analysis.

BACKGROUND OF THE INVENTION

A. Orthopoxviruses

The poxviruses comprise a large family of complex DNA viruses that infect both vertebrate and invertebrate hosts. General properties of the Poxvirus family include (a) a large complex virion containing enzymes for mRNA synthesis, (b) a genome composed of a single linear double-strand DNA molecule of 130 to 300 kilobases, and (c) the ability to replicate within the cytoplasmic compartment of the cell. The vertebrate poxviruses have been placed into six genera: *Orthopoxvirus*, *Parapoxvirus*, *Capripoxvirus*, *Leporipoxvirus*, *Suipoxvirus*, and *Avipoxvirus*.

Three members of the *Orthopoxvirus* genus are known to cause disease in humans. The most notorious member of the Poxvirus family is the variola virus which, before its eradication, was responsible for smallpox. Cowpox virus and Monkeypox virus also cause disease in humans. Additional members of the *Orthopoxvirus* genus include: Buffalopox virus, Camelpox virus, Rabbitpox virus, Raccoonpox virus, Volepox virus and Ectromeila virus.

B. Bioagent Detection

A problem in determining the cause of a natural infectious outbreak or a bioterrorist attack is the sheer variety of organisms that can cause human disease. There are over 1400 organisms infectious to humans; many of these have the potential to emerge suddenly in a natural epidemic or to be used in a malicious attack by bioterrorists (Taylor et al., Philos. Trans. R. Soc. London B. Biol. Sci., 2001, 356, 983-989). This number does not include numerous strain variants, bioengineered versions, or pathogens that infect plants or animals.

Much of the new technology being developed for detection of biological weapons incorporates a polymerase chain reaction (PCR) step based upon the use of highly specific primers and probes designed to selectively detect individual pathogenic organisms. Although this approach is appropriate for the most obvious bioterrorist organisms, like smallpox and anthrax, experience has shown that it is very difficult to predict which of hundreds of possible pathogenic organisms might be employed in a terrorist attack. Likewise, naturally emerging human disease that has caused devastating consequence in public health has come from unexpected families of bacteria, viruses, fungi, or protozoa. Plants and animals also have their natural burden of infectious disease agents and there are equally important biosafety and security concerns for agriculture.

An alternative to single-agent tests is to perform broad-range consensus priming of a gene target conserved across groups of bioagents. Broad-range priming has the potential to generate amplification products across entire genera, families, or, as with bacteria, an entire domain of life. This strategy has been successfully employed using consensus 16S ribosomal RNA primers for determining bacterial diversity, both in environmental samples (Schmidt et al., J. Bact., 1991, 173, 4371-4378) and in natural human flora (Kroes et al., Proc. Nat. Acad. Sci. (USA), 1999, 96, 14547-14552). One drawback of this approach for unknown bioagent detection and epidemiology is that analysis of the PCR products requires cloning and sequencing of hundreds to thousands of colonies per sample, which is impractical to perform rapidly or on a large number of samples.

Conservation of sequence is not as universal for viruses. Large groups of viral species, however, share conserved protein-coding regions, such as regions encoding viral polymerases or helicases. Like bacteria, consensus priming has also been described for detection of several viral families, including coronaviruses (Stephensen et al., Vir. Res., 1999, 60, 181-189), enteroviruses (Oberste et al., J. Virol., 2002, 76, 1244-51; Oberste et al., J. Clin. Virol., 2003, 26, 375-7; and Oberste et al., Virus Res., 2003, 91, 241-8), retroid viruses (Mack et al., Proc. Natl. Acad. Sci. U.S.A., 1988, 85, 6977-81; Seifarth et al., AIDS Res. Hum. Retroviruses, 2000, 16, 721-729; and Donehower et al., J. Vir. Methods, 1990, 28, 33-46), and adenoviruses (Echavarria et al., J. Clin. Micro., 1998, 36, 3323-3326). However, as with bacteria, there is no adequate analytical method other than sequencing to identify the viral bioagent present.

In contrast to PCR-based methods, mass spectrometry provides detailed information about the molecules being analyzed, including high mass accuracy. It is also a process that can be easily automated. DNA chips with specific probes can only determine the presence or absence of specifically anticipated organisms. Because there are hundreds of thousands of species of benign pathogens, some very similar in sequence to threat organisms, even arrays with 10,000 probes lack the breadth needed to identify a particular organism.

There is a need for a method for identification of bioagents which is both specific and rapid, and in which no culture or nucleic acid sequencing is required.

The present invention provides, inter alia, methods of identifying unknown viruses, including viruses of the *Orthopoxvirus* genus. Also provided are oligonucleotide primers, compositions, and kits containing the oligonucleotide primers, which define orthopoxvirus identifying amplicons and, upon amplification, produce corresponding amplification products whose molecular masses provide the means to identify orthopoxviruses at the species and sub-species or strain level.

SUMMARY OF THE INVENTION

The present invention provides, inter alia, primers and compositions comprising pairs of primers, and kits containing the same for use in identification of orthopoxviruses. The primers are designed to produce orthopoxvirus identifying amplicons of DNA encoding genes essential to orthopoxvirus replication. The invention further provides compositions comprising one or more pairs of primers and kits containing the same, which are designed to provide species and sub-species or strain level characterization of orthopoxviruses.

The individual orthopoxvirus primers of the invention are primers that are 13 to 35 nucleobases in length comprising at least 70% sequence identity with any of SEQ ID NOs: 1, 2, 3, 4, 5, 6, 24, 25, 26, 27, 28, and 29. The primer pairs of the invention comprise these same individual primers in the following combinations: SEQ ID NOs: 1:24, 2:25, 3:26,4:27, 5:28, and 6:29. The kits of the invention can comprise any combination of the same primer pairs.

The invention also provides methods of using the primer pairs and kits comprising the same for identification of orthopoxviruses and also for determining the presence or absence of an orthopoxvirus in a sample by using the primer pairs to obtain orthopoxvirus bioagent identifying amplicons, determining their molecular masses or base compositions and comparing the molecular masses or base compositions with molecular masses or base compositions of known orthopoxvirus bioagent identifying amplicons.

The invention also provides orthopoxvirus bioagent identifying amplicons obtained by amplification of a segment of a genome of an orthopoxvirus with any of the primer pairs listed above. The orthopoxvirus genomes from which orthopoxvirus bioagent identifying amplicons are obtained include, but are not limited to, the GenBank Accession numbers given in Table 3 (vide infra).

DETAILED DESCRIPTION OF EMBODIMENTS

Figure 1:
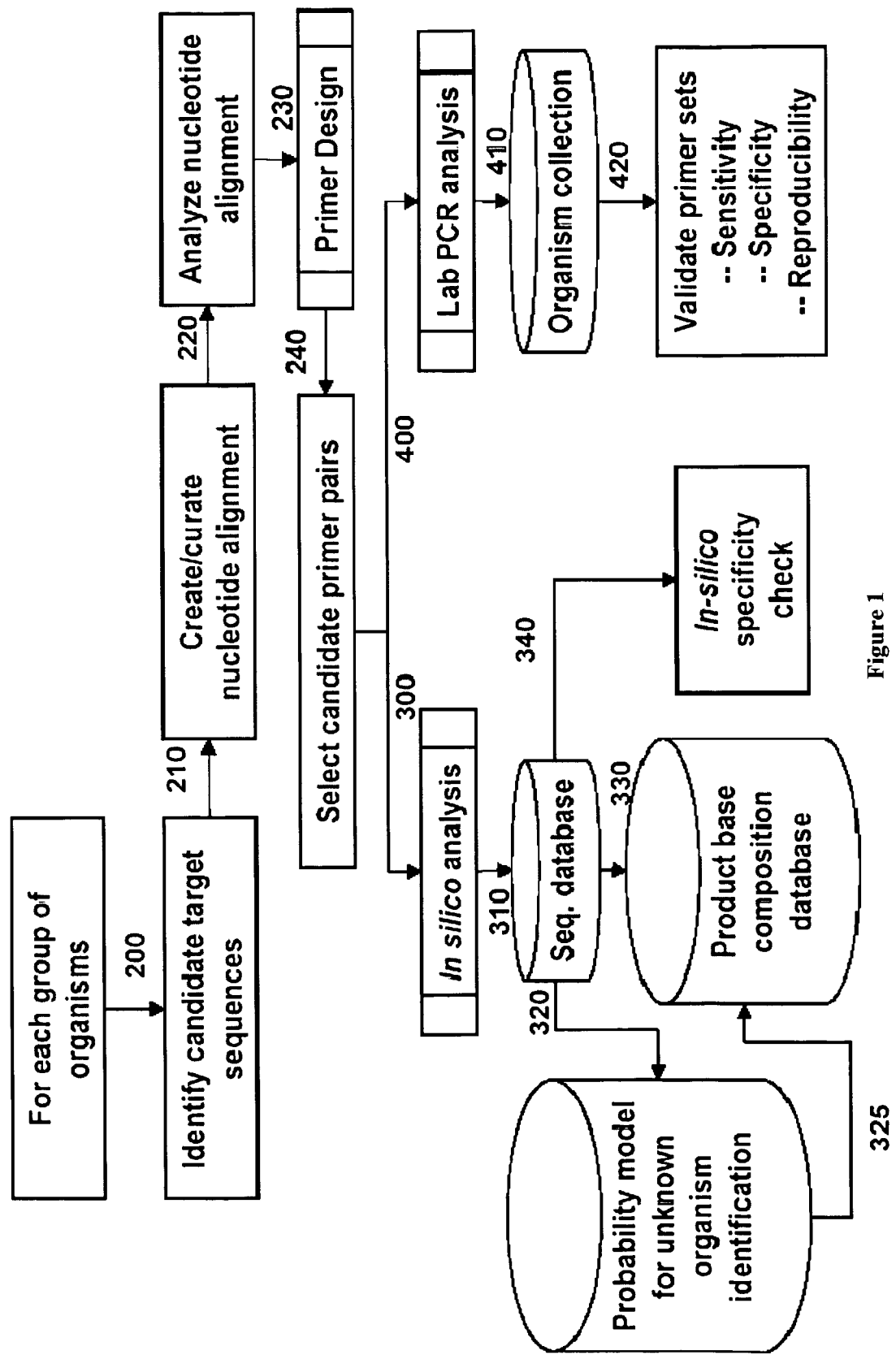
FIG. 1 is a representative process diagram illustrating a representative primer design process.

The present invention provides, inter alia, methods for detection and identification of orthopoxviruses in an unbiased manner using orthopoxvirus identifying amplicons. Intelligent primers are selected to hybridize to conserved sequence regions of nucleic acids derived from an orthopoxvirus and which bracket or flank variable sequence regions to yield an orthopoxvirus identifying amplicon. The orthopoxvirus identifying amplicon can be amplified and is amenable to molecular mass determination. The molecular mass then provides a means to uniquely identify the orthopoxvirus without a requirement for prior knowledge of the possible identity of the orthopoxvirus. The molecular mass or corresponding base composition signature (BCS) of the amplification product is then matched against a database of molecular masses or base composition signatures. Furthermore, the method can be applied to rapid parallel multiplex analyses, the results of which can be employed in a triangulation identification strategy. The present method provides rapid throughput and does not require nucleic acid sequencing of the amplified target sequence for orthopoxvirus detection and identification.

In the context of the present invention, a "bioagent" is any organism, cell, or virus, living or dead, or a nucleic acid derived from such an organism, cell or virus. Examples of bioagents include, but are not limited, to cells, including but not limited to human clinical samples, cell cultures, bacterial cells and other pathogens), viruses, viroids, fungi, protists, parasites, and pathogenicity markers (including but not limited to: pathogenicity islands, antibiotic resistance genes, virulence factors, toxin genes and other bioregulating compounds). Samples may be alive or dead or in a vegetative state (for example, vegetative bacteria or spores) and may be encapsulated or bioengineered. In the context of this invention, a "pathogen" is a bioagent which causes a disease or disorder.

As used herein, "intelligent primers" are primers that are designed to bind to highly conserved sequence regions of a bioagent identifying amplicon that flank an intervening variable region and yield amplification products which ideally provide enough variability to distinguish each individual bioagent, and which are amenable to molecular mass analysis. By the term "highly conserved," it is meant that the sequence regions exhibit between about 80-100%, or between about 90-100%, or between about 95-100% identity among all or at least 70%, at least 80%, at least 90%, at least 95%, or at least 99% of species or strains.

As used herein, "broad range survey primers" are intelligent primers designed to identify an unknown bioagent at the genus level. In some cases, broad range survey primers are able to identify unknown bioagents at the species or sub-species level. As used herein, "division-wide primers" are intelligent primers designed to identify a bioagent at the species level and "drill-down" primers are intelligent primers designed to identify a bioagent at the sub-species level. As used herein, the "sub-species" level of identification includes, but is not limited to, strains, subtypes, variants, and isolates.

As used herein, a "bioagent division" is defined as group of bioagents above the species level and includes but is not limited to, orders, families, classes, clades, genera or other such groupings of bioagents above the species level.

As used herein, a "sub-species characteristic" is a genetic characteristic that provides the means to distinguish two members of the same bioagent species. For example, one viral strain could be distinguished from another viral strain of the same species by possessing a genetic change (e.g., for example, a nucleotide deletion, addition or substitution) in one of the viral genes, such as the RNA-dependent RNA polymerase. In this case, the sub-species characteristic that can be identified using the methods of the present invention is the genetic change in the viral polymerase.

As used herein, the term "bioagent identifying amplicon" refers to a polynucleotide that is amplified from a bioagent in an amplification reaction whose sequence 1) ideally provides base composition variability to distinguish among individual bioagents and 2) whose molecular mass is amenable to molecular mass determination.

As used herein, a "base composition" is the exact number of each nucleobase (A, T, C and G) in a given sequence. As used herein, a "base composition signature" (BCS) is the exact base composition (i.e., the number of A, T, G and C nucleobases) determined from the molecular mass of a bioagent identifying amplicon.

As used herein, a "base composition probability cloud" is a representation of the diversity in base composition resulting from a variation in sequence that occurs among different isolates of a given species. The "base composition probability cloud" represents the base composition constraints for each species and is typically visualized using a pseudo four-dimensional plot.

As used herein, a "wobble base" is a variation in a codon found at the third nucleotide position of a DNA triplet. Variations in conserved regions of sequence are often found at the third nucleotide position due to redundancy in the amino acid code.

In the context of the present invention, the term "unknown bioagent" may mean either: (i) a bioagent whose existence is known (such as the well known bacterial species *Staphylo-*

*coccus aureus* for example) but which is not known to be in a sample to be analyzed, or (ii) a bioagent whose existence is not known (for example, the SARS coronavirus was unknown prior to April 2003). For example, if the method for identification of coronaviruses disclosed in commonly owned U.S. patent Ser. No. 10/829,826 (incorporated herein by reference in its entirety) was to be employed prior to April 2003 to identify the SARS coronavirus in a clinical sample, both meanings of "unknown" bioagent are applicable since the SARS coronavirus was unknown to science prior to April, 2003 and since it was not known what bioagent (in this case a coronavirus) was present in the sample. On the other hand, if the method of U.S. patent Ser. No. 10/829,826 was to be employed subsequent to April 2003 to identify the SARS coronavirus in a clinical sample, only the first meaning (i) of "unknown" bioagent would apply since the SARS coronavirus became known to science subsequent to April 2003 and since it was not known what bioagent was present in the sample.

As used herein, "triangulation identification" means the employment of more than one bioagent identifying amplicons for identification of a bioagent.

In the context of the present invention, "viral nucleic acid" includes, but is not limited to, DNA, RNA, or DNA that has been obtained from viral RNA, such as, for example, by performing a reverse transcription reaction. Viral RNA can either be single-stranded (of positive or negative polarity) or double-stranded.

As used herein, the term "etiology" refers to the causes or origins, of diseases or abnormal physiological conditions.

As used herein, the term "nucleobase" is synonymous with other terms in use in the art including "nucleotide," "deoxynucleotide," "nucleotide residue," "deoxynucleotide residue," "nucleotide triphosphate (NTP)," or deoxynucleotide triphosphate (dNTP).

Despite enormous biological diversity, all forms of life on earth share sets of essential, common features in their genomes. Since genetic data provide the underlying basis for identification of orthopoxvirus by the methods of the present invention, it is desirable to select segments of nucleic acids which ideally provide enough variability to distinguish each individual bioagent and whose molecular mass is amenable to molecular mass determination.

Unlike bacterial genomes, which exhibit conversation of numerous genes (i.e. housekeeping genes) across all organisms, viruses do not share a gene that is essential and conserved among all virus families. Therefore, viral identification is achieved within smaller groups of related viruses, such as members of a particular virus family or genus. For example, RNA-dependent RNA polymerase is present in all single-stranded RNA viruses and can be used for broad priming as well as resolution within the virus family.

Disclosed in U.S. Patent Application Publication Nos. 2003-0027135, 2003-0082539, 2003-0228571, 2004-0209260, 2004-0219517, and 2004-0180328, and in U.S. application Ser. Nos. 10/660,997, 10/728,486, 10/754,415, and 10/829,826, all of which are commonly owned and incorporated herein by reference in their entirety, are methods for identification of bioagents (any organism, cell, or virus, living or dead, or a nucleic acid derived from such an organism, cell or virus) in an unbiased manner by molecular mass and base composition analysis of "bioagent identifying amplicons" which are obtained by amplification of segments of essential and conserved genes which are involved in, for example, translation, replication, recombination and repair, transcription, nucleotide metabolism, amino acid metabolism, lipid metabolism, energy generation, uptake, secretion and the like. Examples of these proteins include, but are not limited to, ribosomal RNAs, ribosomal proteins, DNA and RNA polymerases, RNA-dependent RNA polymerases, RNA capping and methylation enzymes, elongation factors, tRNA synthetases, protein chain initiation factors, heat shock protein groEL, phosphoglycerate kinase, NADH dehydrogenase, DNA ligases, DNA gyrases and DNA topoisomerases, helicases, metabolic enzymes, and the like.

To obtain bioagent identifying amplicons, primers are selected to hybridize to conserved sequence regions which bracket or flank variable sequence regions to yield a segment of nucleic acid which can be amplified and which is amenable to methods of molecular mass analysis. The variable sequence regions provide the variability of molecular mass which is used for bioagent identification. Upon amplification by PCR or other amplification methods with the specifically chosen primers, an amplification product that represents a bioagent identifying amplicon is obtained. The molecular mass of the amplification product, obtained by mass spectrometry for example, provides the means to uniquely identify the bioagent without a requirement for prior knowledge of the possible identity of the bioagent. The molecular mass of the amplification product or the corresponding base composition (which can be calculated from the molecular mass of the amplification product) is compared with a database of molecular masses or base compositions and a match indicates the identity of the bioagent. Furthermore, the method can be applied to rapid parallel analyses (for example, in a multi-well plate format) the results of which can be employed in a triangulation identification strategy which is amenable to rapid throughput and does not require nucleic acid sequencing of the amplified target sequence for bioagent identification.

The result of determination of a previously unknown base composition of a previously unknown bioagent (for example, a newly evolved and heretofore unobserved virus) has downstream utility by providing new bioagent indexing information with which to populate base composition databases. The process of subsequent bioagent identification analyses is, thus, greatly improved as more base composition data for bioagent identifying amplicons becomes available.

In some embodiments of the present invention, at least one viral nucleic acid segment is amplified in the process of identifying the viral bioagent. Thus, the nucleic acid segments that can be amplified by the primers disclosed herein and that provide enough variability to distinguish each individual bioagent and whose molecular masses are amenable to molecular mass determination are herein described as viral bioagent identifying amplicons.

In some embodiments of the present invention, viral bioagent identifying amplicons comprise from about 45 to about 200 nucleobases (i.e. from about 45 to about 200 linked nucleosides; or up to about 200 nucleobases). One of ordinary skill in the art will appreciate that the invention embodies viral bioagent identifying amplicons of 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, and 200 nucleobases in length, or any range therewithin.

It is the combination of the portions of the viral bioagent nucleic acid segment to which the primers hybridize (hybridization sites) and the variable region between the primer hybridization sites that comprises the viral bioagent identifying amplicon.

In some embodiments, viral bioagent identifying amplicons amenable to molecular mass determination which are produced by the primers described herein are either of a length, size or mass compatible with the particular mode of molecular mass determination or compatible with a means of providing a predictable fragmentation pattern in order to obtain predictable fragments of a length compatible with the particular mode of molecular mass determination. Such means of providing a predictable fragmentation pattern of an amplification product include, but are not limited to, cleavage with restriction enzymes or cleavage primers, for example. Thus, in some embodiments, viral bioagent identifying amplicons are larger than 200 nucleobases and are amenable to molecular mass determination following restriction digestion. Methods of using restriction enzymes and cleavage primers are well known to those with ordinary skill in the art.

In some embodiments, amplification products corresponding to viral bioagent identifying amplicons are obtained using the polymerase chain reaction (PCR) which is a routine method to those with ordinary skill in the molecular biology arts. Other amplification methods may be used such as ligase chain reaction (LCR), low-stringency single primer PCR, and multiple strand displacement amplification (MDA). These methods are also well known to those with ordinary skill.

Intelligent primers are designed to bind to highly conserved sequence regions that flank an intervening variable region and yield viral bioagent identifying amplicons upon amplification, which ideally provide enough variability to distinguish each individual viral bioagent, and which are amenable to molecular mass analysis. In some embodiments, the highly conserved sequence regions exhibit between about 80-100%, or between about 90-100%, or between about 95-100% identity, or between about 99-100% identity. The molecular mass of a given amplification product provides a means of identifying the viral bioagent from which it was obtained, due to the variability of the variable region. Thus, design of intelligent primers requires selection of a variable region with appropriate variability to resolve the identity of a given bioagent. Viral bioagent identifying amplicons are ideally specific to the identity of the viral bioagent, however, this is not an absolute requirement because multiple viral bioagent identifying amplicons can be used in a triangulation strategy (vide infra).

Identification of viral bioagents can be accomplished at different taxonomic levels using intelligent primers suited to resolution of each individual level of identification. Broad range survey intelligent primers are designed with the objective of identifying a bioagent as a member of a particular division (e.g., an order, family, genus or other such grouping of viral bioagents above the species level). As a non-limiting example, members of the *Orthopoxvirus* genus may be identified as such by employing broad range survey intelligent primers such as primers which target RNA or DNA polymerases, helicases, or other viral genes. In some embodiments, broad range survey intelligent primers are capable of identification of bioagents at the species, sub-species or strain level.

Division-wide intelligent primers are designed with an objective of identifying a bioagent at the species level. Division-wide intelligent primers are not always required for identification at the species level because broad range survey intelligent primers may provide sufficient identification resolution to accomplishing this identification objective.

Drill-down intelligent primers are designed with the objective of identifying a bioagent at the sub-species level (including strains, subtypes, variants and isolates) based on subspecies characteristics. Drill-down intelligent primers are not always required for identification at the sub-species level because broad range survey intelligent primers may provide sufficient identification resolution to accomplishing this identification objective.

A representative process flow diagram used for primer selection and validation process is outlined in FIG. 1. For each group of organisms, candidate target sequences are identified (200) from which nucleotide alignments are created (210) and analyzed (220). Primers are then designed by selecting appropriate priming regions (230) which then enables the selection of candidate primer pairs (240). The primer pairs are then subjected to in silico analysis by electronic PCR (ePCR) (300) wherein bioagent identifying amplicons are obtained from sequence databases such as GenBank or other sequence collections (310) and checked for specificity in silico (320). Bioagent identifying amplicons obtained from GenBank sequences (310) can also be analyzed by a probability model which predicts the capability of a given amplicon to identify unknown bioagents such that the base compositions of amplicons with favorable probability scores are then stored in a base composition database (325). Alternatively, base compositions of the bioagent identifying amplicons obtained from the primers and GenBank sequences can be directly entered into the base composition database (330). Candidate primer pairs (240) are validated by in vitro amplification by a method such as PCR analysis (400) of nucleic acid from a collection of organisms (410). Amplification products thus obtained are analyzed to confirm the sensitivity, specificity and reproducibility of the primers used to obtain the amplification products (420).

Many of the important pathogens, including the organisms of greatest concern as biological weapons agents, have been completely sequenced. This effort has greatly facilitated the design of primers and probes for the detection of individual bioagents. Thus, the combination of broad-range priming with division-wide and drill-down priming described herein is being used very successfully in several applications of the technology, including environmental surveillance for biowarfare threat agents and clinical sample analysis for medically important pathogens.

Synthesis of primers is well known and routine in the art. The primers may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed.

The primers are employed as, for example, compositions for use in methods for identification of viral bioagents as follows: a primer pair composition is contacted with nucleic acid (such as, for example, DNA from a DNA virus, or DNA reverse transcribed from the RNA of an RNA virus) of an unknown viral bioagent. The nucleic acid is then amplified by a nucleic acid amplification technique, such as PCR for example, to obtain an amplification product that represents a viral bioagent identifying amplicon. The molecular mass of each strand of the double-stranded amplification product is determined by a molecular mass measurement technique such as, for example, mass spectrometry wherein the two strands of the double-stranded amplification product are separated during the ionization process. In some embodiments, the mass spectrometry is electrospray Fourier transform ion cyclotron resonance mass spectrometry (ESI-FTICR-MS) or electrospray time of flight mass spectrometry (ESI-TOF-MS). A list of possible base compositions can be generated for the molecular mass value obtained for each strand and the choice of the correct base composition from the list is facilitated by matching the base composition of one strand with a complementary base composition of the other strand. The molecular mass or base composition thus determined is then compared with a database of molecular masses or base compositions of analogous bioagent identifying amplicons for known viral bioagents. A match between the molecular mass or base composition of the amplification product and the molecular mass or base composition of an analogous bioagent identifying amplicon for a known viral bioagent indicates the presence and/or identity of the unknown bioagent. In some embodiments, the primer pair used is one of the primer pairs of Table 1. In some embodiments, the method is repeated using a different primer pair to resolve possible ambiguities in the identification process or to improve the confidence level for the identification assignment.

In some embodiments, a viral bioagent identifying amplicon may be produced using only a single primer (either the forward or reverse primer of any given primer pair), provided an appropriate amplification method is chosen, such as, for example, low stringency single primer PCR (LSSP-PCR). Adaptation of this amplification method in order to produce viral bioagent identifying amplicons can be accomplished by one with ordinary skill in the art without undue experimentation.

In some embodiments, the oligonucleotide primers are broad range survey primers which hybridize to conserved regions of nucleic acid encoding DNA polymerase, RNA polymerase, DNA helicase, RNA helicase, or thioredoxin-like gene of all (or between 80% and 100%, between 85% and 100%, between 90% and 100%, or between 95% and 100%) known orthopoxviruses and produce orthopoxvirus identifying amplicons. As used herein, the phrase "broad range survey primers" refers to primers that bind to nucleic acid encoding genes essential to orthopoxvirus replication (e.g., for example, DNA and RNA polymerases, RNA and RNA helicases and thioredoxin-like gene) of all (or between 80% and 100%, between 85% and 100%, between 90% and 100%, or between 95% and 100%) known species of orthopoxviruses. In some embodiments, the primer pairs comprise oligonucleotides ranging in length from 13 to 35 nucleobases, each of which have from 70% to 100% sequence identity with any of the primers shown in Table 1.

In some cases, the molecular mass or base composition of a viral bioagent identifying amplicon defined by a broad range survey primer pair does not provide enough resolution to unambiguously identify a viral bioagent at the species level. These cases benefit from further analysis of one or more viral bioagent identifying amplicons generated from at least one additional broad range survey primer pair or from at least one additional division-wide primer pair. The employment of more than one bioagent identifying amplicon for identification of a bioagent is herein referred to as "triangulation identification."

In other embodiments, the oligonucleotide primers are division-wide primers which hybridize to nucleic acid encoding genes of species within a genus of viruses. In other embodiments, the oligonucleotide primers are drill-down primers which enable the identification of sub-species characteristics. Drill down primers provide the functionality of producing bioagent identifying amplicons for drill-down analyses such as genotyping or strain typing when contacted with nucleic acid under amplification conditions. Identification of such sub-species characteristics is often critical for determining proper clinical treatment of viral infections. In some embodiments, sub-species characteristics are identified using only broad range survey primers and division-wide, and drill-down primers are not used.

In some embodiments, the primers used for amplification hybridize to and amplify genomic DNA, DNA of bacterial plasmids, DNA of DNA viruses or DNA reverse transcribed from RNA of an RNA virus.

In some embodiments, the primers used for amplification hybridize directly to viral RNA and act as reverse transcription primers for obtaining DNA from direct amplification of viral RNA. Methods of amplifying RNA using reverse transcriptase are well known to those with ordinary skill in the art and can be routinely established without undue experimentation.

One with ordinary skill in the art of design of amplification primers will recognize that a given primer need not hybridize with 100% complementarity in order to effectively prime the synthesis of a complementary nucleic acid strand in an amplification reaction. Moreover, a primer may hybridize over one or more segments such that intervening or adjacent segments are not involved in the hybridization event (e.g., for example, a loop structure or a hairpin structure). The primers of the present invention may comprise at least 70%, at least 75%, at least 80%, at least 85%, at least 90%, at least 95% or at least 99% sequence identity with any of the primers listed in Table 1. Thus, in some embodiments of the present invention, an extent of variation of 70% to 100%, or any range therewithin, of the sequence identity is possible relative to the specific primer sequences disclosed herein. Determination of sequence identity is described in the following example: a primer 20 nucleobases in length which differs in contiguous nucleobases from another 20 nucleobase primer by only two residues has 18 of 20 identical residues (18/20=0.9 or 90% sequence identity). In another example, a primer 15 nucleobases in length having all residues identical to a 15 nucleobase segment of another primer that is 20 nucleobases in length would have 15/20=0.75 or 75% sequence identity with the 20 nucleobase primer. In yet another example, a first primer, 35 nucleobases in length having a 20 nucleobase segment which is identical to the entire sequence of a second primer of a length of 20 nucleobases has 100% sequence identity with the second primer.

Percent homology, sequence identity or complementarity, can be determined by, for example, the Gap program (Wisconsin Sequence Analysis Package, Version 8 for UNIX, Genetics Computer Group, University Research Park, Madison Wis.), using default settings, which uses the algorithm of Smith and Waterman (Adv. Appl. Math., 1981, 2, 482-489). In some embodiments, complementarity of primers with respect to the conserved priming regions of viral nucleic acid is between about 70% and 100%. In other embodiments, homology, sequence identity or complementarity, is between about 80% and 100%. In yet other embodiments, homology, sequence identity or complementarity, is at least 90%, at least 92%, at least 94%, at least 95%, at least 96%, at least 97%, at least 98%, at least 99% or is 100%.

In some embodiments, the primers described herein comprise at least 70%, at least 75%, at least 80%, at least 85%, at least 90%, at least 92%, at least 94%, at least 95%, at least 96%, at least 98%, or at least 99%, or 100% (or any range therewithin) sequence identity with the primer sequences specifically disclosed herein. Thus, for example, a primer may have between 70% and 100%, between 75% and 100%, between 80% and 100%, and between 95% and 100% sequence identity with SEQ ID NO: 1. Likewise, a primer may have similar sequence identity with any other primer whose nucleotide sequence is disclosed in Table 1.

One with ordinary skill is able to calculate percent sequence identity or percent sequence homology and able to determine, without undue experimentation, the effects of variation of primer sequence identity on the function of the primer in its role in priming synthesis of a complementary strand of nucleic acid for production of an amplification product of a corresponding viral bioagent identifying amplicon.

In some embodiments of the present invention, the oligonucleotide primers are 13 to 35 nucleobases in length (13 to 35 linked nucleotide residues; or up to 35 nucleotide residues). These embodiments comprise oligonucleotide primers 13, 14, 15, 16, 17, 18, 19, 20, 21, 22, 23, 24, 25, 26, 27, 28, 29, 30, 31, 32, 33, 34 or 35 nucleobases in length, or any range therewithin.

In some embodiments, any given primer can comprise a modification comprising the addition of a non-templated T residue to the 5' end of the primer (i.e., the added T residue does not necessarily hybridize to the nucleic acid being amplified). The addition of a non-templated T residue has an effect of minimizing the addition of non-templated adenyl residues as a result of the non-specific enzyme activity of Taq polymerase (Magnuson et al., Biotechniques, 1996, 21, 700-709), an occurrence which may lead to ambiguous results arising from molecular mass analysis.

In some embodiments of the present invention, primers may contain one or more universal bases. Because any variation (due to codon wobble in the $3^{rd}$ position) in the conserved regions among species is likely to occur in the third position of a DNA (or RNA) triplet, oligonucleotide primers can be designed such that the nucleotide corresponding to this position is a base which can bind to more than one nucleotide, referred to herein as a "universal nucleobase." For example, under this "wobble" pairing, inosine (I) binds to U, C or A; guanine (G) binds to U or C, and uridine (U) binds to U or C. Other examples of universal nucleobases include, but are not limited to, nitroindoles such as 5-nitroindole or 3-nitropyrrole (Loakes et al., Nucleosides and Nucleotides, 1995, 14, 1001-1003), the degenerate nucleotides dP or dK (Hill et al., Proc. Natl. Acad. Sci. U.S.A., 1998, 95, 4258-4263), an acyclic nucleoside analog containing 5-nitroindazole (Van Aerschot et al., Nucleosides and Nucleotides, 1995, 14, 1053-1056) or the purine analog 1-(2-deoxy-β-D-ribofuranosyl)-imidazole-4-carboxamide (Sala et al., Nucl. Acids Res., 1996, 24, 3302-3306).

In some embodiments, to compensate for the somewhat weaker binding by the wobble base, the oligonucleotide primers are designed such that the first and second positions of each triplet are occupied by nucleotide analogs which bind with greater affinity than the unmodified nucleotide. Examples of these analogs include, but are not limited to, 2,6-diaminopurine which binds to thymine, 5-propynyluracil which binds to adenine and 5-propynylcytosine and phenoxazines, including G-clamp, which binds to G. Propynylated pyrimidines are described in U.S. Pat. Nos. 5,645,985, 5,830, 653 and 5,484,908, each of which is commonly owned and incorporated herein by reference in its entirety. Propynylated primers are described in U.S Patent Application Publication No. 2003-0170682, which is also commonly owned and incorporated herein by reference in its entirety. Phenoxazines are described in U.S. Pat. Nos. 5,502,177, 5,763,588, and 6,005,096, each of which is incorporated herein by reference in its entirety. G-clamps are described in U.S. Pat. Nos. 6,007, 992 and 6,028,183, each of which is incorporated herein by reference in its entirety.

In some embodiments, to enable broad priming of rapidly evolving RNA viruses, primer hybridization is enhanced using primers containing 5-propynyl deoxycytidine and deoxythymidine nucleotides. These modified primers offer increased affinity and base pairing selectivity.

In some embodiments, non-template primer tags are used to increase the melting temperature ($T_m$) of a primer-template duplex in order to improve amplification efficiency. A non-template tag is at least three consecutive A or T nucleotide residues on a primer which are not complementary to the template. In any given non-template tag, A can be replaced by C or G and T can also be replaced by C or G. Although Watson-Crick hybridization is not expected to occur for a non-template tag relative to the template, the extra hydrogen bond in a G-C pair relative to an A-T pair confers increased stability of the primer-template duplex and improves amplification efficiency for subsequent cycles of amplification when the primers hybridize to strands synthesized in previous cycles.

In other embodiments, propynylated tags may be used in a manner similar to that of the non-template tag, wherein two or more 5-propynylcytidine or 5-propynyluridine residues replace template matching residues on a primer. In other embodiments, a primer contains a modified internucleoside linkage such as a phosphorothioate linkage, for example.

In some embodiments, the primers contain mass-modifying tags. Reducing the total number of possible base compositions of a nucleic acid of specific molecular weight provides a means of avoiding a persistent source of ambiguity in determination of base composition of amplification products. Addition of mass-modifying tags to certain nucleobases of a given primer will result in simplification of de novo determination of base composition of a given bioagent identifying amplicon from its molecular mass.

In some embodiments of the present invention, the mass modified nucleobase comprises one or more of the following: for example, 7-deaza-2'-deoxyadenosine-5-triphosphate, 5-iodo-2'-deoxyuridine-5'-triphosphate, 5-bromo-2'-deoxyuridine-5'triphosphate, 5-bromo-2'-deoxycytidine-5'-triphosphate, 5-iodo-2'-deoxycytidine-5'-triphosphate, 5-hydroxy-2'-deoxyuridine-5'-triphosphate, 4-thiothymidine-5'-triphosphate, 5-aza-2'-deoxyuridine-5'-triphosphate, 5-fluoro-2'-deoxyuridine-5'-triphosphate, 06-methyl-2'-deoxyguanosine-5'-triphosphate, N2-methyl-2'-deoxyguanosine-5'-triphosphate, 8-oxo-2'-deoxyguanosine-5'-triphosphate, or thiothymidine-5'-triphosphate. In some embodiments, the mass-modified nucleobase comprises $^{15}$N or $^{13}$C or both $^{15}$N and $^{13}$C.

In some cases, a molecular mass of a given bioagent identifying amplicon alone does not provide enough resolution to unambiguously identify a given bioagent. The employment of more than one viral bioagent identifying amplicon for identification of a bioagent is herein referred to as triangulation identification. Triangulation identification is pursued by analyzing a plurality of bioagent identifying amplicons selected within multiple genes. This process is used to reduce false negative and false positive signals, and enable reconstruction of the origin of hybrid or otherwise engineered bioagents. For example, identification of the three part toxin genes typical of B. anthracis (Bowen et al., J. Appl. Microbiol., 1999, 87, 270-278) in the absence of the expected signatures from a representative orthopoxvirus genome would suggest a genetic engineering event.

In some embodiments, the triangulation identification process can be pursued by characterization of bioagent identifying amplicons in a massively parallel fashion using the polymerase chain reaction (PCR), such as multiplex PCR where multiple primers are employed in the same amplification reaction mixture, or PCR in multi-well plate format wherein a different and unique pair of primers is used in multiple wells containing otherwise identical reaction mixtures. Such multiplex and multi-well PCR methods are well known to those with ordinary skill in the arts of rapid throughput amplification of nucleic acids.

In some embodiments, the molecular mass of a given viral bioagent identifying amplicon is determined by mass spectrometry. Mass spectrometry has several advantages, not the least of which is high bandwidth characterized by the ability to separate (and isolate) many molecular peaks across a broad range of mass to charge ratio (m/z). Thus mass spectrometry is intrinsically a parallel detection scheme without the need for radioactive or fluorescent labels or probes, since every amplification product is identified by its molecular mass. The current state of the art in mass spectrometry is such that less than femtomole quantities of material can be readily analyzed to afford information about the molecular contents of the sample. An accurate assessment of the molecular mass of the material can be quickly obtained, irrespective of whether the molecular weight of the sample is several hundred, or in excess of one hundred thousand atomic mass units (amu) or Daltons.

In some embodiments, intact molecular ions are generated from amplification products using one of a variety of ionization techniques to convert the sample to gas phase. These ionization methods include, but are not limited to, electrospray ionization (ES), matrix-assisted laser desorption ionization (MALDI) and fast atom bombardment (FAB). Upon ionization, several peaks are observed from one sample due to the formation of ions with different charges. Averaging the multiple readings of molecular mass obtained from a single mass spectrum affords an estimate of molecular mass of the bioagent identifying amplicon. Electrospray ionization mass spectrometry (ESI-MS) is particularly useful for very high molecular weight polymers such as proteins and nucleic acids having molecular weights greater than 10 kDa, since it yields a distribution of multiply-charged molecules of the sample without causing a significant amount of fragmentation.

The mass detectors used in the methods of the present invention include, but are not limited to, Fourier transform ion cyclotron resonance mass spectrometry (FT-ICR-MS), time of flight (TOF), ion trap, quadrupole, magnetic sector, Q-TOF, and triple quadrupole.

Although the molecular mass of amplification products obtained using intelligent primers provides a means for identification of bioagents, conversion of molecular mass data to a base composition signature is useful for certain analyses. As used herein, a base composition signature (BCS) is the exact base composition determined from the molecular mass of a bioagent identifying amplicon. In one embodiment, a BCS provides an index of a specific gene in a specific organism. As used herein, a base composition is the exact number of each nucleobase (A, T, C and G).

RNA viruses depend on error-prone polymerases for replication and therefore their nucleotide sequences (and resultant base compositions) drift over time within the functional constraints allowed by selection pressure. Base composition probability distribution of a viral species or group represents a probabilistic distribution of the above variation in the A, C, G and T base composition space and can be derived by analyzing base compositions of, for example, all known isolates of that particular species.

In some embodiments, assignment of the likelihood that a previously unknown or un-indexed base composition corresponds to a particular virus, or a related member of a group of viruses is accomplished using base composition probability clouds or base composition density polyhedrons. Base compositions, like sequences, vary slightly from isolate to isolate within species or individual genotypes. It is possible to manage this diversity by building base composition probability clouds around the composition constraints for each species. This permits identification of organisms in a fashion similar to sequence analysis. A pseudo four-dimensional plot can be used to visualize the concept of base composition probability clouds. Likewise, a system of tetrahedral axes can be used to build a polyhedron according to seven base composition constraints. Optimal primer design requires optimal choice of bioagent identifying amplicons and maximizes the separation between the base composition signatures of individual bioagents. Areas where clouds overlap indicate regions that may result in a misclassification, a problem which is overcome by a triangulation identification process using bioagent identifying amplicons not affected by overlap of base composition probability clouds or density polyhedrons.

In some embodiments, pre-calculated base composition probability clouds provide the means for screening potential primer pairs in order to avoid potential misclassifications of base compositions. In other embodiments, base composition probability clouds provide the means for predicting the identity of a bioagent whose assigned base composition was not previously observed and/or indexed in a bioagent identifying amplicon base composition database due to evolutionary transitions in its nucleic acid sequence. Thus, in contrast to probe-based techniques, mass spectrometry determination of base composition does not require prior knowledge of the composition or sequence in order to make the measurement. Methods of calculating base composition probability clouds are described in U.S. Patent Application Publication No. 2004-0209260. Likewise methods of calculating base composition density polyhedrons are described in U.S. patent application Ser. No. 11/073,362.

The present invention provides bioagent classifying information similar to DNA sequencing and phylogenetic analysis at a level sufficient to identify a given bioagent. Furthermore, the process of determination of a previously unknown base composition for a given bioagent (for example, in a case where sequence information is unavailable) has downstream utility by providing additional bioagent indexing information with which to populate base composition databases. The process of future bioagent identification is, thus, greatly improved as more base compositions become available in base composition databases.

Figure 2:
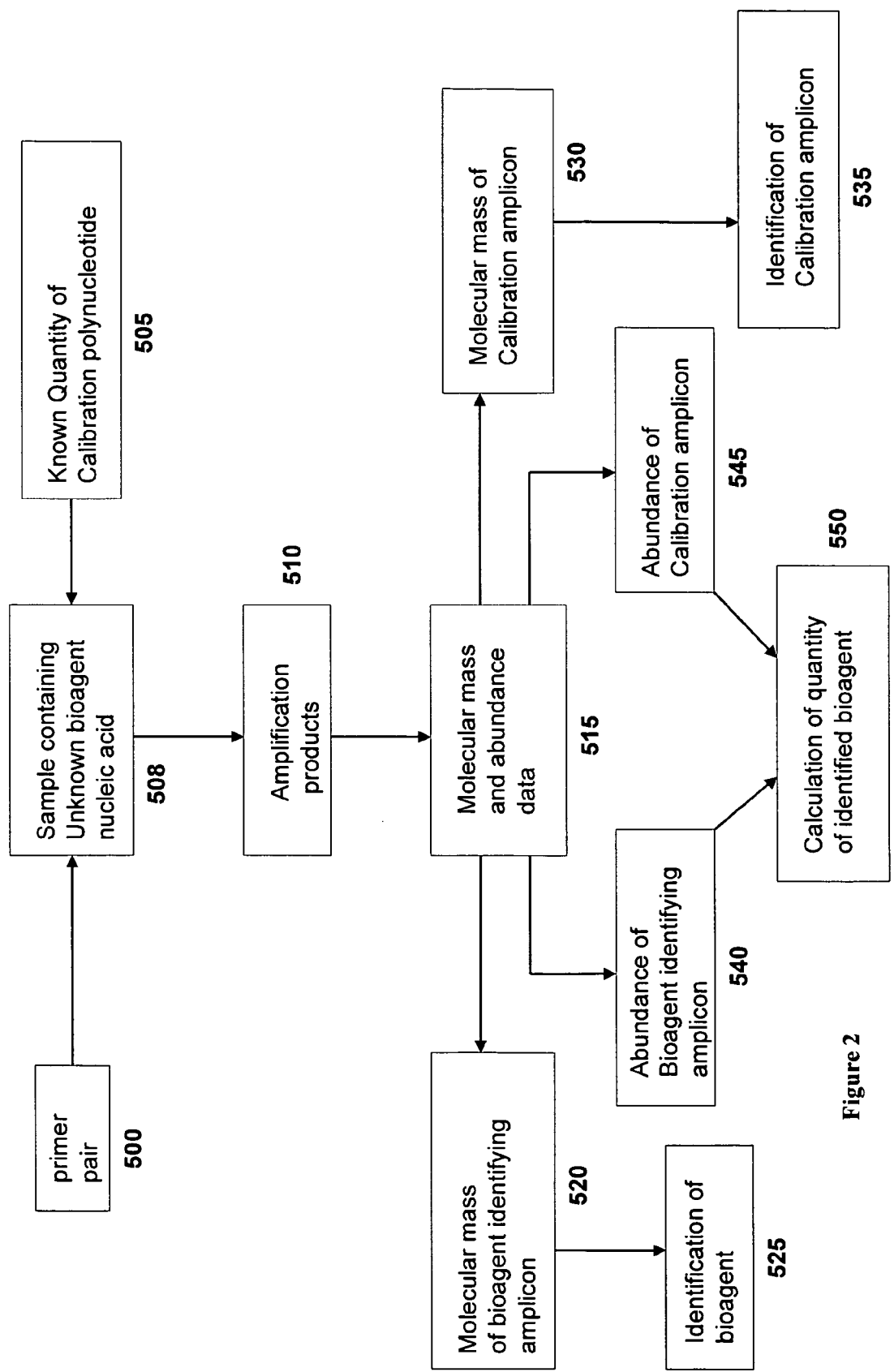
FIG. 2 is a representative process diagram for identification and determination of the quantity of a bioagent in a sample.
Figure 3:
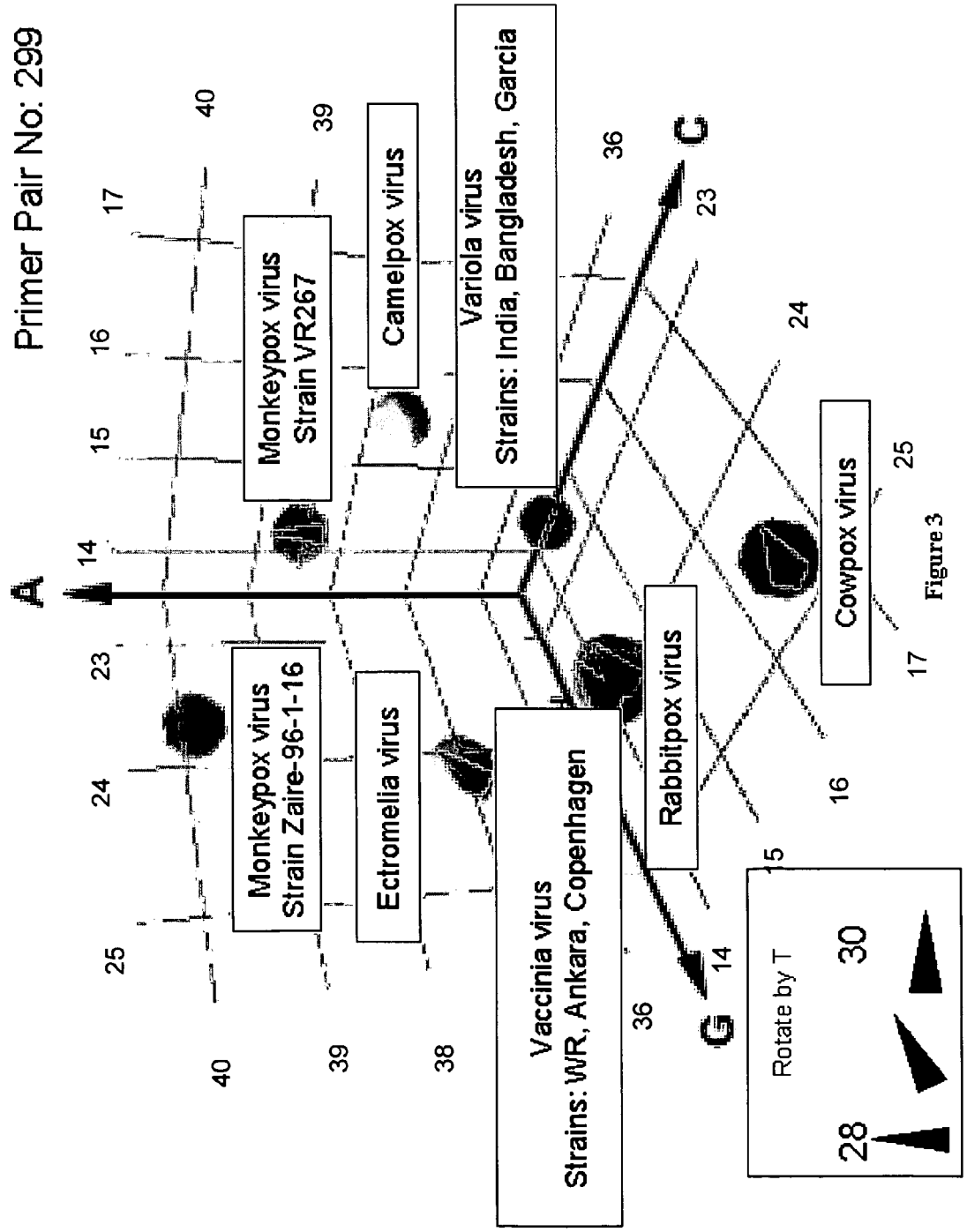
FIG. 3 is a pseudo 4-D plot of base compositions of orthopoxviruses obtained with primer pair number 299.
Figure 4:
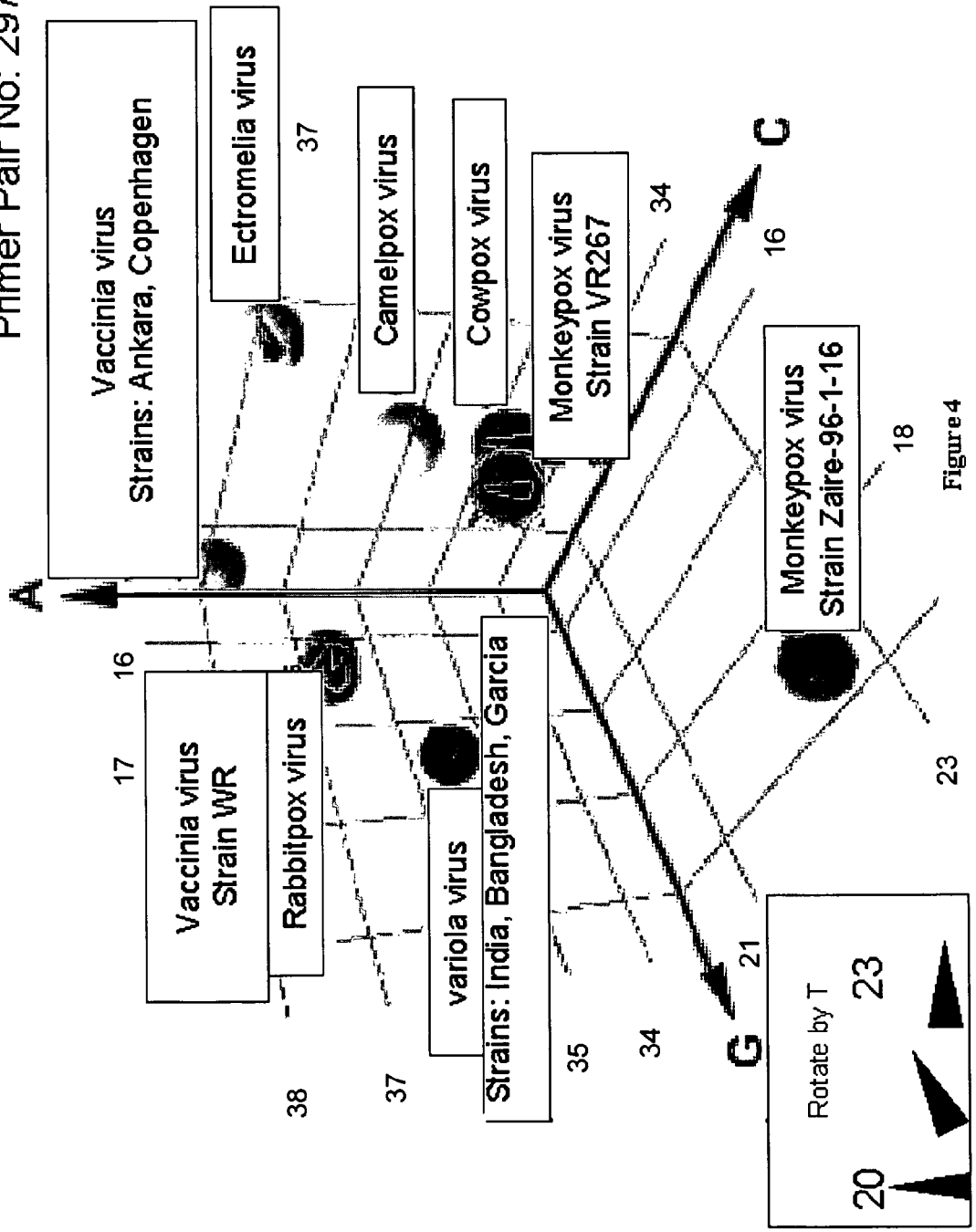
FIG. 4 is a pseudo 4-D plot of base compositions of orthopoxviruses obtained with primer pair number 297.

In some embodiments, the identity and quantity of an unknown bioagent can be determined using a representative process illustrated in FIG. 2. Primers (500) and a known quantity of a calibration polynucleotide (505) are added to a sample containing nucleic acid of an unknown bioagent (508). The total nucleic acid in the sample is then subjected to an amplification reaction to obtain amplification products (510). The molecular masses of amplification products are determined from which are obtained molecular mass and abundance data (515). The molecular mass of the bioagent identifying amplicon (520) provides the means for its identification (525) and the molecular mass of the calibration amplicon obtained from the calibration polynucleotide (530) provides the means for its identification (535). The abundance data of the bioagent identifying amplicon (540) is recorded and the abundance data for the calibration data (545) is recorded, both of which are used in a calculation which determines the quantity of unknown bioagent in the sample (550).

For concurrent identification and quantitation of an unknown bioagent, a sample comprising the unknown bioagent is contacted with a pair of primers which provide the means for amplification of nucleic acid from the bioagent, and a known quantity of a polynucleotide that comprises a calibration sequence. The nucleic acids of the bioagent and of the calibration sequence are amplified and the rate of amplification is reasonably assumed to be similar for the nucleic acid of the bioagent and of the calibration sequence. The amplification reaction then produces two amplification products: a bioagent identifying amplicon and a calibration amplicon. The bioagent identifying amplicon and the calibration amplicon should be distinguishable by molecular mass while being amplified at essentially the same rate. Effecting differential molecular masses can be accomplished by choosing as a calibration sequence, a representative bioagent identifying amplicon (from a specific species of bioagent) and performing, for example, a 2-8 nucleobase deletion or insertion within the variable region between the two priming sites. The amplified sample containing the bioagent identifying amplicon and the calibration amplicon is then subjected to molecular mass analysis by, for example, mass spectrometry. The resulting molecular mass analysis of the nucleic acid of the bioagent and of the calibration sequence provides molecular mass data and abundance data for the nucleic acid of the bioagent and of the calibration sequence. The molecular mass data obtained for the nucleic acid of the bioagent enables identification of the unknown bioagent and the abundance data enables calculation of the quantity of the bioagent, based on the knowledge of the quantity of calibration polynucleotide contacted with the sample.

In some embodiments, construction of a standard curve where the amount of calibration polynucleotide spiked into the sample is varied provides additional resolution and improved confidence for the determination of the quantity of bioagent in the sample. The use of standard curves for analytical determination of molecular quantities is well known to one with ordinary skill and can be performed without undue experimentation.

In some embodiments, multiplex amplification is performed where multiple bioagent identifying amplicons are amplified with multiple primer pairs which also amplify the corresponding standard calibration sequences. In this or other embodiments, the standard calibration sequences are optionally included within a single vector which functions as the calibration polynucleotide. Multiplex amplification methods are well known to those with ordinary skill and can be performed without undue experimentation. However, for the purpose of measurement of bioagent identifying amplicons by mass spectrometry, it is advantageous to ensure that no single strand of a double stranded bioagent identifying amplicon has a molecular mass substantially similar to another single strand present in the multiplex amplification mixture to avoid the presence of overlapping mass peaks in the resulting mass spectrum.

In some embodiments, the calibrant polynucleotide is used as an internal positive control to confirm that amplification conditions and subsequent analysis steps are successful in producing a measurable amplicon. Even in the absence of copies of the genome of a bioagent, the calibration polynucleotide should give rise to a calibration amplicon. Failure to produce a measurable calibration amplicon indicates a failure of amplification or subsequent analysis step such as amplicon purification or molecular mass determination. Reaching a conclusion that such failures have occurred is in itself, a useful event.

In some embodiments, the calibration sequence is comprised of DNA. In some embodiments, the calibration sequence is comprised of RNA.

In some embodiments, the calibration sequence is inserted into a vector which then itself functions as the calibration polynucleotide. In some embodiments, more than one calibration sequence is inserted into the vector that functions as the calibration polynucleotide. Such a calibration polynucleotide is herein termed a "combination calibration polynucleotide." The process of inserting polynucleotides into vectors is routine to those skilled in the art and can be accomplished without undue experimentation. Thus, it should be recognized that the calibration method should not be limited to the embodiments described herein. The calibration method can be applied for determination of the quantity of any bioagent identifying amplicon when an appropriate standard calibrant polynucleotide sequence is designed and used. The process of choosing an appropriate vector for insertion of a calibrant is also a routine operation that can be accomplished by one with ordinary skill without undue experimentation.

Bioagents that can be identified by the methods of the present invention include RNA viruses. The genomes of RNA viruses can be positive-sense single-stranded RNA, negative-sense single-stranded RNA or double-stranded RNA. Examples of RNA viruses with positive-sense single-stranded genomes include, but are not limited to members of the Caliciviridae, Picornaviridae, Flaviviridae, Togaviridae, Retroviridae and Coronaviridae families. Examples of RNA viruses with negative-sense single-stranded RNA genomes include, but are not limited to, members of the Filoviridae, Rhabdoviridae, Bunyaviridae, Orthomyxoviridae, Paramyxoviridae and Arenaviridae families. Examples of RNA viruses with double-stranded RNA genomes include, but are not limited to, members of the Reoviridae and Bimaviridae families.

In some embodiments of the present invention, RNA viruses are identified by first obtaining RNA from an RNA virus, or a sample containing or suspected of containing an RNA virus, obtaining corresponding DNA from the RNA by reverse transcription, amplifying the DNA to obtain one or more amplification products using one or more pairs of oligonucleotide primers that bind to conserved regions of the RNA viral genome, which flank a variable region of the genome, determining the molecular mass or base composition of the one or more amplification products and comparing the molecular masses or base compositions with calculated or experimentally determined molecular masses or base compositions of known RNA viruses, wherein at least one match identifies the RNA virus. Methods of isolating RNA from RNA viruses and/or samples containing RNA viruses, and reverse transcribing RNA to DNA are well known to those of skill in the art.

Orthopoxviruses represent DNA virus examples of viral bioagents which can be identified by the methods of the present invention. Orthopoxviruses are extremely diverse at the nucleotide and protein sequence levels and are thus difficult to detect and identify using currently available diagnostic techniques.

In some embodiments of the present invention, the orthopoxvirus target gene is DNA polymerase, RNA polymerase, DNA helicase, RNA helicase, or thioredoxin-like gene.

In other embodiments of the present invention, the intelligent primers produce bioagent identifying amplicons within stable and highly conserved regions of orthopoxvirus genomes. The advantage to characterization of an amplicon in a highly conserved region is that there is a low probability that the region will evolve past the point of primer recognition, in which case, the amplification step would fail. Such a primer set is, thus, useful as, for example, a broad range survey-type primer. In another embodiment of the present invention, the intelligent primers produce bioagent identifying amplicons in a region which evolves more quickly than the stable region described above. The advantage of characterization bioagent identifying amplicon corresponding to an evolving genomic region is that it is useful for distinguishing emerging strain variants.

The present invention also has significant advantages as a platform for identification of diseases caused by emerging viruses. The present invention eliminates the need for prior knowledge of bioagent sequence to generate hybridization probes. Thus, in another embodiment, the present invention provides a means of determining the etiology of a virus infection when the process of identification of viruses is carried out in a clinical setting and, even when the virus is a new species never observed before. This is possible because the methods are not confounded by naturally occurring evolutionary variations (a major concern for characterization of viruses which evolve rapidly) occurring in the sequence acting as the template for production of the bioagent identifying amplicon. Measurement of molecular mass and determination of base composition is accomplished in an unbiased manner without sequence prejudice.

Another embodiment of the present invention also provides a means of tracking the spread of any species or strain of virus when a plurality of samples obtained from different locations are analyzed by the methods described above in an epidemiological setting. In one embodiment, a plurality of samples from a plurality of different locations is analyzed with primers which produce viral bioagent identifying amplicons, a subset of which contains a specific virus. The corresponding locations of the members of the virus-containing subset indicate the spread of the specific virus to the corresponding locations.

The present invention also provides kits for carrying out the methods described herein. In some embodiments, the kit may comprise a sufficient quantity of one or more primer pairs to perform an amplification reaction on a target polynucleotide from a bioagent to form a bioagent identifying amplicon. In some embodiments, the kit may comprise from one to fifty primer pairs, from one to twenty primer pairs, from one to ten primer pairs, or from two to five primer pairs. In some embodiments, the kit may comprise one or more, two or more, three or more, or four or more primer pairs, wherein each member of the pair is of a length of 13 to 35 nucleobases and has 70% to 100% sequence identity with any of the primers recited in Table 1.

In some embodiments, the kit may comprise one or more broad range survey primer(s), division wide primer(s), or drill-down primer(s), or any combination thereof. A kit may be designed so as to comprise particular primer pairs for identification of a particular bioagent. For example, a broad range survey primer kit may be used initially to identify an unknown bioagent as a member of the *Orthopoxvirus* genus. Another example of a division-wide kit may be used to distinguish Bangladesh 1975, India-1967 and Garcia-1966 strains of variola virus from each other. A drill-down kit may be used, for example, to distinguish different subtypes or genotypes of orthopoxviruses. In some embodiments, any of these kits may be combined to comprise a combination of broad range survey primers and division-wide primers so as to be able to identify the species of an unknown bioagent.

In some embodiments, the kit may contain standardized calibration polynucleotides for use as internal amplification calibrants. Internal calibrants are described in commonly owned U.S. patent application Ser. No. 60/545,425, which is incorporated herein by reference in its entirety.

In some embodiments, the kit may also comprise a sufficient quantity of reverse transcriptase (if an RNA virus is to be identified for example), a DNA polymerase, suitable nucleoside triphosphates (including any of those described above), a DNA ligase, and/or reaction buffer, or any combination thereof, for the amplification processes described above. A kit may further include instructions pertinent for the particular embodiment of the kit, such instructions describing the primer pairs and amplification conditions for operation of the method. A kit may also comprise amplification reaction containers such as microcentrifuge tubes and the like. A kit may also comprise reagents or other materials for isolating bioagent nucleic acid or bioagent identifying amplicons from amplification, including, for example, detergents, solvents, or ion exchange resins which may be linked to magnetic beads. A kit may also comprise a container such as a 96-well plate. A kit may also comprise a table of measured or calculated molecular masses and/or base compositions of bioagents using the primer pairs of the kit.

While the present invention has been described with specificity in accordance with certain of its embodiments, the following examples serve only to illustrate the invention and are not intended to limit the same. In order that the invention disclosed herein may be more efficiently understood, examples are provided below. It should be understood that these examples are for illustrative purposes only and are not to be construed as limiting the invention in any manner.

EXAMPLES

Example 1

Orthopoxvirus Identifying Amplicons

For design of primers that define orthopoxvirus identifying amplicons, all available sequences for members of the *Orthopoxvirus* genus were obtained from GenBank and the Poxvirus database (world wide web at poxvirus.org) and aligned and scanned for regions where pairs of PCR primers would amplify products between about 45 to about 200 nucleotides in length and distinguish species and/or sub-species from each other by their molecular masses or base compositions. A typical process shown in FIG. 1 is employed.

A database of expected base compositions for each primer region is generated using an in silico PCR search algorithm, such as (ePCR). An existing RNA structure search algorithm (Macke et al., Nucl. Acids Res., 2001, 29, 4724-4735, which is incorporated herein by reference in its entirety) has been modified to include PCR parameters such as hybridization conditions, mismatches, and thermodynamic calculations (SantaLucia, Proc. Natl. Acad. Sci. U.S.A., 1998, 95, 1460-1465, which is incorporated herein by reference in its entirety). This also provides information on primer specificity of the selected primer pairs.

Table 1 represents a collection of primers (sorted by forward primer name) designed to identify orthopoxviruses using the methods described herein. Primer sites were identified on five essential genes: DNA polymerase (E9L), RNA polymerase (A24R) DNA helicase (A18R), RNA helicase (K8R) and thioredoxin-like gene (A25L). The forward or reverse primer name shown in Table 1 indicates the gene region of the viral genome to which the primer hybridizes relative to a reference sequence. For example, the forward primer name K8R_NC001611_221_238_F indicates a forward primer "_F" that hybridizes to residues 221-238 of an orthopoxvirus reference sequence represented by GenBank Accession No. NC001611. In Table 1, $T^a$=5-propynyluracil (a propynylated version of T); and $C^a$=5-propynylcytosine (a propynylated version of C). The primer pair number is an in-house database index number.

TABLE 1

Primer Pairs for Identification of Orthopoxvirus Bioagents

| Primer Pair Number | Forward Primer Name | Forward Sequence | For SEQ ID NO: | Reverse Primer Name | Reverse Sequence | R TABLE 1-continued Primer Pairs for Identification of Orthopoxvirus Bioagents

| Primer Pair Number | Forward Primer Name | Forward Sequence | For SEQ ID NO: | Reverse Primer Name | Reverse Sequence | Rev SEQ ID NO: |
|---|---|---|---|---|---|---|
| 493 | A24R_NC001611_794_817P_F | TCGCGAT<sup>a</sup>AAT<sup>a</sup>AGATAGT<sup>a</sup>GC<sup>a</sup>T<sup>a</sup>AAAC | 12 | A24R_NC001611_860_879P_R | TGCTTC<sup>a</sup>C<sup>a</sup>AC<sup>a</sup>CAGGT<sup>a</sup>CAT<sup>a</sup>TAA | 35 |
| 979 | A18R_NC001611_90_117_F | TGATTTCGTAGAAGTTGAACCGGGATCA | 13 | A18R_NC001611_187_217_R | TCGCGATTTTATTATCGGTCGTTGTTAATGT | 36 |
| 980 | A18R_NC001611_91_117_F | TTCTCCCTAGAAGTTGAACCGGGATCA | 14 | A18R_NC001611_187_216_R | TCCCTCCCTATTATCGGTCGTTGTTAATGT | 37 |
| 981 | E9L_NC001611_1113_1133_F | TGGTGACGATACTACGGACGC | 15 | E9L_NC001611_1201_1235_R | TCCCTCCCAATATCTTTACGAATTACTTTACATAT | 38 |
| 982 | E9L_NC001611_1112_1133_F | TCGGTGACGATACTACGGACGC | 16 | E9L_NC001611_1205_1235_R | TCCTCCCTCCCATCTTTACGAATTACTTTAC | 39 |
| 983 | E9L_NC001611_1112_1133_F | TCGGTGACGATACTACGGACGC | 17 | E9L_NC001611_1205_1238_R | TCCTCCCTCCCAATATCTTTACGAATTACTTTAC | 40 |
| 984 | K8R_NC001611_207_238_F | TGGAAAAAAAGTATCTCCTCCATCACTAGGAA | 18 | K8R_NC001611_290_324_R | TCCCTCCCGAAAACTATAACATTCAAAGCTTATTG | 41 |
| 985 | K8R_NC001611_211_242_F | TGGAAAGTATCTCCTCCATCACTAGGAAAACC | 19 | K8R_NC000611_290_322_R | TCCCTCCCTCCCTATAACATTCAAAGCTTATTG | 42 |
| 986 | K8R_NC001611_213_238_F | TCCCTCCTCTCCTCCATCACTAGGAA | 20 | K8R_NC001611_290_319_R | TCCTCCCTCCCTAACATTCAAAGCTTATTG | 43 |
| 987 | A24R_NC001611_786_818_F | TCTAGTAAACGCGATAATAGATAGTGCTAAACG | 21 | A24R_NC001611_860_884_R | TGTTCAGCTTCCACCAGGTCATTAA | 44 |
| 988 | A24R_NC001611_788_818_F | TCCTCCTCGCGATAATAGATAGTGCTAAACG | 22 | A24R_NC001611_860_886_R | TGTGTTCAGCTTCCACCAGGTCATTAA | 45 |
| 989 | A24R_NC001611_789_817_F | TCCTCCCGCGATAATAGATAGTGCTAAAC | 23 | A24R_NC001611_860_883_R | TCCCAGCTTCCACCAGGTCATTAA | 46 |
| 1066 | A18R_NC001611_90_117_F | TGATTTCGTAGAAGTTGAACCGGGATCA | 13 | A18R_NC001611_187_216_R | TCCCTCCCTATTATCGGTCGTTGTTAATGT | 37 |
| 1067 | A18R_NC001611_91_117_F | TTCTCCCTAGAAGTTGAACCGGGATCA | 14 | A18R_NC001611_187_217_R | TCGCGATTTTATTATCGGTCGTTGTTAATGT | 36 |

Example 2

DNA Isolation and Amplification

Genomic materials from culture samples or swabs are prepared using the DNeasy® 96 Tissue Kit (Qiagen, Valencia, Calif.). All PCR reactions are assembled in 50 µl reactions in a 96 well microtiter plate format using a Packard MPII liquid handling robotic platform and MJ Dyad® thermocyclers (MJ research, Waltham, Mass.). The PCR reaction consists of 4 units of Amplitaq Gold®, 1× buffer II (Applied Biosystems, Foster City, Calif.), 1.5 mM $MgCl_2$, 0.4 M betaine, 800 µM of dNTP mixture, and 250 nM of each primer.

The following PCR conditions can be used to amplify the sequences used for mass spectrometry analysis: 95° C. for 10 minutes followed by 8 cycles of 95° C. for 30 seconds, 48° C. for 30 seconds, and 72° C. for 30 seconds, with the 48° C. annealing temperature increased 0.9° C. after each cycle. The PCR is then continued for 37 additional cycles of 95° C. for 15 seconds, 56° C. for 20 seconds, and 72° C. for 20 seconds

Example 3

Solution Capture Purification of PCR Products for Mass Spectrometry with Ion Exchange Resin-Magnetic Beads For solution capture of nucleic acids with ion exchange resin linked to magnetic beads, 25 µl of a 2.5 mg/mL suspension of BioClon amine terminated supraparamagnetic beads were added to 25 to 50 µl of a PCR (or RT-PCR) reaction containing approximately 10 pM of a typical PCR amplification product. The above suspension was mixed for approximately 5 minutes by vortexing or pipetting, after which the liquid was removed after using a magnetic separator. The beads containing bound PCR amplification product were then washed 3 times with 50 mM ammonium bicarbonate/50% MeOH or 100 mM ammonium bicarbonate/50% MeOH, followed by three more washes with 50% MeOH. The bound PCR amplicon was eluted with 25 mM piperidine, 25 mM imidazole, 35% MeOH, plus peptide calibration standards.

Example 4

Mass Spectrometry and Base Composition Analysis

The ESI-FTICR mass spectrometer is based on a Bruker Daltonics (Billerica, Mass.) Apex II 70e electrospray ionization Fourier transform ion cyclotron resonance mass spectrometer that employs an actively shielded 7 Tesla superconducting magnet. The active shielding constrains the majority of the fringing magnetic field from the superconducting magnet to a relatively small volume. Thus, components that might be adversely affected by stray magnetic fields, such as CRT monitors, robotic components, and other electronics, can operate in close proximity to the FTICR spectrometer. All aspects of pulse sequence control and data acquisition were performed on a 600 MHz Pentium II data station running Bruker's Xmass software under Windows NT 4.0 operating system. Sample aliquots, typically 15 µl, were extracted directly from 96-well microtiter plates using a CTC HTS PAL autosampler (LEAP Technologies, Carrboro, N.C.) triggered by the FTICR data station. Samples were injected directly into a 10 µl sample loop integrated with a fluidics handling system that supplies the 100 µl/hr flow rate to the ESI source. Ions were formed via electrospray ionization in a modified Analytica (Branford, Conn.) source employing an off axis, grounded electrospray probe positioned approximately 1.5 cm from the metalized terminus of a glass desolvation capillary. The atmospheric pressure end of the glass capillary was biased at 6000 V relative to the ESI needle during data acquisition. A counter-current flow of dry $N_2$ was employed to assist in the desolvation process. Ions were accumulated in an external ion reservoir comprised of an rf-only hexapole, a skimmer cone, and an auxiliary gate electrode, prior to injection into the trapped ion cell where they were mass analyzed. Ionization duty cycles >99% were achieved by simultaneously accumulating ions in the external ion reservoir during ion detection. Each detection event consisted of 1M data points digitized over 2.3 s. To improve the signal-to-noise ratio (S/N), 32 scans were co-added for a total data acquisition time of 74 s.

The ESI-TOF mass spectrometer is based on a Bruker Daltonics MicroTOF™. Ions from the ESI source undergo orthogonal ion extraction and are focused in a reflectron prior to detection. The TOF and FTICR are equipped with the same automated sample handling and fluidics described above. Ions are formed in the standard MicroTOF™ ESI source that is equipped with the same off-axis sprayer and glass capillary as the FTICR ESI source. Consequently, source conditions were the same as those described above. External ion accumulation was also employed to improve ionization duty cycle during data acquisition. Each detection event on the TOF was comprised of 75,000 data points digitized over 75 µs.

The sample delivery scheme allows sample aliquots to be rapidly injected into the electrospray source at high flow rate and subsequently be electrosprayed at a much lower flow rate for improved ESI sensitivity. Prior to injecting a sample, a bolus of buffer was injected at a high flow rate to rinse the transfer line and spray needle to avoid sample contamination/carryover. Following the rinse step, the autosampler injected the next sample and the flow rate was switched to low flow. Following a brief equilibration delay, data acquisition commenced. As spectra were co-added, the autosampler continued rinsing the syringe and picking up buffer to rinse the injector and sample transfer line. In general, two syringe rinses and one injector rinse were required to minimize sample carryover. During a routine screening protocol a new sample mixture was injected every 106 seconds. More recently a fast wash station for the syringe needle has been implemented which, when combined with shorter acquisition times, facilitates the acquisition of mass spectra at a rate of just under one spectrum/minute.

Raw mass spectra were post-calibrated with an internal mass standard and deconvoluted to monoisotopic molecular masses. Unambiguous base compositions were derived from the exact mass measurements of the complementary single-stranded oligonucleotides. Quantitative results are obtained by comparing the peak heights with an internal PCR calibration standard present in every PCR well at 500 molecules per well. Calibration methods are commonly owned and disclosed in U.S. Provisional Patent Application Ser. No. 60/545,425.

Example 5

De Novo Determination of Base Composition of Amplification Products using Molecular Mass Modified Deoxynucleotide Triphosphates Because the molecular masses of the four natural nucleobases have a relatively narrow molecular mass range (A=313.058, G=329.052, C=289.046, T=304.046—See Table 2), a persistent source of ambiguity in assignment of base composition can occur as follows: two nucleic acid strands having different base composition may have a difference of about 1 Da when the base composition difference between the two strands is G↔A (−15.994) combined with C↔T (+15.000). For example, one 99-mer nucleic acid strand having a base composition of $A_{27}G_{30}C_{21}T_{21}$ has a theoretical molecular mass of 30779.058 while another 99-mer nucleic acid strand having a base composition of $A_{26}G_{31}C_{22}T_{20}$ has a theoretical molecular mass of 30780.052. A 1 Da difference in molecular mass may be within the experimental error of a molecular mass measurement and thus, the relatively narrow molecular mass range of the four natural nucleobases imposes an uncertainty factor.

The present invention provides for a means for removing this theoretical 1 Da uncertainty factor through amplification of a nucleic acid with one mass-tagged nucleobase and three natural nucleobases. The term "nucleobase" as used herein is synonymous with other terms in use in the art including "nucleotide," "deoxynucleotide," "nucleotide residue," "deoxynucleotide residue," "nucleotide triphosphate (NTP)," or deoxynucleotide triphosphate (dNTP).

Addition of significant mass to one of the 4 nucleobases (dNTPs) in an amplification reaction, or in the primers themselves, will result in a significant difference in mass of the resulting amplification product (significantly greater than 1 Da) arising from ambiguities arising from the G↔A combined with C↔T event (Table 2). Thus, the same the G↔A (−15.994) event combined with 5-Iodo-C↔T (−110.900) event would result in a molecular mass difference of 126.894. If the molecular mass of the base composition $A_{27}G_{30}$ 5-Iodo-$C_{21}T_{21}$ (33422.958) is compared with $A_{26}G_{31}$ 5-Iodo-$C_{22}T_{20}$, (33549.852) the theoretical molecular mass difference is +126.894. The experimental error of a molecular mass measurement is not significant with regard to this molecular mass difference. Furthermore, the only base composition consistent with a measured molecular mass of the 99-mer nucleic acid is $A_{27}G_{30}$5-Iodo-$C_{21}T_{21}$. In contrast, the analogous amplification without the mass tag has 18 possible base compositions.

TABLE 2

Molecular Masses of Natural Nucleobases and the Mass-Modified Nucleobase 5-Iodo-C and Molecular Mass Differences Resulting from Transitions

| Nucleobase | Molecular Mass | Transition | Δ Molecular Mass |
|---|---|---|---|
| A | 313.058 | A-->T | −9.012 |
| A | 313.058 | A-->C | −24.012 |
| A | 313.058 | A-->5-Iodo-C | 101.888 |
| A | 313.058 | A-->G | 15.994 |
| T | 304.046 | T-->A | 9.012 |
| T | 304.046 | T-->C | −15.000 |
| T | 304.046 | T-->5-Iodo-C | 110.900 |
| T | 304.046 | T-->G | 25.006 |
| C | 289.046 | C-->A | 24.012 |
| C | 289.046 | C-->T | 15.000 |
| C | 289.046 | C-->G | 40.006 |
| 5-Iodo-C | 414.946 | 5-Iodo-C-->A | −101.888 |
| 5-Iodo-C | 414.946 | 5-Iodo-C-->T | −110.900 |
| 5-Iodo-C | 414.946 | 5-Iodo-C-->G | −85.894 |
| G | 329.052 | G-->A | −15.994 |
| G | 329.052 | G-->T | −25.006 |
| G | 329.052 | G-->C | −40.006 |
| G | 329.052 | G-->5-Iodo-C | 85.894 |

Example 6

Data Processing

Mass spectra of bioagent identifying amplicons are analyzed independently using a maximum-likelihood processor, such as is widely used in radar signal processing. This processor, referred to as GenX, first makes maximum likelihood estimates of the input to the mass spectrometer for each primer by running matched filters for each base composition aggregate on the input data. This includes the GenX response to a calibrant for each primer.

The algorithm emphasizes performance predictions culminating in probability-of-detection versus probability-of-false-alarm plots for conditions involving complex backgrounds of naturally occurring organisms and environmental contaminants. Matched filters consist of a priori expectations of signal values given the set of primers used for each of the bioagents. A genomic sequence database is used to define the mass base count matched filters. The database contains the sequences of known bacterial bioagents and includes threat organisms as well as benign background organisms. The latter is used to estimate and subtract the spectral signature produced by the background organisms.

A maximum likelihood detection of known background organisms is implemented using matched filters and a running-sum estimate of the noise covariance. Background signal strengths are estimated and used along with the matched filters to form signatures which are then subtracted. The maximum likelihood process is applied to this "cleaned up" data in a similar manner employing matched filters for the organisms and a running-sum estimate of the noise-covariance for the cleaned up data.

The amplitudes of all base compositions of bioagent identifying amplicons for each primer are calibrated and a final maximum likelihood amplitude estimate per organism is made based upon the multiple single primer estimates. Models of all system noise are factored into this two-stage maximum likelihood calculation. The processor reports the number of molecules of each base composition contained in the spectra. The quantity of amplification product corresponding to the appropriate primer set is reported as well as the quantities of primers remaining upon completion of the amplification reaction.

Example 7

Identification of Members of the Viral Genus *Orthopoxvirus*

DNA for five different test orthopoxvirus species from the laboratory of Dr. Chris Upton at University of Victoria, British Columbia, Canada: monkeypox (MPXV-VR267), cowpox (BR), rabbitpox (Utrecht), vaccinia (WR) and ectromelia (Moscow). PCR products corresponding to orthopoxvirus identifying amplicons were generated according to Example 2 from each of the test viruses using primer pair nos: 296, 297, 299, 310, 312 and 313 (Table 1). PCR products were purified according to Example 3 and analyzed by mass spectrometry according to Example 4 with data processing according to Example 6.

Spectra were processed by an algorithm that converts molecular mass to base composition data. All detected masses could be unambiguously mapped to specific base compositions, which were compared to the pre-compiled database of expected products from each of these viruses. FIG. 3 (primer pair number 299) and FIG. 4 (primer pair number 297) show the deconvoluted base compositions (solid cones) of the experimentally measured spectra in a three-dimensional plot (A, G, C axes, with the T counts represented by the tilt of the cone), overlaid on the expected base count distributions (hollow spheres) of the orthopoxvirus species where sequence data was available. Compositions for the test strains are shown as a solid cone projected onto the same plot. The experimentally determined base compositions with compositions expected from the sequences in GenBank for all five viruses tested. Vaccinia and ectromelia viruses gave expected products consistent with the database sequence entry in each primer region. In the case of the rabbitpox virus, the sequence of the target region was identical to vaccinia virus in all primer regions selected and not distinguished by the primers described above.

At the time of primer design, the only strain of monkeypox virus deposited in GenBank was the Zaire 96_I-16 strain. The experimentally determined base compositions for the MPX-VVR267 strain were different from those for the Zaire strain. The experimentally determined based-counts were subsequently validated by comparison to the full genome sequence for the VR267 strain (unpublished results—Chris Upton, University of Victoria). Thus a new variant of a known orthopoxvirus species was identified with the same technology used for primary detection, without the requirement of additional analysis and/or design.

A whole genome sequence for a new strain of cowpox, GRI-90 strain was published as these experiments were in progress. Analysis of several conserved genes across all of the orthopoxvirus genera revealed that this strain was closer to vaccinia strains than it was to the previously known Brighton Red strains of cowpox. The material that was tested in the lab was clearly the BR strain as evidenced by the perfect match to the expected base counts for these in the database.

Table 3 shows the expected base counts of the various orthopoxvirus species for all primer regions tested. The isolates used in this test are indicated. In every test instance, the experimentally measured signals matched database predicted base compositions. While a single primer target region might not resolve all species unambiguously, species can clearly be clearly identified and differentiated from one another using the triangulation strategy with multiple orthopoxvirus identifying amplicons obtained from priming of different genetic loci. For example, primer pair no. 310 does not distinguish the CMS and M-92(2) strains of Camelpox virus but primer pair 296 does distinguish these two strains because it produces two distinct base compositions.

TABLE 3

Orthopoxvirus Species Base Compositions for Primer Pair Nos: 296, 297, 299, 310, 312 and 313

| Orthopoxvirus Species and GenBank Accession | Strain | Primer Pair No: 310 | Primer Pair No: 296 | Primer Pair No: 313 [A G C T] | Primer Pair No: 299 | Primer Pair No: 312 | Primer Pair No: 297 |
|---|---|---|---|---|---|---|---|
| Camelpox virus AY009089 | CMS | A38 G11 C23 T19 | A32 G20 C23 T33 | A29 G15 C14 T26 | A38 G23 C16 T30 | A30 G19 C18 T33 | A37 G17 C22 T22 |
| Camelpox virus AF438165 | M-96 | A38 G11 C23 T19 | A32 G19 C23 T34 | A29 G15 C14 T26 | A38 G23 C16 T30 | A30 G19 C18 T33 | A37 G17 C22 T22 |
| Cowpox virus AF482758 | Brighton Red | A33 G14 C18 T26 | A36 G18 C23 T31 | A29 G15 C16 T24 | A36 G25 C17 T29 | A25 G24 C21 T30 | A36 G17 C22 T20 |
| Cowpox virus X94355 | GRI-90 | A37 G11 C24 T19 | A33 G19 C24 T32 | A30 G15 C13 T26 | A36 G25 C17 T29 | A27 G23 C19 T31 | A36 G18 C22 T22 |
| Ectromelia virus AF012825 | Moscow | A34 G13 C17 T27 | A33 G19 C24 T32 | A30 G15 C13 T26 | A38 G25 C15 T29 | A27 G22 C19 T32 | A38 G16 C22 T22 |
| Monkeypox virus A603973 | WR-267 | A34 G14 C18 T25 | A33 G20 C22 T33 | A29 G15 C15 T25 | A39 G24 C16 T28 | A28 G20 C21 T34 | A36 G17 C22 T20 |
| Monkeypox virus AF380138 | Zaire -96-I-16 | A34 G14 C18 T25 | A33 G20 C22 T33 | A28 G16 C15 T25 | A40 G24 C14 T29 | A28 G20 C21 T34 | A34 G19 C22 T20 |
| Vaccinia virus M35027 | Copenhagen | A38 G10 C24 T19 | A32 G21 C24 T31 | A30 G15 C13 T26 | A37 G25 C16 T29 | A25 G23 C20 T31 | A38 G16 C21 T23 |
| Vaccinia virus AF095689 | Tian Tan | A36 G12 C24 T19 | A32 G21 C24 T31 | A30 G15 C13 T26 | A37 G25 C16 T29 | A27 G22 C19 T31 | A38 G16 C21 T23 |
| Vaccinia virus AY243312 | Western Reserve | A36 G12 C24 T19 | A33 G20 C23 T32 | A30 G15 C13 T26 | A37 G25 C16 T29 | A27 G23 C18 T32 | A37 G17 C21 T23 |
| Vaccinia virus U94848 | Ankara | A36 G12 C24 T19 | A33 G20 C23 T32 | A30 G15 C13 T26 | A37 G25 C16 T29 | A25 G24 C20 T31 | A38 G16 C21 T23 |
| Vaccinia virus AY484669 | Rabbitpox Utrecht | A36 G12 C24 T19 | A33 G20 C23 T32 | A30 G15 C13 T26 | A37 G25 C16 T29 | A25 G24 C20 T31 | A37 G17 C21 T23 |
| Variola major virus L22579 | Bangladesh-1975 | A36 G11 C24 T20 | A33 G20 C20 T35 | A28 G16 C14 T26 | A36 G23 C15 T30 | A28 G21 C16 T35 | A36 G18 C21 T23 |

TABLE 3-continued

Orthopoxvirus Species Base Compositions for Primer Pair
Nos: 296, 297, 299, 310, 312 and 313

| Orthopoxvirus Species and GenBank Accession | Strain | Primer Pair No: 310 | Primer Pair No: 296 | Primer Pair No: 313 | Primer Pair No: 299 | Primer Pair No: 312 | Primer Pair No: 297 |
|---|---|---|---|---|---|---|---|
| | | | | [A G C T] | | | |
| Variola major virus S55844 | India-1967 | A36 G11 C24 T20 | A33 G20 C20 T35 | A28 G16 C14 T26 | A36 G23 C15 T30 | A28 G21 C16 T35 | A36 G18 C21 T23 |
| Variola major virus Y16780 | Garcia-1966 | A36 G11 C24 T20 | A34 G19 C21 T34 | A28 G16 C14 T26 | A36 G23 C15 T30 | A28 G21 C16 T35 | A36 G18 C21 T23 |

Various modifications of the invention, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, gene bank accession numbers, internet web sites, and the like) cited in the present application is incorporated herein by reference in its entirety. Those skilled in the art will appreciate that numerous changes and modifications may be made to the embodiments of the invention and that such changes and modifications may be made without departing from the spirit of the invention. It is therefore intended that the appended claims cover all such equivalent variations as fall within the true spirit and scope of the invention.

What is claimed is:

1. A purified oligonucleotide primer pair comprising a forward primer and a reverse primer wherein said forward primer is between 20 and 24 nucleobases in length and comprises at least 90% sequence identity with SEQ ID NO: 16 and said reverse primer is between 29 and 33 nucleobases in length and comprises at least 90% sequence identity with SEQ ID NO: 39, wherein said primer pair hybridizes to conserved regions of nucleic acid from multiple members of the *orthopoxvirus* genus so as to allow amplification of an orthopoxvirus identifying amplicon from an unknown orthopoxvirus wherein said amplicon comprises variable sequences between said conserved regions, and wherein the molecular mass of said orthopoxvirus identifying amplicon identifies the species of said unknown orthopoxvirus.

2. A composition comprising the primer pair of claim 1.

3. A kit comprising a primer pair comprising:

a purified oligonucleotide primer 20 to 24 nucleobases in length comprising at least 90% sequence identity with SEQ ID NO: 16; and a purified oligonucleotide primer 29 to 33 nucleobases in length comprising at least 90% sequence identity with SEQ ID NO: 39 wherein said primer pair hybridizes to conserved regions of nucleic acid from multiple members of the *orthopoxvirus* genus so as to allow amplification of an orthopoxvirus identifying amplicon from an unknown orthopoxvirus wherein said amplicon comprises variable sequences between said conserved regions, and wherein the molecular mass of said orthopoxvirus identifying amplicon identifies the species of said unknown orthopoxvirus.

4. The kit of claim 3 further comprising at least one calibration polynucleotide.

5. The kit of claim 3 further comprising at least one ion exchange resin linked to magnetic beads.

6. The purified oligonucleotide primer pair of claim 1 wherein at least one of said forward primer or said reverse primer comprises at least one modified nucleobase.

7. The purified oligonucleotide primer pair of claim 3 wherein said modified nucleobase is 5-propynyluracil or 5-propynylcytosine.

8. The purified oligonucleotide primer pair of claim 6 wherein said modified nucleobase is a mass modified nucleobase.

9. The purified oligonucleotide primer pair of claim 8 wherein said mass modified nucleobase is 5-Iodo-C.

10. The purified oligonucleotide primer pair of claim 6, wherein said modified nucleobase is a universal nucleobase.

11. The purified oligonucleotide primer pair of claim 10 wherein said universal nucleobase is inosine.

12. The purified oligonucleotide primer pair of claim 6 wherein said modified nucleobase comprises a molecular mass modifying tag.

13. The purified oligonucleotide primer pair of claim 1 wherein at least one of said forward primer or said reverse primer lacks a non-templated T residue at its 5'-end.

14. The purified oligonucleotide primer pair of claim 1 wherein at least one of said forward primer or said reverse primer comprises at least one non-template tag.

15. A method for generating an *orthopoxvirus* identifying amplicon comprising:

1) providing a purified oligonucleotide primer pair according to claim 1; and 2) contacting an unknown *orthopoxvirus* nucleic acid with the purified oligonucleotide primer pair under conditions suitable for nucleic acid amplification to generate an *orthopoxvirus* identifying amplicon.

* * * * *

SEQUENCE LISTING

```
<160> NUMBER OF SEQ ID NOS: 46

<210> SEQ ID NO 1
<211> LENGTH: 18
<212> TYPE: DNA
<213> ORGANISM: Artificial Sequence
<220> FEATURE:
<223> OTHER INFORMATION: PCR Primer

<400> SEQUENCE: 1
gaagttgaac cgggatca                                                        18

<210> SEQ ID NO 2
<211> LENGTH: 23
<212> TYPE: DNA
<213> ORGANISM: Artificial Sequence
<220> FEATURE:
<223> OTHER INFORMATION: PCR Primer

<400> SEQUENCE: 2
ctgtctgtag ataaactagg att                                                  23

<210> SEQ ID NO 3
<211> LENGTH: 18
<212> TYPE: DNA
<213> ORGANISM: Artificial Sequence
<220> FEATURE:
<223> OTHER INFORMATION: PCR Primer

<400> SEQUENCE: 3
ctcctccatc actaggaa                                                        18

<210> SEQ ID NO 4
<211> LENGTH: 15
<212> TYPE: DNA
<213> ORGANISM: Artificial Sequence
<220> FEATURE:
<223> OTHER INFORMATION: PCR Primer
```

```
<400> SEQUENCE: 4
cgatactacg gacgc                                                    15

<210> SEQ ID NO 5
<211> LENGTH: 18
<212> TYPE: DNA
<213> ORGANISM: Artificial Sequence
<220> FEATURE:
<223> OTHER INFORMATION: PCR Primer

<400> SEQUENCE: 5
gtactgaatc cgcctaag                                                 18

<210> SEQ ID NO 6
<211> LENGTH: 23
<212> TYPE: DNA
<213> ORGANISM: Artificial Sequence
<220> FEATURE:
<223> OTHER INFORMATION: PCR Primer

<400> SEQUENCE: 6
cgcgataata gatagtgcta aac                                           23

<210> SEQ ID NO 7
<211> LENGTH: 20
<212> TYPE: DNA
<213> ORGANISM: Artificial Sequence
<220> FEATURE:
<223> OTHER INFORMATION: PCR Primer

<400> SEQUENCE: 7
tagaagttga accgggatca                                               20

<210> SEQ ID NO 8
<211> LENGTH: 24
<212> TYPE: DNA
<213> ORGANISM: Artificial Sequence
<220> FEATURE:
<223> OTHER INFORMATION: PCR Primer

<400> SEQUENCE: 8
tctgtctgta gataaactag gatt                                          24

<210> SEQ ID NO 9
<211> LENGTH: 19
<212> TYPE: DNA
<213> ORGANISM: Artificial Sequence
<220> FEATURE:
<223> OTHER INFORMATION: PCR Primer

<400> SEQUENCE: 9
tctcctccat cactaggaa                                                19

<210> SEQ ID NO 10
<211> LENGTH: 16
<212> TYPE: DNA
<213> ORGANISM: Artificial Sequence
<220> FEATURE:
<223> OTHER INFORMATION: PCR Primer

<400> SEQUENCE: 10
tcgatactac ggacgc                                                   16

<210> SEQ ID NO 11
<211> LENGTH: 19
<212> TYPE: DNA
```

```
<213> ORGANISM: Artificial Sequence
<220> FEATURE:
<223> OTHER INFORMATION: PCR Primer

<400> SEQUENCE: 11
tgtactgaat ccgcctaag                                                    19

<210> SEQ ID NO 12
<211> LENGTH: 24
<212> TYPE: DNA
<213> ORGANISM: Artificial Sequence
<220> FEATURE:
<223> OTHER INFORMATION: PCR Primer

<400> SEQUENCE: 12
tcgcgataat agatagtgct aaac                                              24

<210> SEQ ID NO 13
<211> LENGTH: 28
<212> TYPE: DNA
<213> ORGANISM: Artificial Sequence
<220> FEATURE:
<223> OTHER INFORMATION: PCR Primer

<400> SEQUENCE: 13
tgatttcgta gaagttgaac cgggatca                                          28

<210> SEQ ID NO 14
<211> LENGTH: 27
<212> TYPE: DNA
<213> ORGANISM: Artificial Sequence
<220> FEATURE:
<223> OTHER INFORMATION: PCR Primer

<400> SEQUENCE: 14
ttctccctag aagttgaacc gggatca                                           27

<210> SEQ ID NO 15
<211> LENGTH: 21
<212> TYPE: DNA
<213> ORGANISM: Artificial Sequence
<220> FEATURE:
<223> OTHER INFORMATION: PCR Primer

<400> SEQUENCE: 15
tggtgacgat actacggacg c                                                 21

<210> SEQ ID NO 16
<211> LENGTH: 22
<212> TYPE: DNA
<213> ORGANISM: Artificial Sequence
<220> FEATURE:
<223> OTHER INFORMATION: PCR Primer

<400> SEQUENCE: 16
tcggtgacga tactacggac gc                                                22

<210> SEQ ID NO 17
<211> LENGTH: 22
<212> TYPE: DNA
<213> ORGANISM: Artificial Sequence
<220> FEATURE:
<223> OTHER INFORMATION: PCR Primer

<400> SEQUENCE: 17
tcggtgacga tactacggac gc                                                22
```

<210> SEQ ID NO 18
<211> LENGTH: 32
<212> TYPE: DNA
<213> ORGANISM: Artificial Sequence
<220> FEATURE:
<223> OTHER INFORMATION: PCR Primer

<400> SEQUENCE: 18
tggaaaaaaa gtatctcctc catcactagg aa            32

<210> SEQ ID NO 19
<211> LENGTH: 32
<212> TYPE: DNA
<213> ORGANISM: Artificial Sequence
<220> FEATURE:
<223> OTHER INFORMATION: PCR Primer

<400> SEQUENCE: 19
tggaaagtat ctcctccatc actaggaaaa cc            32

<210> SEQ ID NO 20
<211> LENGTH: 26
<212> TYPE: DNA
<213> ORGANISM: Artificial Sequence
<220> FEATURE:
<223> OTHER INFORMATION: PCR Primer

<400> SEQUENCE: 20
tccctcctct cctccatcac taggaa                   26

<210> SEQ ID NO 21
<211> LENGTH: 33
<212> TYPE: DNA
<213> ORGANISM: Artificial Sequence
<220> FEATURE:
<223> OTHER INFORMATION: PCR Primer

<400> SEQUENCE: 21
tctagtaaac gcgataatag atagtgctaa acg           33

<210> SEQ ID NO 22
<211> LENGTH: 31
<212> TYPE: DNA
<213> ORGANISM: Artificial Sequence
<220> FEATURE:
<223> OTHER INFORMATION: PCR Primer

<400> SEQUENCE: 22
tcctcctcgc gataatagat agtgctaaac g             31

<210> SEQ ID NO 23
<211> LENGTH: 29
<212> TYPE: DNA
<213> ORGANISM: Artificial Sequence
<220> FEATURE:
<223> OTHER INFORMATION: PCR Primer

<400> SEQUENCE: 23
tcctcccgcg ataatagata gtgctaaac               29

<210> SEQ ID NO 24
<211> LENGTH: 21
<212> TYPE: DNA
<213> ORGANISM: Artificial Sequence
<220> FEATURE:
<223> OTHER INFORMATION: PCR Primer

```
<400> SEQUENCE: 24
attatcggtc gttgttaatg t                                              21

<210> SEQ ID NO 25
<211> LENGTH: 18
<212> TYPE: DNA
<213> ORGANISM: Artificial Sequence
<220> FEATURE:
<223> OTHER INFORMATION: PCR Primer

<400> SEQUENCE: 25
cgttcttctc tggaggat                                                  18

<210> SEQ ID NO 26
<211> LENGTH: 22
<212> TYPE: DNA
<213> ORGANISM: Artificial Sequence
<220> FEATURE:
<223> OTHER INFORMATION: PCR Primer

<400> SEQUENCE: 26
ctataacatt caaagcttat tg                                             22

<210> SEQ ID NO 27
<211> LENGTH: 22
<212> TYPE: DNA
<213> ORGANISM: Artificial Sequence
<220> FEATURE:
<223> OTHER INFORMATION: PCR Primer

<400> SEQUENCE: 27
ctttatgaat tactttacat at                                             22

<210> SEQ ID NO 28
<211> LENGTH: 23
<212> TYPE: DNA
<213> ORGANISM: Artificial Sequence
<220> FEATURE:
<223> OTHER INFORMATION: PCR Primer

<400> SEQUENCE: 28
gtgaataaag tatcgcccta ata                                            23

<210> SEQ ID NO 29
<211> LENGTH: 19
<212> TYPE: DNA
<213> ORGANISM: Artificial Sequence
<220> FEATURE:
<223> OTHER INFORMATION: PCR Primer

<400> SEQUENCE: 29
gcttccacca ggtcattaa                                                 19

<210> SEQ ID NO 30
<211> LENGTH: 22
<212> TYPE: DNA
<213> ORGANISM: Artificial Sequence
<220> FEATURE:
<223> OTHER INFORMATION: PCR Primer

<400> SEQUENCE: 30
tattatcggt cgttgttaat gt                                             22

<210> SEQ ID NO 31
<211> LENGTH: 19
<212> TYPE: DNA
```

<213> ORGANISM: Artificial Sequence
<220> FEATURE:
<223> OTHER INFORMATION: PCR Primer

<400> SEQUENCE: 31
tcgttcttct ctggaggat                                              19

<210> SEQ ID NO 32
<211> LENGTH: 23
<212> TYPE: DNA
<213> ORGANISM: Artificial Sequence
<220> FEATURE:
<223> OTHER INFORMATION: PCR Primer

<400> SEQUENCE: 32
tctataacat tcaaagctta ttg                                         23

<210> SEQ ID NO 33
<211> LENGTH: 23
<212> TYPE: DNA
<213> ORGANISM: Artificial Sequence
<220> FEATURE:
<223> OTHER INFORMATION: PCR Primer

<400> SEQUENCE: 33
tctttatgaa ttactttaca tat                                         23

<210> SEQ ID NO 34
<211> LENGTH: 24
<212> TYPE: DNA
<213> ORGANISM: Artificial Sequence
<220> FEATURE:
<223> OTHER INFORMATION: PCR Primer

<400> SEQUENCE: 34
tgtgaataaa gtatcgccct aata                                        24

<210> SEQ ID NO 35
<211> LENGTH: 20
<212> TYPE: DNA
<213> ORGANISM: Artificial Sequence
<220> FEATURE:
<223> OTHER INFORMATION: PCR Primer

<400> SEQUENCE: 35
tgcttccacc aggtcattaa                                             20

<210> SEQ ID NO 36
<211> LENGTH: 31
<212> TYPE: DNA
<213> ORGANISM: Artificial Sequence
<220> FEATURE:
<223> OTHER INFORMATION: PCR Primer

<400> SEQUENCE: 36
tcgcgatttt attatcggtc gttgttaatg t                                31

<210> SEQ ID NO 37
<211> LENGTH: 30
<212> TYPE: DNA
<213> ORGANISM: Artificial Sequence
<220> FEATURE:
<223> OTHER INFORMATION: PCR Primer

<400> SEQUENCE: 37
tccctcccta ttatcggtcg ttgttaatgt                                  30

<210> SEQ ID NO 38
<211> LENGTH: 35
<212> TYPE: DNA
<213> ORGANISM: Artificial Sequence
<220> FEATURE:
<223> OTHER INFORMATION: PCR Primer

<400> SEQUENCE: 38
tccctcccaa tatctttacg aattacttta catat                              35

<210> SEQ ID NO 39
<211> LENGTH: 31
<212> TYPE: DNA
<213> ORGANISM: Artificial Sequence
<220> FEATURE:
<223> OTHER INFORMATION: PCR Primer

<400> SEQUENCE: 39
tcctccctcc catctttacg aattacttta c                                  31

<210> SEQ ID NO 40
<211> LENGTH: 34
<212> TYPE: DNA
<213> ORGANISM: Artificial Sequence
<220> FEATURE:
<223> OTHER INFORMATION: PCR Primer

<400> SEQUENCE: 40
tcctccctcc caatatcttt acgaattact ttac                               34

<210> SEQ ID NO 41
<211> LENGTH: 35
<212> TYPE: DNA
<213> ORGANISM: Artificial Sequence
<220> FEATURE:
<223> OTHER INFORMATION: PCR Primer

<400> SEQUENCE: 41
tccctcccga aaactataac attcaaagct tattg                              35

<210> SEQ ID NO 42
<211> LENGTH: 33
<212> TYPE: DNA
<213> ORGANISM: Artificial Sequence
<220> FEATURE:
<223> OTHER INFORMATION: PCR Primer

<400> SEQUENCE: 42
tccctccctc cctataacat tcaaagctta ttg                                33

<210> SEQ ID NO 43
<211> LENGTH: 30
<212> TYPE: DNA
<213> ORGANISM: Artificial Sequence
<220> FEATURE:
<223> OTHER INFORMATION: PCR Primer

<400> SEQUENCE: 43
tcctccctcc ctaacattca aagcttattg                                    30

<210> SEQ ID NO 44
<211> LENGTH: 25
<212> TYPE: DNA
<213> ORGANISM: Artificial Sequence
<220> FEATURE:
<223> OTHER INFORMATION: PCR Primer -continued

```
<400> SEQUENCE: 44
tgttcagctt ccaccaggtc attaa                                          25

<210> SEQ ID NO 45
<211> LENGTH: 27
<212> TYPE: DNA
<213> ORGANISM: Artificial Sequence
<220> FEATURE:
<223> OTHER INFORMATION: PCR Primer

<400> SEQUENCE: 45
tgtgttcagc ttccaccagg tcattaa                                        27

<210> SEQ ID NO 46
<211> LENGTH: 24
<212> TYPE: DNA
<213> ORGANISM: Artificial Sequence
<220> FEATURE:
<223> OTHER INFORMATION: PCR Primer

<400> SEQUENCE: 46
tcccagcttc caccaggtca ttaa                                           24
```